United States Patent
Hehn et al.

(10) Patent No.: US 12,213,970 B2
(45) Date of Patent: *Feb. 4, 2025

(54) PYRIDINYL SULFONAMIDE DERIVATIVES, PHARMACEUTICAL COMPOSITIONS AND USES THEREOF

(71) Applicant: Boehringer Ingelheim International GmbH, Ingelheim am Rhein (DE)

(72) Inventors: Joerg P. Hehn, Biberach an der Riss (DE); Andreas Blum, Bensheim (DE); Oliver Hucke, Warthausen (DE); Stefan Peters, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 518 days.

This patent is subject to a terminal disclaimer.

(21) Appl. No.: 17/285,916

(22) PCT Filed: Oct. 24, 2019

(86) PCT No.: PCT/EP2019/078991
§ 371 (c)(1),
(2) Date: Apr. 16, 2021

(87) PCT Pub. No.: WO2020/089025
PCT Pub. Date: May 7, 2020

(65) Prior Publication Data
US 2021/0353608 A1 Nov. 18, 2021

(30) Foreign Application Priority Data
Oct. 29, 2018 (EP) .................................... 18203192

(51) Int. Cl.
| | | |
|---|---|---|
| *A61K 31/4427* | (2006.01) | |
| *A61K 31/4439* | (2006.01) | |
| *A61K 31/4545* | (2006.01) | |
| *A61K 31/5377* | (2006.01) | |
| *A61P 29/00* | (2006.01) | |
| *A61P 35/00* | (2006.01) | |
| *C07D 401/12* | (2006.01) | |
| *C07D 401/14* | (2006.01) | |
| *C07D 405/14* | (2006.01) | |

(52) U.S. Cl.
CPC ...... *A61K 31/4439* (2013.01); *A61K 31/4427* (2013.01); *A61K 31/4545* (2013.01); *A61K 31/5377* (2013.01); *C07D 401/12* (2013.01); *C07D 401/14* (2013.01); *C07D 405/14* (2013.01)

(58) Field of Classification Search
CPC . A61K 31/4439; A61K 31/4427; A61P 29/00; A61P 35/00
See application file for complete search history.

(56) References Cited

U.S. PATENT DOCUMENTS

| | | | |
|---|---|---|---|
| 7,579,449 B2 | 8/2009 | Eckhardt et al. |
| 7,666,848 B2 | 2/2010 | Sanofi |
| 7,713,938 B2 | 5/2010 | Himmelsbach et al. |
| 7,745,414 B2 | 6/2010 | Eckhardt et al. |
| 7,767,651 B2 | 8/2010 | Kobayashi |
| 7,977,466 B2 | 7/2011 | Imamura |
| 7,989,622 B2 | 8/2011 | Bajjalieh et al. |
| 8,017,792 B2 | 9/2011 | Taisho |
| 8,802,679 B2 | 8/2014 | Yoshihara et al. |
| 8,802,842 B2 | 8/2014 | Weber et al. |
| 9,163,051 B2 | 10/2015 | Murakata |
| 9,873,714 B2 | 1/2018 | Weber et al. |
| 10,442,795 B2 | 10/2019 | Eckhardt et al. |
| 10,577,363 B2 | 3/2020 | Mitchell et al. |
| 2004/0214928 A1 | 10/2004 | Aronov et al. |
| 2008/0096892 A1 | 4/2008 | Cheng et al. |
| 2010/0197908 A1 | 8/2010 | Lehmann-Lintz et al. |

(Continued)

FOREIGN PATENT DOCUMENTS

| | | |
|---|---|---|
| CA | 2830157 A1 | 9/2012 |
| CN | 109251166 A | 1/2019 |

(Continued)

OTHER PUBLICATIONS

Cancer Research UK ("Types of cancer." https://www.cancerresearchuk.org/about-cancer/what-is-cancer/how-cancer-starts/types-of-cancer. Last reviewed: Oct. 9, 2023). (Year: 2023).*

(Continued)

*Primary Examiner* — Amanda L. Aguirre
*Assistant Examiner* — Chris E Simmons
(74) *Attorney, Agent, or Firm* — Shelley A. Jones

(57) ABSTRACT

The invention relates to new pyridinyl sulfonamide derivatives of the formula

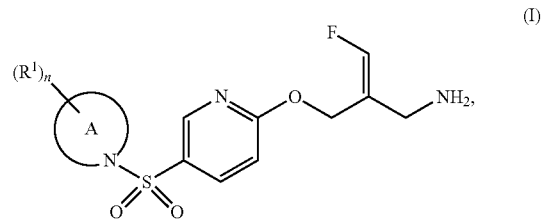

wherein R¹, A and n are as defined herein, to their use as medicaments, to methods for their therapeutic use and to pharmaceutical compositions containing them.

16 Claims, No Drawings

(56) References Cited

U.S. PATENT DOCUMENTS

| | | | |
|---|---|---|---|
| 2015/0158813 | A1 | 6/2015 | Deodhar et al. |
| 2017/0327483 | A1 | 11/2017 | Blum et al. |
| 2018/0297987 | A1 | 10/2018 | Coates et al. |
| 2019/0084959 | A1 | 3/2019 | Himmelsbach et al. |
| 2021/0353608 | A1 | 11/2021 | Hehn et al. |
| 2021/0361637 | A1* | 11/2021 | Hehn .................. C07D 213/71 |

FOREIGN PATENT DOCUMENTS

| | | | |
|---|---|---|---|
| EP | 1213296 | A1 | 6/2002 |
| EP | 1344780 | A1 | 9/2003 |
| EP | 1354888 | A1 | 10/2003 |
| EP | 1489089 | A1 | 12/2004 |
| EP | 2695881 | A1 | 2/2014 |
| EP | 3617186 | A1 | 3/2020 |
| EP | 3626699 | A1 | 3/2020 |
| EP | 3715341 | A1 | 9/2020 |
| JP | 2006515319 | A | 5/2006 |
| JP | 2008512346 | A | 4/2008 |
| JP | 2015521167 | A | 7/2015 |
| JP | 2017528464 | A | 9/2017 |
| JP | 2019512016 | A | 5/2019 |
| JP | 2019527717 | A | 10/2019 |
| JP | 7317109 | B2 | 7/2023 |
| NO | 2008002824 | A1 | 1/2008 |
| WO | 1998027086 | A1 | 6/1998 |
| WO | 0127128 | A1 | 4/2001 |
| WO | 20010023594 | A2 | 4/2001 |
| WO | 2003099836 | A1 | 12/2003 |
| WO | 2005012326 | A1 | 2/2005 |
| WO | 2006028269 | | 3/2006 |
| WO | 2007120528 | A2 | 10/2007 |
| WO | 2007140191 | A2 | 12/2007 |
| WO | 2008042688 | A2 | 4/2008 |
| WO | 2008069327 | A1 | 6/2008 |
| WO | 2008071646 | A1 | 6/2008 |
| WO | 2008116179 | A1 | 9/2008 |
| WO | 2009014970 | A1 | 1/2009 |
| WO | 2009026319 | A1 | 2/2009 |
| WO | 2009035969 | A1 | 3/2009 |
| WO | 2010009197 | A1 | 1/2010 |
| WO | 2010119990 | A1 | 10/2010 |
| WO | 2011034078 | A1 | 3/2011 |
| WO | 12120195 | A1 | 9/2012 |
| WO | 12124696 | A1 | 9/2012 |
| WO | 2013163675 | A1 | 11/2013 |
| WO | 2017022861 | A1 | 2/2017 |
| WO | 2017148519 | A1 | 9/2017 |
| WO | 2017194453 | | 11/2017 |
| WO | 2018027892 | A1 | 2/2018 |
| WO | 2018028517 | A1 | 2/2018 |
| WO | 2018146471 | A1 | 8/2018 |
| WO | 2018148856 | A1 | 8/2018 |
| WO | 2018149226 | A1 | 8/2018 |
| WO | 2019024924 | A1 | 2/2019 |
| WO | 2019201752 | | 10/2019 |

OTHER PUBLICATIONS

Hu et al. (Cell Death Discovery (2023) 9:124 ; https://doi.org/10.1038/s41420-023-01428-8 (Year: 2023).*

International Search Report for PCT/EP2016/054541 mailed May 27, 2016.

International Search Report for PCT/EP2016/054540 mailed May 25, 2016.

Nobili, World Journal of Gastroenterolgy, Pediatric non alcoholic fatty Liver disease: preventive and therapeutic value of lifestyle intervention, 2009.

Shen, UC Berkley E thesis and Dissertations, In Search of pysiological role for amine oxidase, cooper containing -3 (AOC3) in adipocytes, 2010.

International Search Report and Written Opinion for PCT/EP20170600890, mailed Jun. 6, 2017.

Yamaki, Synthesis and structure activity relationships of carbamimidoylcarbamate derivatives as novel vascular adhesion protein-1 inhibitors, Bioorganic and medicinal Chemistry, 2017, p. 6024-6038.

Seufert, SGLT inhibitors-an insulin independent therapeutic approach, Diabetes, 2015.

Bell, The potent synergistic effects of the combination of liraglutide, Amercian J. of Case reports, vol. 15, 2014.

Abdul-Ghani, Where does Combination Therapy with an SGLT2 Inhibitor, Diabetes Care, vol. 38, 2015.

International Search Report for PCT/Ep2019/059341 mailed Mar. 7, 2019.

Written Opinion of the International Search Authorty, PCT/EP/2019/059341 mailed Mar. 7, 2019.

Gressner, Validity of Monoamine Oxidase In Serum for Diagnosis of Liver Cirrhosis, J. Clin Chem. Biochem, 1982.

Kleiner, Design and Validation of a Histological scoring System, Hepatolology, 2005.

McEwen, Abnormalities of Serum monoamine oxidase in chronic Liver Disease, J. Lab A. Clin. Med., 1967.

Chassande, The human gene for Diamine Oxidase, The Journal of Biological Chemistry, 1994.

Imamura, Human Retina-Specific Amine Oxidase cDNA cloning, Tissue Expression, Genomica, vol. 40, 1996.

Schwelberger, The origin of mammalian plasma amine oxidases, J. Neural Transm, vol. 114, 2007.

Dunkel, Semi-carbazide-Sensitive Amine Oxidase/Vascular Adhesion Protein 1, Current Medicinal Chem, vol. 15, 2008.

Katsuki, Homeostasis Model Assesssment is a reliable indicator of insulin resistance during follow up of patients with type 2 diabetes, Diabestes Care, vol. 24, 2001.

Matthews, Homeostasis model assessment: insulin resistance, Diabetologica, vol. 28, 1985.

Galvin, A simple method for Quantitiation of Insulin Sensitivity, Diabetic Meds, 1992.

Meigs, The Natural History of progressionform Normal glucose toleranceto type 2 diabetes, Diabestes, vol. 82, 2003.

Diabetes Care, The Prevention or Delay of Type 2 Diabetes, American Diabetes Assoc., vol. 25, 2002.

Stomvall, The OGTT test as test for beta cell function?, European J. of clinical Investigation, vol. 31, 2001.

Laaksonen, Metabolic Syndrome and Development of Diabetes Mellitus, American Journal od Epidemiology, 2002.

Stomvall, Use of the Oral Glucose Tolerance Test to Assess Insulin Release and Insulin Sensitivity, Diabetes Care, vol. 23, 2000.

Grempler, Empagliflozin, a novel selective sodium co-transorter-2 inhibitor, Diabetes, Obesity and Metabolism, vol. 14, 2012.

Zinman, Empagliflozin, Cardiovascular Outcomes and Mortality in Type 2 Diabetes, New England Journal of Med., 2015.

Folch, A simple method for the isolation and purification of total lipides from animal tissues, J. biol Chem, 1957.

Jojima, Empaglaiflazin, alone or in combo with linagliptin a DPP-4 inhibitor prevents steatohepatitis in a novel mouse model of non-alcoholic steatohepatitis and diabetes, Diabetology & Metabolic Syndrome, 2016.

International Search report for PCT/EP2019/078992 mailed Dec. 29, 2019.

Written Opinion for PCT/EP2019/078992 mailed Dec. 29, 2019.

Brnardic et al., "Discovery of pyrrolidine sulfonamides as selective and orally bioavailable antagonists of transient receptor potential vanilloid 4 (TRPV4)", Journal of Medicinal Chemistry, 2018, 61.21, pp. 9738-9755.

Cleeman et al., "Executive Summary of the Third Report of the National Cholesterol Education Program (NCEP) Expert Panel on Detection, Evaluation, and Treatment of High Blood Cholesterol in Adults (Adult Treatment Panel III)", JAMA, 2001, vol. 285, pp. 2486-2497.

Ford et al., "Prevalence of the Metabolic Syndrome among US adults: Findings from the Third National Health and Nutrition Examination Survey", JAMA, 2002, vol. 287, pp. 356-359.

(56) References Cited

OTHER PUBLICATIONS

Foot et al., "PXS-4681A, a Potent and Selective Mechanism-Based Inhibitor of SSAO/VAP-1 with Anti-Inflammatory Effects In Vivo", The Journal of Pharmacology and Experiment Therapeutics, Nov. 30, 2013, vol. 347, pp. 365-374.
Abstract in English for CN109251166, Jan. 22, 2019.
Abstract in English for WO2019024924, Feb. 7, 2019.
Giron, "Thermal analysis and calorimetric methods in the characterisation of polymorphs and solvates", Thermochimica acta, Elsevier Science, B.V., vol. 248, 1995, p. 1-59.
Remington's Pharmaceutical Sciences, 16th Ed., Mack Pub. Co., 1980, p. 180-181.

* cited by examiner

PYRIDINYL SULFONAMIDE DERIVATIVES, PHARMACEUTICAL COMPOSITIONS AND USES THEREOF

FIELD OF THE INVENTION

This invention relates to new compounds, in particular pyridinyl sulfonamide derivatives, to processes for preparing such compounds, to their use as inhibitors of AOC3, to methods for their therapeutic use, in particular in diseases and conditions mediated by the inhibition of AOC3, and to pharmaceutical compositions comprising them.

BACKGROUND OF THE INVENTION

The enzymatic activity of AOC3 (amine oxidase, copper containing 3; vascular adhesion protein 1) has been described already in 1967 as a monoamine oxidase activity in the plasma of chronic liver disease patients (Gressner, A. M. et al., 1982, J. Clin. Chem. Clin. Biochem. 20: 509-514; McEwen, C. M., Jr. et al., 1967, J. Lab Clin. Med. 70: 36-47). AOC3 has two closely homologous genes in the human genome: AOC1 which corresponds to a diamine oxidase (Chassande, O. et al., 1994, J. Biol. Chem. 269: 14484-14489) and AOC2, a SSAO with a specific expression in the retina (Imamura, Y. et al., 1997, Genomics 40: 277-283). AOC4 is a sequence that does not lead to a functional gene product in humans due to an internal stop-codon (Schwelberger, H. G., 2007, J. Neural Transm. 114: 757-762).

The enzyme contains an oxidized 2,4,5-trihydroxy-phenylalaninequinone (TPQ) and a copper ion in the active side. This characteristic catalytic center classifies the semi-carbazide-sensitive amine oxidase (SSAO, copper-containing amine:oxygen oxido-reductase (deaminating)): The type II membrane protein belongs to the family of copper containing amine oxidases together with several other diamine and the lysyl oxidases. However, the later enzymes can be distinguished from AOC3 in their preference for diamines and the low sensitivity towards semicarbazide inhibition (Dunkel, P. et al., 2008, Curr. Med. Chem. 15: 1827-1839). On the other hand, monoamine oxidases contain the flavin adenine dinucleotide (FAD) cofactor in their reactive center like monoamine oxidase A (MAO-A) and monoamine oxidase B (MAO-B) and follow therefore a different reaction scheme.

AOC3 catalyzes a two-step reaction mechanism for the oxidative deamination of primary aliphatic and aromatic amines. In a first reaction, the primary amine forms a Schiff-base with a TPQ carbonyl group. After abstraction of a proton from the carbon in α-position to the amino group, hydrolysis takes place and an aldehyde and the aminoquinol form of TPQ are formed in the active site. In the presence of oxygen, the aminoquinol form of TPQ is oxidized and hydrolyzed to re-generate TPQ under the formation of ammonia and peroxide with the help of the copper ion (Mure, M. et al., 2002, Biochemistry 41: 9269-9278). Several substrates of AOC3 have been described, like the physiological amines methylamine, dopamine, or aminoacetone, whose products of oxidation have been associated to cardiovascular pathologies (Yu, P. H. et al., 1993, Diabetes 42: 594-603). Synthetic amines have been optimized for their turnover by AOC3 like benzylamine derivates (Yraola, F. et al., 2006, J. Med. Chem. 49: 6197-6208), C-Naphthalen-1-methylamine (Marti, L. et al., 2004, J. Med. Chem. 47: 4865-4874) or luciferin derivates (Valley, M. P. et al., 2006, Anal. Biochem. 359: 238-246). The later substrate can be used for the sensitive detection of AOC3 activity in plasma, tissue or for biochemical characterization of the enzyme.

Under pathophysiological conditions of high AOC3 activity the aldehyde products are highly reactive, leading to advanced glycosylation end products (Mathys, K. C. et al., 2002, Biochem. Biophys. Res. Commun. 297: 863-869) which are regarded as markers and drivers of diabetes associated inflammatory mechanisms.

Furthermore, the byproduct hydrogen peroxide is sensed by the tissue as a messenger of inflammation. This reaction product is able to activate the endothelium and is fostering the activation of leukocytes.

The binding and modification of Siglec-10 as a membrane bound substrate provides a mechanistic understanding of how the enzymatic reaction could trigger the leukocyte transmigration through activated endothelia. The binding of Siglec-10 to AOC3 was shown in several adhesion assays and led to increased hydrogen peroxide production (Kivi, E. et al., 2009, Blood 114: 5385-5392). Binding of activated leukocytes to the dimeric, extracellular AOC3 via the Siglec-10 generates a transient association to the activated endothelium. Therefore, the rolling velocity of leukocytes is reduced, which increases the transmigration of leukocytes into the interstitium of inflamed tissues. Further, a conserved RGD-motif on the surface of AOC3 argues for its adhesive role: The deletion of this sequence reduced leukocyte recruitment (Salmi, M. et al., 2000, Circ. Res. 86: 1245-1251), probably via a lack of integrin β1 binding activity (Aspinall, A. I. et al., 2010, Hepatology 51: 2030-2039).

This finding correlates to the phenotype of AOC3 knock out mice, which exert a reduced leukocyte and lymphocyte transmigration capacity (Stolen, C. M. et al., 2005, Immunity. 22: 105-115) into lymphoid organs and adipose tissue (Bour, S. et al., 2009, Am. J. Pathol. 174: 1075-1083).

AOC3 activity can be found in most tissues and is mainly expressed in endothelial cells, smooth muscle cells and adipocytes (Boomsma, F. et al., 2000, Comp Biochem. Physiol C. Toxicol. Pharmacol. 126: 69-78; O'Sullivan, J. et al., 2004, Neurotoxicology 25: 303-315). In humans, in contrast to mice, AOC3 activity is constitutive in the liver sinusoideal endothelial cells (McNab, G. et al., 1996, Gastroenterology 110: 522-528) and mRNA expression is further upregulated under inflammatory conditions in this tissue (Lalor, P. F. et al., 2002, Immunol. Cell Biol. 80: 52-64); Bonder, C. S. et al., 2005, Immunity. 23: 153-163). AOC3 not only exists as a membrane protein, but can also be found as soluble plasma activity probably due to a metalloprotease mediated shedding process (Abella, A. et al., 2004, Diabetologia 47: 429-438); Boomsma, F. et al., 2005, Diabetologia 48: 1002-1007; Stolen, C. M. et al., 2004, Circ. Res. 95: 50-57)). Elevated levels of soluble AOC3 have been observed in diabetes (Li, H. Y. et al., 2009, Clin. Chim. Acta 404: 149-153), obesity (Meszaros, Z. et al., 1999, Metabolism 48: 113-117; Weiss, H. G. et al., 2003, Metabolism 52: 688-692), congestive heart failure (Boomsma, F. et al., 1997, Cardiovasc. Res. 33: 387-391), hemorrhagic stroke (Hernandez-Guillamon, M. et al, 2012, Cerebrovasc. Dis. 33, 55-63), end-stage renal disease (Kurkijarvi, R. et al., 2001, Eur. J. Immunol. 31: 2876-2884) and inflammatory liver disease (Kurkijarvi, R. et al., 1998, J. Immunol. 161: 1549-1557). For the latter, levels of AOC3 plasma activity have been correlated to liver fibrosis and serve as a predictor in patients with NAFLD (Weston, C. J. et al., 2011, J. Neural Transm. 118: 1055-1064). After transplantation of cirrhotic livers, high AOC3 plasma levels returned to normal values, which argues for the liver as the major source of plasma AOC3 activity under this pathological condition (Boomsma, F. et al., 2003, Biochim. Biophys. Acta 1647: 48-54).

The role of AOC3 in the activation of inflammation via peroxide generation and the recruitment of leukocytes to activated endothelium makes it an attractive target for the treatment of inflammatory components in several diseases. Therefore, a variety of small molecular compounds and antibodies have been tested in different disease animal models. Amongst those, the inhibition of AOC3 showed beneficial effects in the models of melanoma and lymphoma cancer (Marttila-Ichihara, F. et al., 2010, J. Immunol. 184: 3164-3173), acute and chronic joint (Tabi, T. et al., 2013, J. Neural Transm. 120: 963-967) or lung (Foot, J. S. et al., 2013, J. Pharmacol. Exp. Ther. 347: 365-374, Schilter, H. C. et al., 2015, Resp. Res. 16:42) inflammation, diabetic macular edema (Inoue, T. et al., 2013, Bioorg. Med. Chem. 21: 1219-1233), kidney fibrosis (Wong, M. et al., 2014, Am. J. Physiol Renal Physiol 307: F908-F916), liver allograft rejection (Martelius, T. et al., 2004, Am. J. Pathol. 165: 1993-2001) and non-alcoholic liver disease.

The development of a potent and well tolerated AOC3 inhibitor would therefore be beneficial for the treatment of the respective human diseases.

The amine oxidase copper containing 2 (AOC2) enzyme is a family member of homodimeric amine oxidases sensitive to the inhibition of semicarbazide. The human enzyme shares 65% of its amino acids with the closest homolog AOC3 (Zhang et al., 2003, Gene 318: 45-53). Recombinant overexpression of the longer version sv1 provides evidence of cell surface expression and enzymatic activity, whereas the shorter version sv2 remains cytoplasmatic in a HEK293 in vitro expression system. AOC2 and AOC3 exhibit different substrate profiles due to structural differences in the active sites: AOC2 exerts a high prevalence for 2-phenylethylamine and tryptamine and a low activity on the turnover of methylamine or benzylamine compared to AOC3 enzymatic activity. Nevertheless, both enzymes can form heterodimers that reconstitute enzymatic active centers with retained substrate selectivity. Expression analysis of AOC2 mRNA shows a broad expression of the two splice variants sv1 and sv2 of the AOC2 gene in lung, brain, heart, liver, kidney, pancreas and peripheral blood lymphocytes (Kaitaniemi et al., 2009, Cellular and Molecular Life 66: 2743-2757). According to AOC2 enzymatic tissue activity, the only human tissue with high AOC2-like activity is the retina and expression is associated to the retinal capillaries as shown by immune-histological studies. In the mouse, the highest mRNA expression of AOC2 is also found in the mouse retina, however the signals of mRNA and protein expression are found predominantly in the retinal ganglion cell layer. In the rat, the genomic sequence of AOC2 gene contains a stop codon in the exon 1 region, which defines the peptide length to 17% of the mouse and human AOC2 protein giving rise to a non-functional protein (Zhang et al., 2003, Gene 318: 45-53).

According to enzymatic function and localization of expression, AOC2 physiological function can be reminiscent of the AOC3 homolog which is described as relevant for e.g. neurovascular, retinal inflammation and recruitment of immune cells (Matsuda et al., 2017, Invest Ophthalmol Vis Sci. 58(7): 3254-3261, Noda et al., 2008, FASEB J. 4: 1094-103). Data on pharmacological inhibition or genetic depletion of AOC2 is not available so far and it is therefore difficult to estimate the contribution of AOC2 to retinal-vascular inflammation.

Nonetheless, as compared to AOC3 inhibition alone, a combined inhibition of AOC2 and AOC3 might increase anti-inflammatory potency in man, in particular for the treatment of ocular diseases.

AOC3 inhibitors are known in the art, for example, the compounds disclosed in WO 2013/163675, WO 2018/027892, WO 2018/148856 and WO 2018/149226. The pyridinyl sulfonamide derivatives of the present invention may provide several advantages, such as enhanced potency, improved selectivity, reduced plasma protein binding, improved CYP (cytochrome P450) enzyme profile and high metabolic stability, high chemical stability, improved tissue distribution, e.g. reduced brain exposure, improved side effect profile and/or tolerability and in consequence low toxicity, reduced risk to cause adverse events or undesirable side effects, and enhanced solubility.

The pyridinyl sulfonamides of the present invention exhibit increased inhibition of human AOC2.

The pyridinyl sulfonamide derivatives of the present invention exhibit increased selectivity towards AOC1. AOC1 expression and enzymatic activity is mainly found in the gut, placenta and kidney. The enzyme catalyzes the oxidation of primary amines derived from nutrition and protects the individuum from cardiometabolic effects of histamine, putrescine, tryptamine and cadaverine. Inhibition of AOC1 can lead to impaired tolerance to ingested histamine, resulting in increased plasma and tissue histamine-levels which can cause adverse events or undesirable side effects like decreased aterial pressure and compensation by increased heart-rate, tachycardia, headache, flush, urticaria, pruritus, bronchospasm and cardiac arrest (Maintz L. and Novak N. 2007. Am. J. Clin. Nutr. 85: 1185-96). The consequence of AOC1 inhibition in combination with histamine intake has been demonstrated in experiments with pigs: After the application of the AOC1-inhibitor aminoguanidine (100 mg/kg) and gavage of histamine (2 mg/kg) animals experienced increased histamine blood levels accompanied with a drop of blood pressure, increased heart rate, flushing, vomiting and death (3 out of 15 animals) (Sattler J. 1988. Agents and Actions, 23: 361-365) under the experimental conditions. Histamine intolerance in humans was associated to mutations in the promoter region of AOC1, leading to reduced mRNA expression and plasma AOC1 activity (Maintz et al. 2011. Allergy 66: 893-902).

The pyridinyl sulfonamide derivatives of the present invention exhibit increased selectivity towards MAO-A. This flavoenzyme catalyzes the oxidation of primary amines such as the neurotransmitters dopamine, epinephrine, norepinephrine and serotonine. Based on this function, MAO-A is considered to be a key regulator for brain function and there is a link between low activity of MAO and several behavioral and neurological disorders (Shih, J. C. et al. 1999, Annu. Rev. Neurosci. 22: 197-217; Frazzetto G. et al. 2007, PLoS ONE 5: e486). Furthermore, MAO-A plays an important role in the pathogenesis of cardiovascular disorders (Gupta V et al, 2015, J. of Neurochemistry, 134: 21-38). MAO-A physiologically metabolizes tyramine and consequently protects humans from pathologically high levels of tyramine. Inhibition of MAO-A can lead to a hypertensive crisis if food and beverages high in tyramine are ingested (Sathyanarayana Rao, T. S. 2009, Indian J. of Psychiatry, 51: 65-66).

Aim of the Present Invention

The aim of the present invention is to provide new compounds, in particular new pyridinyl sulfonamide derivatives, which are active with regard to AOC2 and AOC3.

A further aim of the present invention is to provide new compounds, in particular new pyridinyl sulfonamide derivatives, which have an inhibitory effect on AOC2 and AOC3 in vitro and/or in vivo and possess suitable pharmacological and pharmacokinetic properties to use them as medicaments.

A further aim of the present invention is to provide effective dual AOC2 and AOC3 inhibitors, in particular for the treatment of various diseases, for example of cancer, NASH (non-alcoholic steatohepatitis), pulmonary fibrosis, retinopathy, nephropathy and stroke, in particular hemorrhagic stroke.

Another aim of the present invention is to provide effective dual AOC2 and AOC3 inhibitors for the treatment of metabolic disorders such as cancer, NASH (non-alcoholic steatohepatitis), pulmonary fibrosis, retinopathy, nephropathy and stroke, in particular hemorrhagic stroke.

A further aim of the present invention is to provide methods for treating a disease or condition mediated by the inhibition of AOC2 and AOC3 in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular pyridinyl sulfonamide derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

Within the scope of the present invention it has now surprisingly been found that the new compounds of general formula (I) as described hereinafter exhibit an inhibiting activity with regard to AOC2 and AOC3.

According to another aspect of the present invention it has been found that the new compounds of general formula (I) as described hereinafter exhibit an inhibiting activity with regard to AOC2 and AOC3.

In a first aspect the present invention provides a compound of general formula

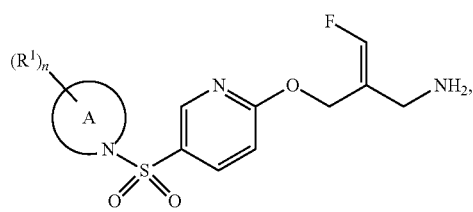

wherein
ring A is selected from the group A-G1 consisting of:

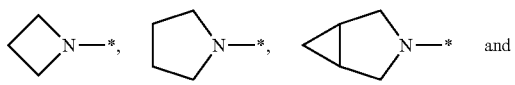

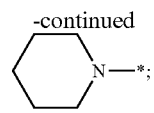

$R^1$ is selected from the group consisting of H, F, Cl, Br, CN, —OH, $C_{1-4}$-alkyl, —O—($C_{1-4}$-alkyl), —($CH_2)_m$—COOH, —($CH_2)_m$—C(=O)—O—($C_{1-4}$-alkyl), —($CH_2)_m$—C(=O)-heterocyclyl, —($CH_2)_m$—C(=O)—$NH_2$, —($CH_2)_m$—C(=O)—NH—($C_{1-4}$-alkyl), —($CH_2)_m$—C(=O)—N($C_{1-4}$-alkyl)$_2$, —C(=O)—NH—$C_{3-6}$-cycloalkyl, —C(=O)—NH-heterocyclyl, —($CH_2)_m$—NH—C(=O)—($C_{1-3}$-alkyl), —N($C_{1-3}$-alkyl)-C(=O)—($C_{1-4}$-alkyl), —N($C_{1-3}$-alkyl)-C(=O)—$NH_2$, —NH—C(=O)—NH—($C_{1-4}$-alkyl), heterocyclyl and phenyl, wherein each alkyl group or sub-group is optionally substituted with 1 or more F atoms or with one OH or —O—($C_{1-3}$-alkyl) group; and wherein each heterocyclyl is selected from the group consisting of azetidinyl, imidazolidinyl, piperidinyl, tetrahydropyranyl, morpholinyl and is optionally substituted with one or two groups independently selected from the group consisting of OH, oxo, $C_{1-3}$-alkyl, —C(=O)—$CH_3$ and —C(=O)-cyclopropyl group;

wherein multiple $R^1$ may be identical or different, if n is 2; and n is an integer selected from 1 and 2; and m is an integer selected from 0, 1 and 2; and wherein in any definition mentioned hereinbefore, if not specified otherwise, any alkyl group or sub-group may be straight-chained or branched and is optionally substituted with 1 or more F atoms, a tautomer or stereoisomers thereof, or a salt thereof, or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of AOC3 in a patient in need thereof characterized in that a compound of general formula (I) or a pharmaceutically acceptable salt thereof is administered to the patient.

According to another aspect of the invention, there is provided a method for treating cancer, NASH (non-alcoholic steatohepatitis), pulmonary fibrosis, retinopathy, nephropathy or stroke in a patient in need thereof characterized in that a compound of general formula (I) or a pharmaceutically acceptable salt thereof is administered to the patient.

According to another aspect of the invention, there is provided the use of a compound of the general formula (I) or a pharmaceutically acceptable salt thereof for the manufacture of a medicament for a therapeutic method as described above or hereinafter.

According to another aspect of the invention, there is provided a compound of the general formula (I) or a pharmaceutically acceptable salt thereof for use in a therapeutic method as described above or hereinafter.

In a further aspect this invention relates to a method for treating a disease or condition mediated by the inhibition of AOC3 in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) or a pharmaceutically acceptable salt thereof in combination with one or more additional therapeutic agents for the treatment or prevention of diseases or conditions which are mediated by the inhibition of AOC3.

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly A, $R^1$ and $R^2$, are defined as above and hereinafter. If residues, substituents or groups occur several times in a compound, as for example $R^2$, they may have the same or different meanings. Some preferred meanings of individual groups and substituents of the compounds according to the invention will be given hereinafter. Any and each of these definitions may be combined with each other.

A:

A-G1:

Ring A is preferably selected from the group A-G1 as defined above.

A-G2:

In another embodiment, ring A is selected from the group A-G2 consisting of

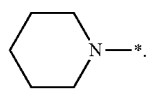

A-G3:

In another embodiment, ring A is selected from the group A-G3 consisting of

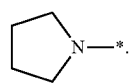

A-G4:

In another embodiment, ring A is selected from the group A-G4 consisting of

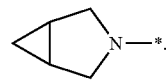

A-G5:

In another embodiment, ring A is selected from the group A-G5 consisting of

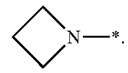

$R^1$:

$R^1$-G1:

The group $R^1$ is preferably selected from the group $R^1$-G1 as defined above.

$R^1$-G1a:

In one embodiment the group $R^1$ is selected from the group $R^1$-G1a consisting of:

H, F, —OH, $C_{1-2}$-alkyl, —O—($C_{1-2}$-alkyl), —$(CH_2)_m$—COOH, —$(CH_2)_m$—C(=O)—O—($C_{1-2}$-alkyl), —$(CH_2)_m$—C(=O)-heterocyclyl, —$(CH_2)_m$—C(=O)—$NH_2$, —$(CH_2)_m$—C(=O)—NH—($C_{1-4}$-alkyl), —$(CH_2)_m$—C(=O)—N($C_{1-2}$-alkyl)$_2$, —C(=O)—NH-cyclopropyl, —C(=O)—NH-heterocyclyl, —$(CH_2)_m$—NH—C(=O)—($C_{1-2}$-alkyl) and -heterocyclyl, wherein each alkyl group or sub-group is optionally substituted with 1 or more F atoms or with one OH or —O—($C_{1-2}$-alkyl) group; and wherein each heterocyclyl is selected from the group consisting of azetidinyl, imidazolidinyl, piperidinyl, tetrahydropyranyl, morpholinyl and is optionally substituted with one or two groups independently selected from the group consisting of OH, oxo, $C_{1-2}$-alkyl, —C(=O)—$CH_3$ and —C(=O)-cyclopropyl;

wherein m is 0 or 1; and wherein multiple $R^1$ may be identical or different, if n is 2.

$R^1$-G1b:

In another embodiment the group $R^1$ is selected from the group $R^1$-G1 b consisting of:

H, —OH, —$CH_3$, $CF_3$, —O—$CH_3$, —$(CH_2)_m$—COOH, —$(CH_2)_m$—C(=O)—O—($CH_3$), —$(CH_2)_m$—C(=O)-heterocyclyl, —$(CH_2)_m$—C(=O)—$NH_2$, —C(=O)—NH—($C_{1-4}$-alkyl), —C(=O)—N($CH_3$)$_2$, —C(=O)—NH-cyclopropyl, —C(=O)—NH-tetrahydropyranyl, —$(CH_2)_m$—NH—C(=O)—($C_{1-2}$-alkyl) and 3-methyl-2-oxo-imidazolidin-1-yl, wherein each alkyl group or sub-group is optionally substituted with 1 to 3 F atoms or with one OH or —O—$CH_3$ group; and wherein each heterocyclyl is selected from the group consisting of azetidinyl and morpholinyl and is optionally substituted with one OH group;

wherein m is 0 or 1; and wherein multiple $R^1$ may be identical or different, if n is 2.

$R^1$-G1c:

In another embodiment the group $R^1$ is selected from the group $R^1$-G1c consisting of:

H, —OH, —$CH_3$, $CF_3$, —O—$CH_3$, —COOH, —$(CH_2)_m$—C(=O)—O—($CH_3$), —$(CH_2)_m$—C

—C(=O)—NH$_2$, —C(=O)—NH—(C$_{1-2}$-alkyl), —C(=O)—N(CH$_3$)$_2$, —NH—C(=O)—(C$_{1-2}$-alkyl) and 3-methyl-2-oxo-imidazolidin-1-yl,
   wherein m is 0 or 1; and
   wherein multiple R$^1$ may be identical or different, if n is 2.

If n is 2, the second R$^1$ group of R$^1$-G1, R$^1$-G1a, R$^1$-G1b or R$^1$-G1c is preferably selected from the group consisting of CH$_3$ and CF$_3$.

R$^1$-G2:
In another embodiment the group R$^1$ is selected from the group R$^1$-G2 consisting of:
   H, —OH, C$_{1-2}$-alkyl, —O—(C$_{1-2}$-alkyl), —(CH$_2$)$_m$—COOH, —(CH$_2$)$_m$—C(=O)—O—(C$_{1-2}$-alkyl), —(CH$_2$)$_m$—C(=O)-heterocyclyl, —(CH$_2$)$_m$—C(=O)—NH$_2$, —(CH$_2$)$_m$—C(=O)—NH—(C$_{1-4}$-alkyl), —(CH$_2$)$_m$—C(=O)—N(C$_{1-2}$-alkyl)$_2$, —C(=O)—NH-cyclopropyl, —C(=O)—NH-heterocyclyl, —(CH$_2$)$_m$—NH—C(=O)—(C$_{1-2}$-alkyl) and -heterocyclyl,
   wherein each alkyl group or sub-group is optionally substituted with 1 to 3 F atoms or with one OH or —O—CH$_3$ group; and
   wherein each heterocyclyl is selected from the group consisting of azetidinyl, imidazolidinyl, tetrahydropyranyl and morpholinyl and is optionally substituted with one or two groups independently selected from the group consisting of OH, oxo, C$_{1-2}$-alkyl and —C(=O)—CH$_3$; and
   wherein m is 0 or 1; and
   wherein multiple R$^1$ may be identical or different, if n is 2.

R$^1$-G2a:
In another embodiment the group R$^1$ is selected from the group R$^1$-G2a consisting of:
   H, —OH, CH$_3$, —O—CH$_3$, —(CH$_2$)$_m$—COOH, —(CH$_2$)$_m$—C(=O)—O—CH$_3$, —(CH$_2$)$_m$—C(=O)-heterocyclyl, —(CH$_2$)$_m$—C(=O)—NH$_2$, —(CH$_2$)$_m$—C(=O)—NH—(C$_{1-3}$-alkyl), —(CH$_2$)$_m$—C(=O)—N(CH$_3$)$_2$, —C(=O)—NH-cyclopropyl, —C(=O)—NH-heterocyclyl, —(CH$_2$)$_m$—NH—C(=O)—CH$_3$ and -heterocyclyl,
   wherein each alkyl group or sub-group is optionally substituted with 1 to 3 F atoms or with one OH or —O—CH$_3$ group; and
   wherein each heterocyclyl is selected from the group consisting of azetidinyl, imidazolidinyl and tetrahydropyranyl, and is optionally substituted with one or two groups independently selected from the group consisting of OH, oxo, CH$_3$ and —C(=O)—CH$_3$;
   wherein m is 0 or 1; and
   wherein multiple R$^1$ may be identical or different, if n is 2.

R$^1$-G2b:
In another embodiment the group R$^1$ is selected from the group R$^1$-G2b consisting of:
   H, —OH, CH$_3$, CF$_3$, —O—CH$_3$, —(CH$_2$)$_m$—C(=O)—O—CH$_3$, —(CH$_2$)$_m$—C(=O)—NH$_2$, —C(=O)—NH—(C$_{1-2}$-alkyl) and —(CH$_2$)$_m$—C(=O)—N(CH$_3$)$_2$,
   wherein m is 0 or 1; and
   wherein multiple R$^1$ may be identical or different, if n is 2.

Groups R$^1$-G2, R$^1$-G2a and R$^1$-G2b are preferably combined with group A-G2.

If n is 2, the second R$^1$ group of R$^1$-G2, R$^1$-G2a or R$^1$-G2b is preferably selected from the group consisting of CH$_3$ and CF$_3$.

R$^1$-G3:
In another embodiment the group R$^1$ is selected from the group R$^1$-G3 consisting of:
   H, F, —OH, —O—(C$_{1-2}$-alkyl), —C(=O)-heterocyclyl, —(CH$_2$)$_m$—C(=O)—NH$_2$, —(CH$_2$)$_m$—C(=O)—NH—(C$_{1-4}$-alkyl), —(CH$_2$)$_m$—C(=O)—N(C$_{1-3}$-alkyl)$_2$, —(CH$_2$)$_m$—NH—C(=O)—(C$_{1-3}$-alkyl) and —N(C$_{1-3}$-alkyl)-C(=O)—(C$_{1-4}$-alkyl),
   wherein each alkyl group or sub-group is optionally substituted with 1 or more F atoms or with one OH or —O—(C$_{1-3}$-alkyl) group; and
   wherein m is 0 or 1; and
   wherein each heterocyclyl is selected from the group consisting of azetidinyl, piperidinyl, tetrahydropyranyl and morpholinyl and is optionally substituted with CH$_3$ group; and
   wherein multiple R$^1$ may be identical or different, if n is 2.

R$^1$-G3a:
In another embodiment the group R$^1$ is selected from the group R$^1$-G3a consisting of:
   H, —OH, —O—(C$_{1-2}$-alkyl), —C(=O)-morpholinyl, —C(=O)—NH$_2$, —C(=O)—NH—(C$_{1-4}$-alkyl), —C(=O)—N(C$_{1-3}$-alkyl)$_2$, —NH—C(=O)—(C$_{1-2}$-alkyl) and —N(CH$_3$)—C(=O)—(C$_{1-2}$-alkyl),
   wherein each alkyl group or sub-group is optionally substituted with 1 to 3 F atoms or with one OH or —O—CH$_3$ group; and
   wherein multiple R$^1$ may be identical or different, if n is 2.

R$^1$-G3b:
In another embodiment the group R$^1$ is selected from the group R$^1$-G3b consisting of:
   —OH, —C(=O)-morpholinyl, —C(=O)—NH$_2$, —C(=O)—NH—(C$_{1-4}$-alkyl), —C(=O)—N(CH$_3$)$_2$ and —NH—C(=O)—(CH$_3$),
   wherein multiple R$^1$ may be identical or different, if n is 2.

Groups R$^1$-G3, R$^1$-G3a and R$^1$-G3b are preferably combined with group A-G3.

If A is selected from A-G3, n is preferably 1.

R$^1$-G4:
In another embodiment the group R$^1$ is selected from the group R$^1$-G4 consisting of:
   H, —(CH$_2$)$_m$—COOH, —(CH$_2$)$_m$—C(=O)—O—(C$_{1-3}$-alkyl), —C(=O)-heterocyclyl, —(CH$_2$)$_m$—C(=O)—NH$_2$, —(CH$_2$)$_m$—C(=O)—NH—(C$_{1-3}$-alkyl) and —(CH$_2$)$_m$—C(=O)—N(C$_{1-3}$-alkyl)$_2$,
   wherein each alkyl group or sub-group is optionally substituted with 1 or more F atoms or with one OH or —O—CH$_3$ group; and
   wherein each heterocyclyl is selected from the group consisting of azetidinyl, piperidinyl, tetrahydropyranyl and morpholinyl and is optionally substituted with one CH$_3$ group; and
   wherein multiple R$^1$ may be identical or different, if n is 2.

R$^1$-G4a:
In another embodiment the group R$^1$ is selected from the group R$^1$-G4a consisting of:
   —COOH, —C(=O)—O—(C$_{1-2}$-alkyl), —C(=O)-morpholinyl, —C(=O)—NH$_2$, —C(=O)—NH—(C$_{1-2}$-alkyl) and —C(=O)—N(C$_{1-2}$-alkyl)$_2$,
   wherein each alkyl group or sub-group is optionally substituted with 1 to 3 F atoms; and
   wherein multiple R$^1$ may be identical or different, if n is 2.

$R^1$-G4b:

In another embodiment the group $R^1$ is selected from the group $R^1$-G4b consisting of:
—COOH, —C(=O)—O—CH$_3$, —C(=O)-morpholinyl and —C(=O)—NH—(CH$_3$).

Groups $R^1$-G4, $R^1$-G4a and $R^1$-G4b are preferably combined with group A-G4.

If A is selected from A-G4, n is preferably 1.

$R^1$-G5:

In one embodiment the group $R^1$ is selected from the group $R^1$-G5 consisting of:
H, F, —OH, $C_{1-4}$-alkyl, —O—($C_{1-4}$-alkyl), —C(=O)—NH$_2$, —C(=O)—NH—($C_{1-4}$-alkyl), —C(=O)—N($C_{1-4}$-alkyl)$_2$ and heterocyclyl,
wherein each alkyl group or sub-group is optionally substituted with 1 or more F atoms or with one OH or —O—($C_{1-3}$-alkyl) group; and
wherein each heterocyclyl is selected from the group consisting of azetidinyl, and piperidinyl, and is optionally substituted with one $C_{1-3}$-alkyl, —C(=O)—CH$_3$ or —C(=O)-cyclopropyl group; and
wherein multiple $R^1$ may be identical or different, if n is 2.

$R^1$-G5a:

In another embodiment the group $R^1$ is selected from the group $R^1$-G5a consisting of:
H, —OH, $C_{1-2}$-alkyl, —O—($C_{1-2}$-alkyl), —C(=O)—NH$_2$, —C(=O)—NH—($C_{1-2}$-alkyl), —C(=O)—N($C_{1-2}$-alkyl)$_2$ and piperidinyl,
wherein each alkyl group or sub-group is optionally substituted with 1 to 3 F atoms or with one OH group; and
wherein the piperidinyl group is optionally substituted with one —C(=O)—CH$_3$ or —C(=O)-cyclopropyl group; and
wherein multiple $R^1$ may be identical or different, if n is 2.

$R^1$-G5b:

In another embodiment the group $R^1$ is selected from the group $R^1$-G5b consisting of:
—OH, —CH$_3$, —O—CH$_3$, —C(=O)—NH$_2$, —C(=O)—N(CH$_3$)$_2$ and piperidinyl,
wherein the piperidinyl group is optionally substituted with one —C(=O)-cyclopropyl group; and
wherein multiple $R^1$ may be identical or different, if n is 2.

Groups $R^1$-G5, $R^1$-G5a and $R^1$-G5b are preferably combined with group A-G5.

If n is 2, the second $R^1$ group of $R^1$-G5, $R^1$-G5a or $R^1$-G5b is preferably selected from the group consisting of CH$_3$.

n

In one embodiment, n is an integer selected from 1 and 2.
Preferably, n is 1.
In another embodiment, n is 2.

m

In one embodiment, m is an integer selected from 0, 1 and 2.
Preferably, m is 0 or 1.
In another embodiment, m is 0.
In still another embodiment, m is 1.

The following preferred embodiments of compounds of formula I are described using generic formulae I.1 to I.4, wherein any tautomers, solvates, hydrates and salts thereof, in particular the pharmaceutically acceptable salts thereof, are encompassed.

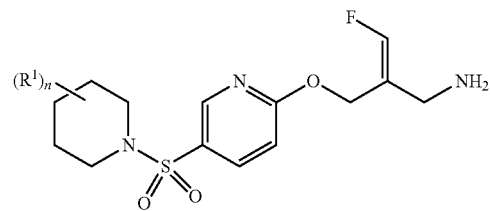

I.1

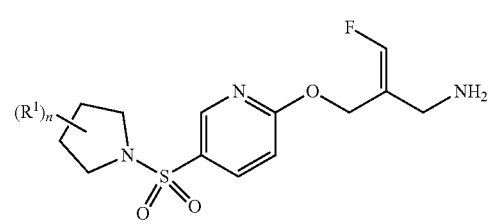

I.2

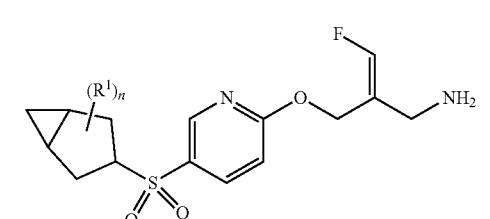

I.3

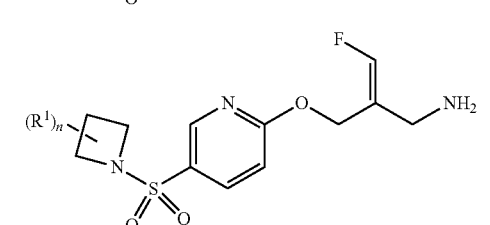

I.4

In of the above formulae (I.1) to (I.4), n and the group $R^1$ are as defined above. Examples of preferred subgeneric embodiments (E) according to the present invention are set forth in the following table, wherein each substituent group of each embodiment is defined according to the definitions set forth above:

| Embodiment | Formula | A | $R^1$ | n |
|---|---|---|---|---|
| E1 | I | A-G1 | $R^1$-G1 | 1 or 2 |
| E2 | I | A-G1 | $R^1$-G1 | 1 |
| E3 | I | A-G1 | $R^1$-G1a | 1 or 2 |
| E4 | I | A-G1 | $R^1$-G1a | 1 |
| E5 | I | A-G1 | $R^1$-G1b | 1 or 2 |
| E6 | I | A-G1 | $R^1$-G1b | 1 |
| E7 | I | A-G1 | $R^1$-G1c | 1 or 2 |
| E8 | I | A-G1 | $R^1$-G1c | 1 |
| E9 | I | A-G2 | $R^1$-G2 | 1 or 2 |
| E10 | I | A-G2 | $R^1$-G2 | 1 |
| E11 | I | A-G2 | $R^1$-G2a | 1 or 2 |
| E12 | I | A-G2 | $R^1$-G2a | 1 |
| E13 | I | A-G2 | $R^1$-G2b | 1 or 2 |
| E14 | I | A-G2 | $R^1$-G2b | 1 |
| E15 | I | A-G3 | $R^1$-G3 | 1 or 2 |
| E16 | I | A-G3 | $R^1$-G3 | 1 |
| E17 | I | A-G3 | $R^1$-G3a | 1 or 2 |
| E18 | I | A-G3 | $R^1$-G3a | 1 |
| E19 | I | A-G3 | $R^1$-G3b | 1 or 2 |
| E20 | I | A-G3 | $R^1$-G3b | 1 |
| E21 | I | A-G4 | $R^1$-G4 | 1 or 2 |
| E22 | I | A-G4 | $R^1$-G4 | 1 |
| E23 | I | A-G4 | $R^1$-G4a | 1 or 2 |
| E24 | I | A-G4 | $R^1$-G4a | 1 |

-continued

| Embodiment | Formula | A | R¹ | n |
|---|---|---|---|---|
| E25 | I | A-G4 | R¹-G4b | 1 |
| E26 | I | A-G5 | R¹-G5 | 1 or 2 |
| E27 | I | A-G5 | R¹-G5 | 1 |
| E28 | I | A-G5 | R¹-G5a | 1 or 2 |
| E29 | I | A-G5 | R¹-G5a | 1 |
| E30 | I | A-G5 | R¹-G5b | 1 or 2 |
| E31 | I | A-G5 | R¹-G5b | 1 |

Preferred compounds of the invention include:

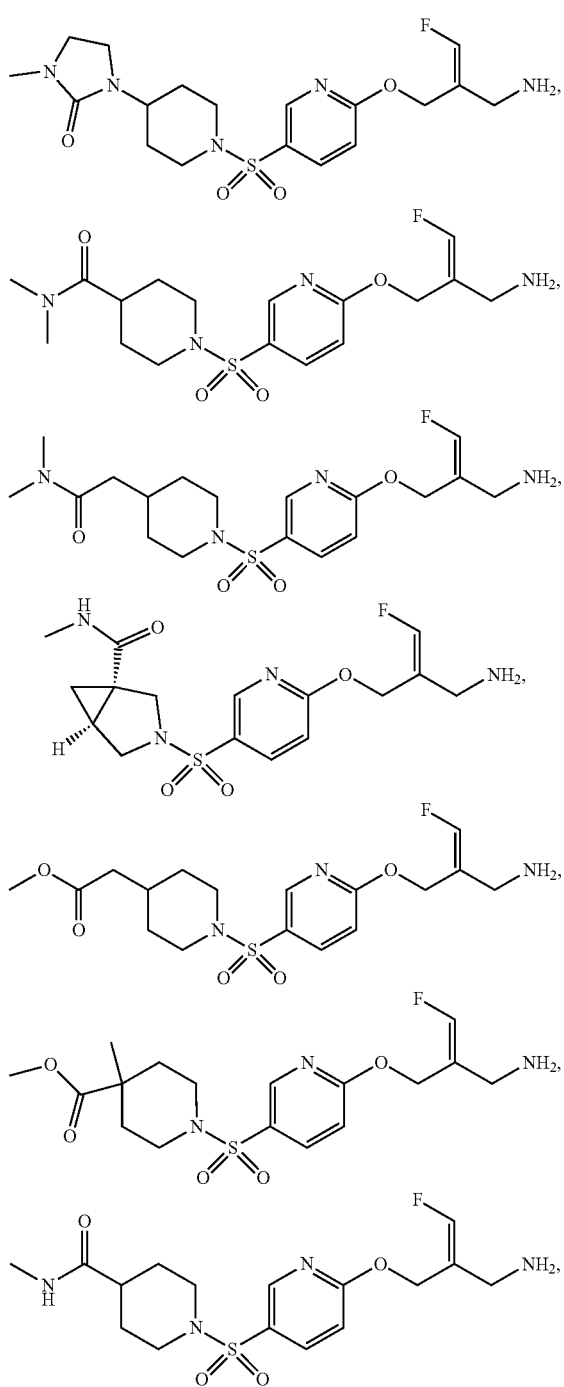

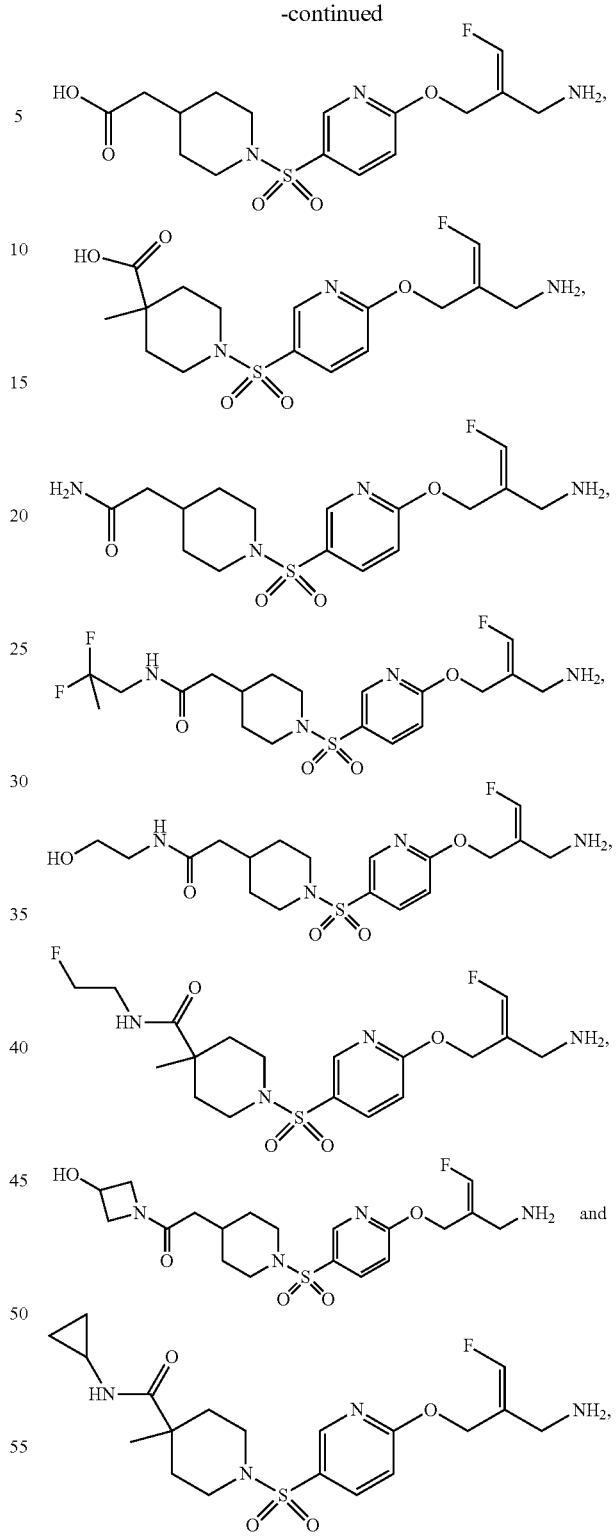

and the salts thereof, preferably the pharmaceutically acceptable salts thereof.

Particularly preferred compounds, including their tautomers and stereoisomers, the salts thereof, or any solvates or hydrates thereof, are described in the experimental section hereinafter.

The compounds according to the invention may be obtained using methods of synthesis which are known to the one skilled in the art and described in the literature of organic synthesis. Preferably, the compounds are obtained analogously to the methods of preparation explained more fully hereinafter, in particular as described in the experimental section.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof. Notwithstanding the above, the compounds of the invention are always Z-configured in the vinyl fluoride moiety.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of AOC3 with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

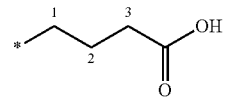

wherein the carboxy group is attached to the third carbon atom of the propyl group. The terms "1-methylpropyl-", "2,2-dimethylpropyl-" or "cyclopropylmethyl-" group represent the following groups:

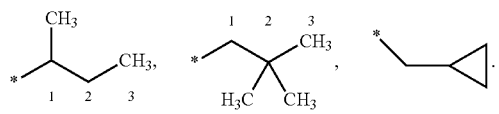

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound. Notwithstanding the above, the compounds of the invention are always Z-configured in the vinyl fluoride moiety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

Many of the terms given above may be used repeatedly in the definition of a formula or group and in each case have one of the meanings given above, independently of one another.

All rests and substituents as defined hereinbefore and hereinafter may be substituted with one or more F atoms.

Pharmacological Activity

The activity of the compounds of the invention may be demonstrated using the following assays:

AOC3 Biochemical Assay

The MAO-Glo™ Assay (commercially available from PROMEGA, #V1402) provides a sensitive method for the measurement of monoamine oxidase (MAO) activity (Valley, M. P. et al., 2006, Anal. Biochem. 359: 238-246) from a variety of tissues, biofluids or recombinant expressed or purified enzymes. As substrate a derivate of the beetle luciferin ((4S)-4,5-dihydro-2-(6-hydroxybenzothiazolyl)-4-thiazole-carboxylic acid) is used, which is oxidized at a primary amine moiety. After a spontaneous elimination and a catalyzed esterase reaction, the turnover of luciferin by the luciferase is recorded as a signal of AOC3 activity.

For the determination of AOC3 activity or compound inhibition potency, the compound inhibitors are dissolved in DMSO and adjusted to the respective assay concentration with reaction buffer (50 mM HEPES, 5 mM KCl, 2 mM $CaCl_2$, 1.4 mM $MgCl_2$, 120 mM NaCl, 0.001% (v/v) Tween 20, 100 µM TCEP, pH 7.4). An aliquot of 3 µL of the compound dilution is added to a 384 well plate (Optiplate, PS, flat bottom, white, PERKIN ELMER, #6007290) with a final DMSO concentration of 6.6%. Recombinant CHO cells, overexpressing the human (1500 cells/well), mouse (1000 cells/well) or rat (500 cells/well) AOC3 enzyme are diluted in reaction buffer and added in a volume of 15 µL to the wells. After incubation for 20 minutes at 37° C., 2 µL of MAO substrate (dissolved in DMSO at 16 mM, adjusted to assay concentration in reaction buffer to a final assay concentration of 20 µM) is added and further incubated for 60 minutes at 37° C. The turnover of the substrate is determined by the addition of 20 µL of the detection-mix which was generated by the addition of reconstitution buffer with esterase (PROMEGA, #V1402) to the luciferin detection reagent (PROMEGA, #V1402). After an incubation period of 20 minutes, the luminescent signal is measured with Envision 2104 Multilabel Reader (PERKIN ELMER).

Alternative assays for the determination of the AOC3 enzymatic activity could be the extraction of $^{14}$C-labelled benzylamine reaction product or the Amplex Red Monoamine Oxidase reaction (Molecular Probes, Netherlands) as described in Gella et al. (Gella, A. et al., 2013, J. Neural Transm. 120: 1015-1018).

The compounds of general formula (I) according to the invention for example have $IC_{50}$ values below 5000 nM, particularly below 1000 nM, preferably below 300 nM, most preferably below 100 nM.

AOC2 Biochemical Assay

The Amplex® Red Assay (commercially available from Thermo Fisher Scientific) provides a sensitive method for the detection of $H_2O_2$ generated during enzymatic reactions like the amine oxidation catalyzed by AOC2. The assay reagent is a colorless substrate (N-acetyl-3,7-dihydroxyphenoxazine) that reacts in a 1:1 stoichiometry with hydrogen peroxide ($H_2O_2$) to produce the fluorescent dye resorufin (7-hydroxyphenoxazin-3-one, excitation/emission maxima=570/585 nm). For the determination of AOC2 activity or compound AOC2 inhibition potency, the compound inhibitors are dissolved in DMSO and adjusted to the respective 20× assay concentration with reaction buffer (100 mM sodiumphosphate, 0.05% Pluronic F-127 (#P3000MP Sigma-Aldrich, pH 7.4). An aliquot of 5 µL of the compound dilution is added to a 96 well plate (flat bottom F, black, GREINER bio-one, #655900) in a DMSO concentration of 2%.

An AOC2 enzyme containing cell homogenate is generated by transient transfection of 6×106 HEK293 cells per flask (T75) with 9 µg pCMV-SPORT6-AOC2 (BC142641 rc, #pCS6(BC142641)-seq-TCHS1003-GVO-TRI, BioCat) in 750 µL of EMEM culture medium (#BE12-611F, Lonza) and 33.75 µl Attractene (#301005, Qiagen). Cells are cultured for 3 days in EMEM culture medium containing 10% FCS (#04-00-1A, Biological Industries). After washing twice with ice cold PBS, cells are lysed by mechanic homogenation and cleared supernatants are shock frozen in liquid nitrogen and stored at −80° C.

For the determination of AOC2 enzymatic activity cell lysates are thawed on ice and 1:1 diluted with reaction buffer. An Aliquot of 45 µL is added to the compound dilution and incubated for 30 min at 37° C. The enzymatic reaction is started with the addition of 50 µL of Amplex® Red reaction mix (final assay concentration: 100 mM sodiumphosphate, 120 µM Amplex® Red reagent (#A22177 Molecular Probes), 1.5 U/mL Horseradish Peroxidase (#P8375 Sigma-Aldrich), 2 mM phenylethylamine (#P6513-25G Sigma-Aldrich), 0.05% Pluronic F-127 (#P3000MP Sigma-Aldrich), pH 7.4, 37° C.).

The turnover per time of the substrate is determined directly with a fluorescence reader (Ex 540 nm/Em 590 nm) like Envision 2104 Multilabel Reader (PERKIN ELMER) for 60 min.
(cf. Anal Biochem (1997) 253:169-174; Anal Biochem (1997) 253:162-168)

AOC1 Biochemical Assay

The Amplex® Red Assay (available from Thermo Fisher Scientific) provides a sensitive method for the detection of $H_2O_2$ generated during enzymatic reactions like the amine oxidation catalyzed by AOC1. The assay reagent is a colorless substrate (N-acetyl-3,7-dihydroxyphenoxazine) that reacts in a 1:1 stoichiometry with hydrogen peroxide ($H_2O_2$) to produce the fluorescent dye resorufin (7-hydroxyphenoxazin-3-one, excitation/emission maxima=570/585 nm).

For the determination of AOC1 activity or compound AOC1 inhibition potency, the compound inhibitors are dissolved in DMSO and adjusted to the respective assay concentration with reaction buffer (100 mM sodiumphosphate, 0.05% Pluronic F-127 (#P3000MP Sigma-Aldrich), pH 7.4). An aliquot of 3 µL of the compound dilution is added to a 384 well plate (Optiplate, PS, flat bottom F, black, PERKIN ELMER, #6007270) in a DMSO concentration of 6.6%.

An AOC1 enzyme aliquot (#8297-AO-010, R&D Systems) is thawed on ice, diluted in reaction buffer and added in a volume of 7 µL to the wells to give a final assay concentration of 1 ng/well. After incubation of inhibitor and enzyme for 30 minutes at 37° C., the enzymatic reaction is started with the addition of 10 µL of Amplex® Red reaction mix (final assay concentration: 100 mM sodiumphosphate, 120 µM Amplex® Red reagent (#A22177 Molecular Probes), 1.5 U/mL Horseradish Peroxidase (#P8375 Sigma-Aldrich), 200 µM putrescine (#P7505 Sigma-Alrdich), 0.05% Pluronic F-127 (#P3000MP Sigma-Aldrich), pH 7.4, 37° C.).

After an incubation for 30 minutes at 37° C. the turnover of the substrate is determined directly (or after the addition of an excess of an amine-oxidase inhibitor) with a fluorescence reader (Ex 540 nm/Em 590 nm) like Envision 2104 Multilabel Reader (PERKIN ELMER).

MAO-A Biochemical Assay

The MAO-Glo™ Assay (commercially available from PROMEGA, #V1402) provides a sensitive method for the measurement of monoamine oxidase (MAO) activity (Valley, M. P. et al., 2006, Anal. Biochem. 359: 238-246) from a variety of tissues, biofluids or recombinant expressed or purified enzymes. As substrate a derivate of the beetle luciferin ((4S)-4,5-dihydro-2-(6-hydroxybenzothiazolyl)-4-thiazole-carboxylic acid) is used, which is oxidized at a primary amine moiety. After a spontaneous elimination and a catalyzed esterase reaction, the turnover of luciferin by the luciferase is recorded as a signal of MAO-A activity.

For the determination of MAO-A activity or MAO-A compound inhibition potency, the compound inhibitors are dissolved in DMSO and adjusted to the respective assay concentration with reaction buffer (HEPES 100 mM, Glycerol 5%, pH 7.5). An aliquot of 3 µL of the compound dilution is added to a 384 well plate (Optiplate, PS, flat bottom F, black, PERKIN ELMER, #6007270) in a DMSO concentration of 1.025%.

A MAO-A enzyme aliquot (M7316, Sigma-Aldrich) is thawed on ice, diluted in reaction buffer to 1.25 mU/µL and added in a volume of 5 µL to the wells. After incubation for 20 minutes at 37° C., 2 µL of MAO substrate (dissolved in DMSO at 16 mM, diluted to 20 µM in assay buffer to obtain a final assay concentration of 4 µM) is added, mixed, and the mixture further incubated for 60 minutes at 37° C.

The turnover of the substrate is determined by the addition of 10 µL of the Detection Reagent mix which was generated by the addition of reconstitution buffer with esterase (PROMEGA, #V1402) to the luciferin detection reagent (PROMEGA, #V1402). After an incubation period of 20 minutes at 37° C., the luminescent signal is measured with a fluorescence reader, e.g. Envision 2104 Multilabel Reader (PERKIN ELMER).

In the following table the activity expressed as $IC_{50}$ (nM) of compounds according to the invention is presented wherein the $IC_{50}$ values are determined in the AOC1, AOC2, AOC3 and MAO-A assays as described hereinbefore. The term "Example" refers to the example numbers according to the following experimental section.

Biological data of the compounds of the present invention as obtained in the AOC2, AOC3, AOC1 and MAO-A assays.

| Example | AOC3 $IC_{50}$ | AOC2 $IC_{50}$ | AOC1 $IC_{50}$ | MAO-A |
|---|---|---|---|---|
| 01 | 7 nM | 120 nM | 15265 nM | >50.0 µM |
| 02 | 40 nM | 272 nM | 8139 nM | >50.0 µM |
| 03 | 88 nM | 23.4 µM | 16373 nM | >50.0 µM |
| 04 | 23 nM | 394 nM | 3425 nM | >50.0 µM |
| 05 | 27 nM | 345 nM | 1217 nM | >50.0 µM |
| 06 | 16 nM | 285 nM | 678 nM | >50.0 µM |
| 07 | 4 nM | 272 nM | 1565 nM | >50.0 µM |
| 08 | 48 nM | 257 nM | 497 nM | >50.0 µM |
| 09 | 15 nM | 222 nM | 4553 nM | >50.0 µM |
| 10 | 22 nM | 214 nM | 3184 nM | >50.0 µM |
| 11 | 11 nM | 210 nM | 2550 nM | >50.0 µM |
| 12 | 15 nM | 209 nM | 3179 nM | >50.0 µM |
| 13 | 43 nM | 205 nM | 667 nM | >50.0 µM |
| 14 | 8 nM | 203 nM | 2149 nM | >50.0 µM |
| 15 | 9 nM | 202 nM | 4637 nM | >50.0 µM |
| 16 | 9 nM | 189 nM | 441 nM | 12.8 µM |
| 17 | 16 nM | 189 nM | 6251 nM | >50.0 µM |
| 18 | 50 nM | 176 nM | 1218 nM | >50.0 µM |
| 19 | 9 nM | 130 nM | 12510 nM | >50.0 µM |
| 20 | 6 nM | 119 nM | 1355 nM | >50.0 µM |
| 21 | 28 nM | 101 nM | 4092 nM | >50.0 µM |
| 22 | 35 nM | 93 nM | 13716 nM | >50.0 µM |
| 23 | 28 nM | 79 nM | >50000 nM | >50.0 µM |
| 24 | 20 nM | 72 nM | 1003 | >50.0 µM |
| 25 | 13 nM | 68 nM | 1322 | >50.0 µM |
| 26 | 9 nM | 63 nM | 911 | >50.0 µM |
| 27 | 5 nM | 62 nM | 1255 | >50.0 µM |
| 28 | 13 nM | 59 nM | 3743 nM | >50.0 µM |
| 29 | 8 nM | 58 nM | 1368 nM | >50.0 µM |
| 30 | 15 nM | 44 nM | 8895 nM | 21.4 µM |
| 31 | 4 nM | 40 nM | 869 nM | >50.0 µM |
| 32 | 4 nM | 39 nM | 5447 nM | 38.6 µM |
| 33 | 3 nM | nd | 1140 nM | 40.5 µM |
| 34 | 4 nM | 78 nM | 2396 nM | 15.2 µM |
| 35 | 3 nM | 277 nM | 1841 nM | >50.0 µM |
| 36 | 4 nM | 3 nM | 1379 nM | 13.5 µM |
| 37 | 10 nM | 193 nM | 9876 nM | >50.0 µM |
| 38 | 3 nM | 61 nM | 235 nM | 32.3 µM |
| 39 | 6 nM | 56 nM | 909 nM | >50.0 µM |
| 40 | 4 nM | 40 nM | 781 nM | >50.0 µM |
| 41 | 10 nM | 24 nM | 133 nM | >50.0 µM |

-continued

Biological data of the compounds of the present invention as obtained in the AOC2, AOC3, AOC1 and MAO-A assays.

| Example | AOC3 IC$_{50}$ | AOC2 IC$_{50}$ | AOC1 IC$_{50}$ | MAO-A |
|---|---|---|---|---|
| 42 | 6 nM | 9 nM | 2360 nM | 48.2 µM |
| 43 | 10 nM | 210 nM | 964 nM | 49.1 µM |
| 44 | 110 nM | 1 nM | >50000 nM | >50.0 µM |
| 45 | 67 nM | 70 nM | 37587 nM | >50.0 µM |
| 46 | 493 nM | 45 nM | >49988 nM | >50.0 µM |
| 47 | 548 nM | 5 nM | >49959 nM | >50.0 µM |
| 48 | 33 nM | 73 nM | 12993 nM | >50.0 µM |
| 49 | 8 nM | 21 nM | 553 nM | >50.0 µM |
| 50 | 8 nM | 16 nM | 5310 nM | 29.6 µM |
| 51 | 12 nM | nd | 10342 nM | 20.1 µM |
| 52 | 17 nM | nd | 15087 nM | 25.9 µM |
| 53 | 17 nM | nd | 14616 nM | >50.0 µM |
| 54 | 19 nM | nd | 10516 nM | 26.9 µM |
| 55 | 17 nM | nd | 27077 nM | >50.0 µM |
| 56 | 21 nM | nd | 11476 nM | >50.0 µM | nd = not determined.

According to AOC2 enzymatic tissue activity, the only human tissue with high AOC2-like activity is the retina and expression is associated to the retinal capillaries as shown by immune-histological studies. According to enzymatic function and localization of expression, AOC2 physiological function is reminiscent of the AOC3 homolog which is described as relevant for e.g. neurovascular, retinal inflammation and recruitment of immune cells (Matsuda et al. Invest Ophthalmol Vis Sci. 2017; 58(7):3254-3261, Noda et al FASEB J. 2008, 4:1094-103). Data on pharmacological inhibition or genetic depletion of AOC2 is not available so far. Nonetheless, it is expected that a combined inhibition of AOC2 and AOC3 increases anti-inflammatory potency in man for the treatment of ocular diseases as compared to AOC3 inhibition alone.

Therefore, it was an aim of the invention to provide compounds with a high activity on AOC3 and AOC2, in order to achieve the desired pharmacological effects.

Thus, the AOC2 activity was measured, and, surprisingly, it was found out that the pyridinyl sulfonamide compounds of the present invention exhibit an improved inhibition of AOC2 as compared to the closest analogs described in the prior art, e.g. in WO 2013/163675 and WO 2018/027892.

It has now been found out that, surprisingly, the compounds according to the present invention are more active inhibitors of AOC2 than the corresponding prior art compounds as described e.g. in WO 2013/163675 and WO 2018/027892; i.e., the replacement of a phenyl or pyrimidinyl moiety by a pyridinyl moiety and the introduction of azetidinyl-, pyrrolidinyl- or piperidinyl-sulfonylamides results in compounds with an improved inhibitory activity towards AOC2, without affecting the activity towards AOC3.

As it has a secondary amine substituent in the sulfonamide group, compound 10 of WO 2013/163675 represents the structurally closest comparison compound as compared to the presently claimed cyclic amines in the same position. Compound 10 of WO 2013/163675 contains a dimethylamino-sulfonamide moiety as compared to the cyclic azetidinyl-, pyrrolidinyl- or piperidinyl sulfonamides disclosed in the present invention. Additionally, Compound 10 of WO 2013/163675 contains a phenyl group whereas the compounds disclosed in the present invention contain a pyridinyl group. Compound 10 of WO 2013/163675 is a weak inhibitor of AOC2 (IC$_{50}$=538 nM, ca. 270-fold higher than IC$_{50}$ against AOC3). In comparison therewith, the compounds of the present invention show an improved inhibitory activity against AOC2 as exemplified by Examples 33 and 43 (each only ca. 20-fold less active against AOC2 as compared to AOC3) in the following table.

Moreover, reference compounds A and B that structurally differ from examples 33 and 43 of the present invention solely in phenyl versus pyridinyl group can be obtained in analogy to the syntheses described in WO 2013/163675. In comparison, the pyridinyl derivatives of the present invention show an increased inhibitory potency against AOC2. Reference compound A is 52-fold (ratio IC$_{50}$ AOC2/IC$_{50}$ AOC3) less active against AOC2 as compared to AOC3, while the pyridinyl analog Example 33 is only 18-fold less active against AOC2. Reference compound B is 58-fold less active against AOC2 as compared to AOC3, while the pyridinyl analog Example 43 is only 21-fold less active against AOC2.

The Z isomer of example 6 of WO 2018/027892 differs from example 43 in the pyrimidinyl versus pyridinyl group and in the lack of the sulfonyl group and inhibits AOC2 with an IC$_{50}$ of 2726 nM, whereas example 43 is a more potent inhibitor of AOC2 (IC$_{50}$=210 nM).

AOC1 expression and enzymatic activity is mainly found in the gut, placenta and kidney. The enzyme catalyzes the oxidation of primary amines derived from nutrition and protects the individuum from cardiometabolic effects of histamine, putrescine, tryptamine and cadaverine. Inhibition of AOC1 can lead to impaired tolerance to ingested histamine, resulting in increased plasma and tissue histamine-levels which can cause adverse events or undesirable side effects like decreased aterial pressure and compensation by increased heart-rate, tachycardia, headache, flush, urticaria, pruritus, bronchospasm and cardiac arrest (Maintz L. and Novak N. 2007. Am. J. Clin. Nutr. 85: 1185-96). The consequence of AOC1 inhibition in combination with histamine intake has been demonstrated in experiments with pigs: After the application of the AOC1-inhibitor aminoguanidine (100 mg/kg) and gavage of histamine (2 mg/kg) animals experienced increased histamine blood levels accompanied with a drop of blood pressure, increased heart rate, flushing, vomiting and death (3 out of 15 animals) (Sattler J. 1988. Agents and Actions, 23: 361-365) under the experimental conditions. Histamine intolerance in humans was associated to mutations in the promoter region of AOC1, leading to reduced mRNA expression and plasma AOC1 activity (Maintz et al. 2011. Allergy 66: 893-902).

Therefore, it was an aim of the invention to provide compounds with a low activity on AOC1, in order to avoid such undesired side-effects.

It has now been found out that, surprisingly, the compounds of the present invention exhibit increased selectivity towards AOC1 as compared to prior art compounds, particularly to the compounds disclosed in WO 2018/027892.

The Z isomer of example 6 of WO 2018/027892 inhibits AOC1 with an IC$_{50}$ of 70 nM, whereas the structurally similar example 43 of the present invention has an IC$_{50}$ of 964 nM, i.e. the compound of the present invention is factor 14 less active on AOC1 that the comparison compound, while the AOC3 potencies of both compounds are comparable.

MAO-A is a flavoenzyme which catalyzes the oxidation of primary amines such as the neurotransmitters dopamine, epinephrine, norepinephrine and serotonine. Based on this function, MAO-A is considered to be a key regulator for brain function and there is a link between low activity of MAO and several behavioral and neurological disorders (Shih, J. C. et al. 1999, Annu. Rev. Neurosci. 22: 197-217; Frazzetto G. et al. 2007, PLoS ONE 5: e486). Furthermore, MAO-A plays an important role in the pathogenesis of cardiovascular disorders (Gupta V et al, 2015, J. of Neurochemistry, 134: 21-38). MAO-A physiologically metabolizes tyramine and consequently protects humans from pathologically high levels of tyramine. Inhibition of MAO-A can lead to a hypertensive crisis if food and beverages high in tyramine are ingested (Sathyanarayana Rao, T. S. 2009, Indian J. of Psychiatry, 51: 65-66).

Therefore, it was an aim of the invention to provide compounds with a low activity on MAO-A, in order to avoid such undesired side-effects.

It has now been found out that, surprisingly, the compounds of the present invention exhibit increased selectivity towards MAO-A as compared to prior art compounds, particularly to the compounds disclosed in WO 2013/163675. As it is a secondary amine substituent in the sulfonamide group, compound 10 of WO 2013/163675 represents the structurally closest comparison compound as compared to the presently claimed cyclic amines in the same position. While compound 10 of WO 2013/163675 inhibits MAO-A with an $IC_{50}$ of 7408 nM, the compounds of the present invention typically inhibit MAO-A with an $IC_{50}$ of greater than 20000 nM, as exemplified by Examples 33 and 43 in the following table.

In comparison to reference compounds A and B that structurally differ from examples 33 and 43 of the present invention solely in the exchange of the claimed pyridinyl by a "state of the art-type" phenyl group, the pyridinyl derivatives of the present invention show an improved selectivity against MAO-A. While reference compound A and the pyridinyl analog Example 33 are similarly potent against AOC3, Example 33 shows a much lower inhibitory potency against MAO-A. Reference compounds B and the pyridinyl analog Example 43 are similarly potent against AOC3, however Example 43 shows a much lower inhibitory potency against MAO-A.

Comparison of biological data of certain compounds as obtained in the AOC3, AOC2, AOC1 and MAO-A assays as described above:

| Structure | $IC_{50}$ AOC3 | $IC_{50}$ AOC2 | $IC_{50}$ AOC1 | $IC_{50}$ MAO-A |
|---|---|---|---|---|
| 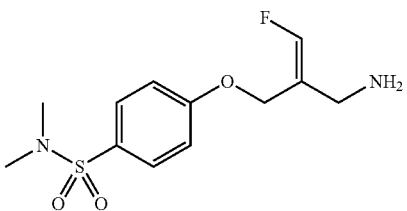  Compound 10 of WO 2013/163675 | 2 nM | 538 nM | 963 nM | 7408 nM |
| 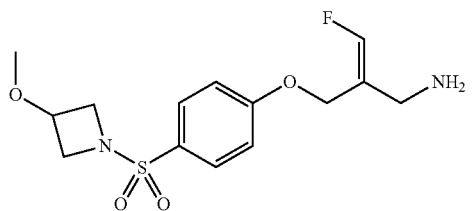  Reference compound A | 3 nM | 156 nM | 1746 nM | 2354 nM |
| 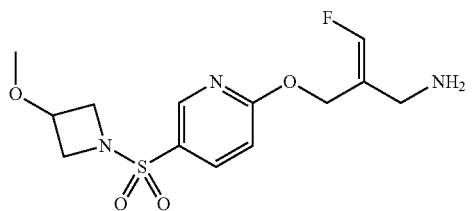  Example 33 | 3 nM | 55 nM | 1140 nM | 40521 nM |
| 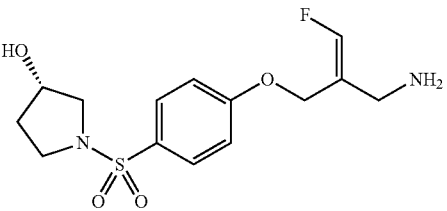  Reference compound B | 6 nM | 350 nM | 1214 nM | 7254 nM |

| Structure | IC$_{50}$ AOC3 | IC$_{50}$ AOC2 | IC$_{50}$ AOC1 | IC$_{50}$ MAO-A |
|---|---|---|---|---|
| 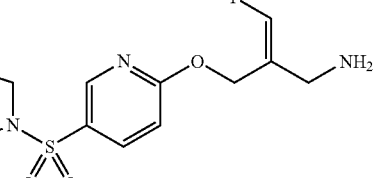 Example 43 | 10 nM | 210 nM | 964 nM | 49088 nM |
| 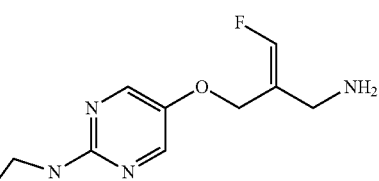 Z isomer of example 6 of WO 2018/027892 | 7 nM | 2726 nM | 70 nM | 56293 nM |
| 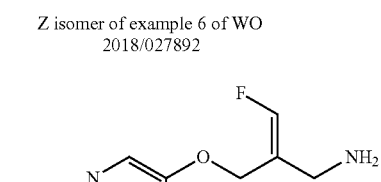 Example 1 of WO 2018/027892 | 4 nM | 3359 nM | 66 nM | 54935 nM |

In view of their ability to inhibit AOC3 and AOC2, the compounds of general formula (I) according to the invention and the corresponding salts thereof are suitable for the treatment, including preventative treatment of all those diseases or conditions which may be affected or which are mediated by the inhibition of AOC3 and AOC2 activity.

Further, compounds of the present invention show moderate to high in vitro efflux and/or a low intrinsic permeability in an MDCK p-GP assay. Therefore, compounds of the present invention are expected to exhibit a lower free concentration in the brain than in the blood (Liu, H. et al., 2018, Drug Discovery Today 23 (7): 1357-1372).

Accordingly, the present invention relates to a compound of general formula (I) as a medicament.

Furthermore, the present invention relates to the use of a compound of general formula (I) for the treatment and/or prevention of diseases or conditions which are mediated by the inhibition of AOC3 in a patient, preferably in a human.

In yet another aspect the present invention relates a method for treating, including preventing a disease or condition mediated by the inhibition of AOC3 in a mammal that includes the step of administering to a patient, preferably a human, in need of such treatment a therapeutically effective amount of a compound of the present invention, or a pharmaceutical composition thereof.

Diseases and conditions mediated by inhibitors of AOC3 embrace cancer, NASH (non-alcoholic steatohepatitis), pulmonary fibrosis, retinopathy, nephropathy and stroke, in particular hemorrhagic stroke.

According to one aspect the compounds of the present invention are particularly suitable for treating inflammatory diseases, such as vascular inflammatory diseases, arthritis, acute and chronic joint inflammation; eczema, such as atopic eczema, psoriasis ulcerative and rheumatoid psoriasis; pain, particularly musculoskeletal or nociceptive pain; inflammatory bowel disease, particularly non-infectious inflammatory bowel disease; multiple sclerosis; scleroderma, pulmonary diseases such as respiratory distress syndrome, asthma, pulmonary fibrosis, idiopathic pulmonary fibrosis (IPF), chronic obstructive pulmonary disease (COPD) and idiopathic inflammatory disease; nephropathy, diabetic proteinuria, kidney fibrosis; diabetic retinopathy or diabetic oedema such as macular diabetic oedema; cancer, particularly melanoma and lymphoma; hepatocellular carcinoma, unspecified Colitis, rheumatoid Crohn's disease Colitis; biliary tract diseases, primary biliary cholangitis, primary sclerosing cholangitis, non-alcoholic steatohepatitis (NASH), non-alcoholic fatty liver disease (NAFLD), alcoholic liver disease, liver fibrosis, liver cirrhosis; ulcerative reperfusion injury, cerebral ischaemia and transplant rejection.

According to another aspect the compounds of the present invention are particularly suitable for treating inflammatory diseases, such as vascular inflammatory diseases, arthritis and inflammatory bowel disease, particularly non-infectious inflammatory bowel disease; pulmonary fibrosis and idiopathic pulmonary fibrosis; diabetic retinopathy or diabetic oedema such as macular diabetic oedema; unspecified Colitis, rheumatoid Crohn's disease Colitis; biliary tract diseases, primary biliary cholangitis, primary sclerosing cholangitis, non-alcoholic steatohepatitis (NASH), non-alcoholic fatty liver disease (NAFLD), alcoholic liver disease, liver fibrosis, and liver cirrhosis.

The dose range of the compounds of general formula (I) applicable per day is usually from 0.001 to 10 mg per kg body weight of the patient, preferably from 0.01 to 8 mg per kg body weight of the patient. Each dosage unit may conveniently contain 0.1 to 1000 mg of the active substance, preferably it contains between 0.5 to 500 mg of the active substance.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon the patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent. According to one embodiment the additional therapeutic agent is selected from the group of therapeutic agents useful in the treatment of diseases or conditions associated with the metabolic syndrom, diabetes, obesity, cardiovascular diseases, cancer, NASH (non-alcoholic steatohepatitis), pulmonary fibrosis, retinopathy, nephropathy and/or stroke.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, anti-fibrotic agents, agents for the treatment of malignant tumors, antithrombotic agents, anti-angiogenesis agents, agents for the treatment of heart failure and agents for the treatment of complications caused by diabetes or associated with diabetes.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of AOC3, in particular diseases or conditions as described hereinbefore and hereinafter.

In yet another aspect the present invention relates a method for treating, including preventing a disease or condition mediated by the inhibition of AOC3 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Synthesis Schemes

Typical methods of preparing the compounds of the invention are described in the experimental section.

The potent inhibitory effect of the compounds of the invention can be determined by in vitro enzyme assays as described in the experimental section.

The compounds of the present invention may also be made by methods known in the art including those described below and including variations within the skill of the art.

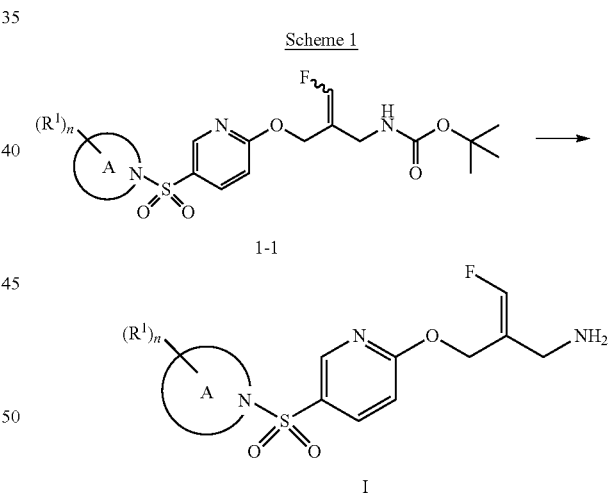

Scheme 1

Compounds of the general formula I, wherein A and R¹ are as previously defined, can be prepared via the process outlined in Scheme 1 using a compound of the general formula 1-1. Deprotection of the tert-Butoxycarbonyl (═BOC) group may be effected by treatment with an acid such as hydrochloric acid or trifluoroacetic acid in a suitable solvent such as methanol, dioxane or dichloromethane at a temperature between −20° C. and 100° C. If 1-1 is employed as a mixture of E/Z-isomers, the vinylfluorid E/Z-isomers of compounds of the general formula I may be separated by preparative HPLC or column chromatography on silica gel which affords compounds of the general formula I in isomerically pure form.

Scheme 2

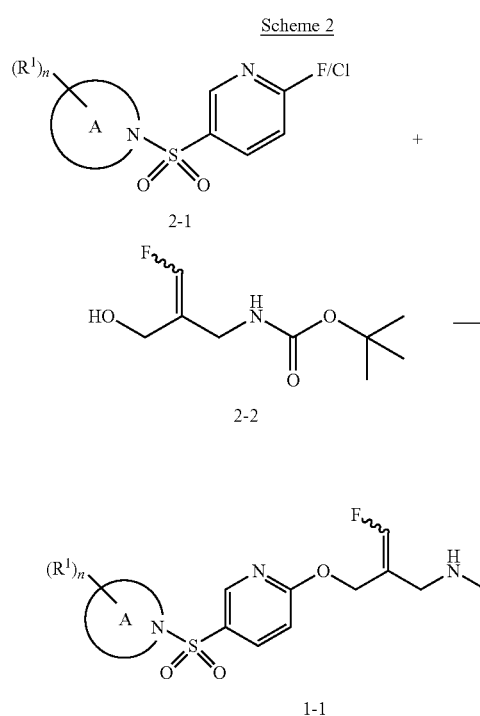

Intermediates of the general formula 1-1, wherein A and R¹ are as previously defined, can be prepared via the process outlined in Scheme 2 using a 6-fluoro or 6-chloro substituted pyridinyl sulfonamide compound of the general formula 2-1, wherein A and R¹ are as previously defined, and the alcohol 2-2 either as pure Z-isomer or as an E/Z-mixture, and a base such as sodium tert-butoxide or sodium hydride in an appropriate solvent such as THF, DMSO or toluene at a temperature between −20° C. and 100° C.

Scheme 3

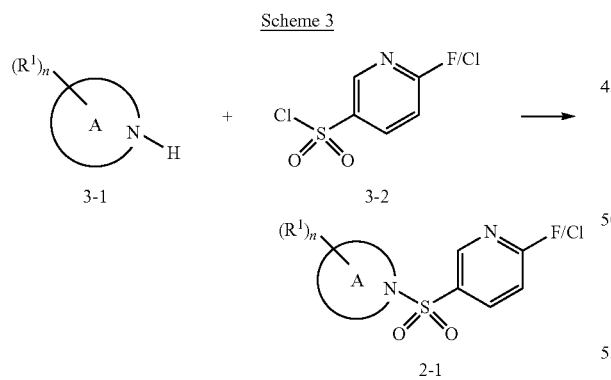

Intermediates of the general formula 2-1, wherein A and R¹ are as previously defined, can be prepared via the process outlined in Scheme 3 using an amine compound of the general formula 3-1, wherein A and R¹ are as previously defined, and 6-fluoro- or 6-chloropyridine-3-sulfonyl chloride, and a base such as triethylamine in an appropriate solvent such as dichloromethane, NMP, THF, DMSO or mixtures thereof at a temperature between −20° C. and 100° C.

Scheme 4

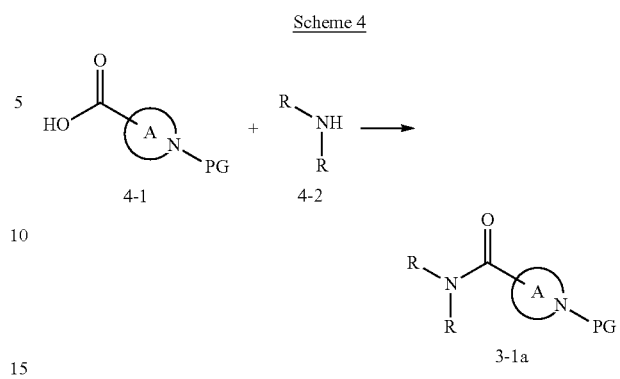

Intermediates of the general formula 3-1a, wherein the amine substituents R are selected as previously defined for amides among substituent R¹, can be prepared via the process outlined in Scheme 4 using a carboxylic acid of the general formula 4-1, a primary or secondary amine of the general formula 4-2, wherein the amine substituents R are selected as previously defined for amides among substituent R¹, an amide coupling reagent such as 1-propanephosphonic acid cyclic anhydride or HATU, and a base such as triethylamine or DIPEA in an appropriate solvent such as THF or DMF at a temperature between −20° C. and 100° C.

Scheme 5

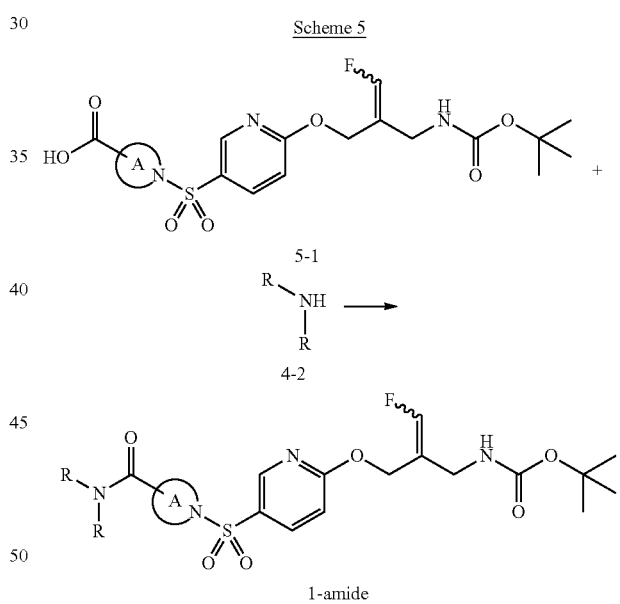

Compounds of the general formula 1-amide which exhibit an amide group according to the definitions for R¹, can also be prepared from carboxylic acids of the general formula 5-1, a primary or secondary amine of the general formula 4.2, wherein the amine substituents R are selected as previously defined for amides among substituent R¹, an amide coupling reagent such as 1-propanephosphonic acid cyclic anhydride, TCFH or HATU, and a base such as triethylamine or DIPEA in an appropriate solvent such as THF or DMF at a temperature between −20° C. and 100° C. Carboxylic acids of the general formula 5-1 are accessible from the corresponding alkyl esters through saponification with sodium or lithium hydroxide in a solvent such as methanol or THF at a temperature between −20° C. and 100° C. The synthetic routes presented may rely on the use of protecting groups. For example, reactive groups present, such as hydroxy, carbonyl, carboxy, amino, alkylamino or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before.

The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds.

Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physicochemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

EXPERIMENTAL PART

The Examples that follow are intended to illustrate the present invention without restricting it.
General Definitions
List of Abbreviations
  A Acid
  ACN Acetonitrile
  aq. Aqueous
  B Base
  BOC tert-Butoxycarbonyl
  ° C. Degree Celsius
  Cbz Benzyloxycarbonyl
  d Day
  DCM Dichloromethane
  DIPEA N,N-Diisopropylethylamine
  DMF N,N-Dimethylformamide
  DMSO Dimethylsulfoxide
  eq Equivalent
  ESI-MS Electrospray ionisation mass spectrometry
  EtOH Ethanol
  EtOAc Ethyl acetate
  Ex. Example
  exc. Excess
  g Gramm
  h Hour
  HATU N,N,N',N'-tetramethyl-O-(7-azabenzotriazol-1-yl) uronium hexafluorophosphate
  HPLC High performance liquid chromatography
  IBCF Isobutylchloroformate
  iPrOH Isopropyl alcohol
  M Molar (mol/L)
  MeOH Methanol
  min Minute
  mg milligramm
  mL Milliliter
  mmol Millimol
  MS Mass spectrometry
  MTBE 2-Methoxy-2-methylpropane
  N Normal=1 molar=1 mol/L
  NMP N-methyl-2-pyrrolidinone
  NMR Nuclear magnetic resonance
  Pd/C Palladium on carbon
  PE Petroleum ether
  psi Pound-force per square inch
  RP Reverse phase
  RT Room temperature (about 22° C.)
  $R_t$ Retention time
  S Solvent
  Sat. Saturated
  T Temperature
  t Time
  TBTU Benzotriazolyl-tetramethyluronium tetrafluoroborate
  TCFH Chloro-N,N,N',N'-tetramethylformamidinium hexafluorophosphate
  TEA Triethylamine
  TFA Trifluoroacetic acid
  THF Tetrahydrofuran
  THP Tetrahydropyran
  TLC Thin-layer chromatography
  Tol Toluene
General Methods Unless noted otherwise, all reactions are run at room temperature (about 22° C.), under inert atmosphere (e.g., Argon, $N_2$), and under anhydrous conditions. All compounds are characterized by at least one of the following methods: $^1H$ NMR, HPLC, HPLC-MS, or melting point.

Typically, reaction progress is monitored by thin layer chromatography (TLC) or HPLC-MS. Intermediates and products are purified using at least one of the following methods:

Recrystallization, column chromatography on silica gel or reversed phase HPLC using a C18 semi-preparative column eluting with a gradient of:
  ACN and $H_2O$+0.1% TFA
  ACN and $H_2O$+0.1% $NH_4OH$
Analytical Data The reported mass spectrometry (MS) data correspond to the observed mass signals (e.g., [M+H]$^+$). The HPLC methods used to characterize the compounds of the invention is described in the following tables HPLC-Methods

| Method | Mobile Phase A | Mobile Phase B | Gradient Time (min) | % A | % B | Flow (mL/min) | Column | Temperature |
|---|---|---|---|---|---|---|---|---|
| HPLC-1 | 0.1% TFA in water | ACN | 0.0 | 99.0 | 1.0 | 1.6 | XBridge BEH C18_2.1 × 30 mm_1.7 µm particle diameter | 60° C. |
| | | | 0.02 | 99.0 | 1.0 | 1.6 | | |
| | | | 1.0 | 0.0 | 100.0 | 1.6 | | |
| | | | 1.1 | 0.0 | 100.0 | 1.6 | | |

| Method | Mobile Phase A | Mobile Phase B | Gradient Time (min) | % A | % B | Flow (mL/min) | Column | Temperature |
|---|---|---|---|---|---|---|---|---|
| HPLC-2 | 0.1% TFA in water | ACN | 0.0 | 99.0 | 1.0 | 1.5 | Sunfire C18_2.1 × 30 mm_2.5 µm particle diameter | 60° C. |
| | | | 0.02 | 99.0 | 1.0 | 1.5 | | |
| | | | 1.0 | 0.0 | 100.0 | 1.5 | | |
| | | | 1.1 | 0.0 | 100.0 | 1.5 | | |

| Method | Mobile Phase A | Mobile Phase B | Gradient Time (min) | % A | % B | Flow (mL/min) | Column | Temperature |
|---|---|---|---|---|---|---|---|---|
| HPLC-3 | 0.1% $NH_3$ in water | ACN | 0.0 | 97.0 | 3.0 | 2.2 | XBridge C18_3.0 × 30 mm_2.5 µm particle diameter | 60° C. |
| | | | 0.2 | 97.0 | 3.0 | 2.2 | | |
| | | | 1.2 | 0.0 | 100.0 | 2.2 | | |
| | | | 1.25 | 0.0 | 100.0 | 3.0 | | |
| | | | 1.4 | 0.0 | 100.0 | 3.0 | | |

| Method | Mobile Phase A | Mobile Phase B | Gradient Time (min) | % A | % B | Flow (mL/min) | Column | Temperature |
|---|---|---|---|---|---|---|---|---|
| HPLC-4 | 0.1% TFA in water | ACN | 0.0 | 97.0 | 3.0 | 2.2 | XBridge C18_3.0 × 30 mm_2.5 µm particle diameter | 60° C. |
| | | | 0.2 | 97.0 | 3.0 | 2.2 | | |
| | | | 1.2 | 0.0 | 100.0 | 2.2 | | |
| | | | 1.25 | 0.0 | 100.0 | 3.0 | | |
| | | | 1.4 | 0.0 | 100.0 | 3.0 | | |

| Method | Mobile Phase A | Mobile Phase B | Gradient Time (min) | % A | % B | Flow (mL/min) | Column | Temperature |
|---|---|---|---|---|---|---|---|---|
| HPLC-5 | 0.1% TFA in water | ACN | 0.0 | 97.0 | 3.0 | 2.2 | Sunfire C18_3.0 × 30 mm_2.5 µm particle diameter | 60° C. |
| | | | 0.2 | 97.0 | 3.0 | 2.2 | | |
| | | | 1.2 | 0.0 | 100.0 | 2.2 | | |
| | | | 1.25 | 0.0 | 100.0 | 3.0 | | |
| | | | 1.4 | 0.0 | 100.0 | 3.0 | | |

| Method | Mobile Phase A | Mobile Phase B | Gradient Time (min) | % A | % B | Flow (mL/min) | Column | Temperature |
|---|---|---|---|---|---|---|---|---|
| HPLC-6 | 0.1% TFA in water | 0.08% TFA in ACN | 0.0<br>1.3<br>1.5<br>1.6 | 95.0<br>0.0<br>0.0<br>95.0 | 5.0<br>100.0<br>100.0<br>5.0 | 1.5<br>1.5<br>1.5<br>1.5 | Sunfire C18_3.0 × 30 mm_2.5 μm particle diameter | 60° C. |

| Method | Mobile Phase A | Mobile Phase B | Gradient Time (min) | % A | % B | Flow (mL/min) | Column | Temperature |
|---|---|---|---|---|---|---|---|---|
| HPLC-7 | 0.1% NH₃ in water | ACN | 0.0<br>1.3<br>1.5<br>1.6 | 95.0<br>0.0<br>0.0<br>95.0 | 5.0<br>100.0<br>100.0<br>5.0 | 1.5<br>1.5<br>1.5<br>1.5 | XBridge C18_3.0 × 30 mm_2.5 μm particle diameter | 60° C. |

| Method | Mobile Phase A | Mobile Phase B | Gradient Time (min) | % A | % B | Flow (mL/min) | Column | Temperature |
|---|---|---|---|---|---|---|---|---|
| HPLC-8 | 0.1% TFA in water | 0.08% TFA in ACN | 0.0<br>1.3<br>1.5<br>1.6 | 95.0<br>0.0<br>0.0<br>95.0 | 5.0<br>100.0<br>100.0<br>5.0 | 1.5<br>1.5<br>1.5<br>1.5 | Sunfire C18_3.0 × 30 mm_2.5 μm particle diameter | 60° C. |

| Method | Mobile Phase A | Mobile Phase B | Gradient Time (min) | % A | % B | Flow (mL/min) | Column | Temperature |
|---|---|---|---|---|---|---|---|---|
| HPLC-9 | 0.1% TFA in water | ACN | 0.0<br>0.15<br>2.15<br>2.2<br>2.4 | 97.0<br>97.0<br>0.0<br>0.0<br>0.0 | 3.0<br>3.0<br>100.0<br>100.0<br>100.0 | 4.0<br>3.0<br>3.0<br>4.5<br>4.5 | Sunfire C18_3.0 × 30 mm_2.5 μm particle diameter | 60° C. |

Synthetic Intermediates/Examples

The intermediates and examples which follow are illustrative and, as recognized by one skilled in the art, particular reagents or conditions could be modified as needed for individual compounds without undue experimentation.

The compounds of the invention may be prepared by the general methods and examples presented below and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the synthetic section. Undescribed intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

Intermediate I.1: (S)-Pyrrolidine-3-carboxylic acid [2-methyl-2-(tetrahydro-pyran-2-yloxy)-propyl]-amide Amide-Coupling:

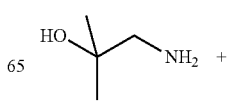

THP Protection:

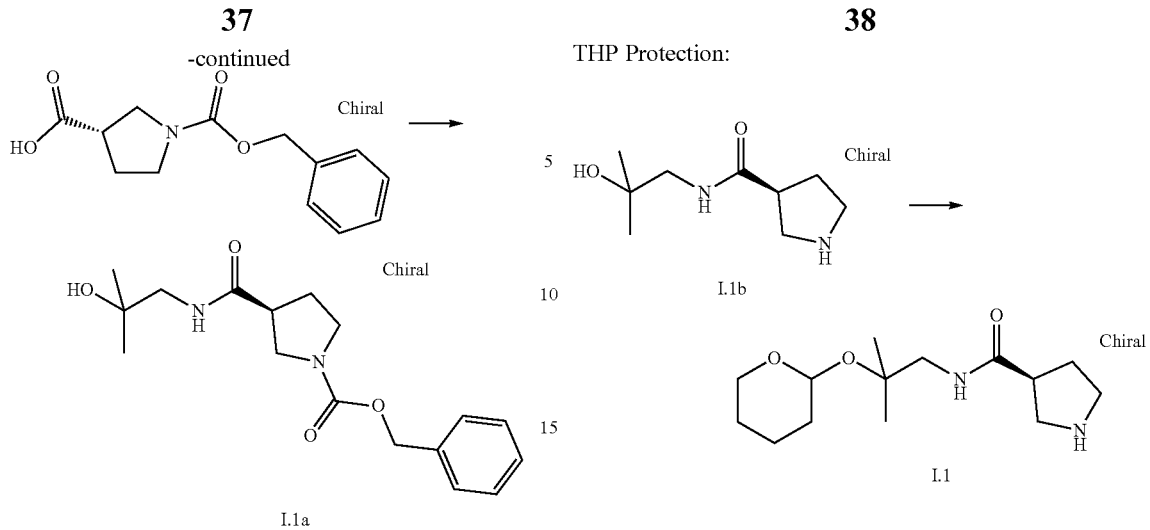

Intermediate I.1b (1.47 g; 7.89 mmol) was diluted with 3,4-dihydro-2H-pyrane (10.00 mL; 108.28 mmol) and p-toluenesulfonic acid monohydrate (0.15 g; 0.79 mmol) was added. The reaction mixture was stirred at RT for three days and concentrated in vacuo to obtain the crude intermediate I.1.

Yield: 2.54 g (99%), ESI-MS: m/z=271 [M+H]$^+$, R$^t$(HPLC): 0.75 min (HPLC-3)

Intermediate I.2: (S)-Pyrrolidine-3-carboxylic acid dimethylamide hydrochloride

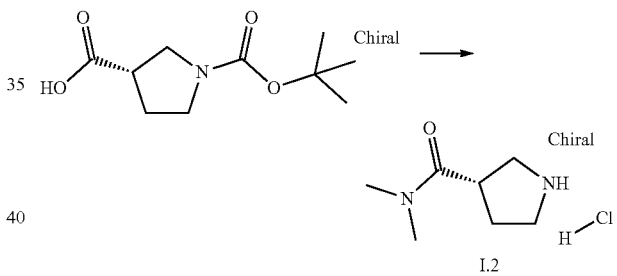

Step 1—Amide-coupling: (S)-Pyrrolidine-1,3-dicarboxylic acid 1-tert-butyl ester (0.5 g, 2.32 mmol) was dissolved in THF (5.00 mL) and TEA (2.61 mL; 18.58 mmol) and a solution of dimethylamine in THF (2 M; 2.32 mL; 4.65 mmol) was added. To the reaction mixture was added a solution of 1-propanephosphonic acid cyclic anhydride (50% in THF; 2.71 mL; 4.65 mmol) at RT. The reaction mixture was stirred at RT and diluted with 4 N aq. sodium hydroxide. The aq. phase was extracted with MTBE twice and the organic phase was dried with Na$_2$SO$_4$, filtered and concentrated in vacuo. Step 2—BOC deprotection: The crude material of step 1 was diluted with MeOH (20 mL) and treated with 4 N HCl in 1,4-dioxane (5 mL; 20.00 mmol) at RT. The reaction mixture was stirred at RT overnight. The reaction mixture was concentrated in vacuo to provide intermediate I.2.

Yield: 442 mg (85%), ESI-MS: m/z=143 [M+H]$^+$, R$_t$(HPLC): 0.12 min (HPLC-5)

The following intermediate was prepared in analogy to the above described procedure using the corresponding starting materials. For changes from this procedure, see "synthesis comment".

(S)-Pyrrolidine-1,3-dicarboxylic acid-1-benzylester (2.00 g; 8.02 mmol) was dissolved in THF (20.00 mL) and TEA (9.01 mL; 64.19 mmol) and 1-amino-2-methylpropan-2-ol (0.83 g; 8.83 mmol) was added. The reaction mixture was cooled to 0° C. and a solution of 1-propanephosphonic acid cyclic anhydride (50% in THF; 7.03 ml; 12.04 mmol) was added. It was stirred at RT for 3 h. The reaction mixture was diluted with aq. 4 N NaOH (20 mL) and extracted with MTBE (30 mL) twice. The pooled organic phases were dried and evaporated to give the crude intermediate I.1a.

Yield: 2.51 g (98%), ESI-MS: m/z=321 [M+H]+, R$_t$(HPLC): 0.90 min (HPLC-5)

Cbz Deprotection:

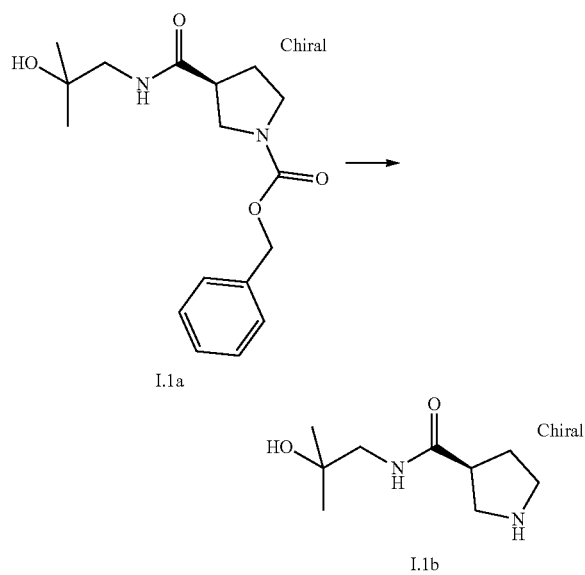

A mixture of intermediate I.1a (2.51 g; 7.83 mmol) and 10% Pd/C (0.25 g) in MeOH (50 mL) was treated with hydrogen (50 psi) at RT overnight. The reaction mixture was filtered, washed with MeOH and concentrated in vacuo to provide the crude intermediate I.1b.

Yield: 1.47 g (99%), ESI-MS: m/z=187 [M+H]+, R$_t$(HPLC): 0.12 min (HPLC-5)

| intermediate | structure | starting materials | $R_t$ [min] (HPLC method) | MS | synthesis comment |
|---|---|---|---|---|---|
| I.3 | 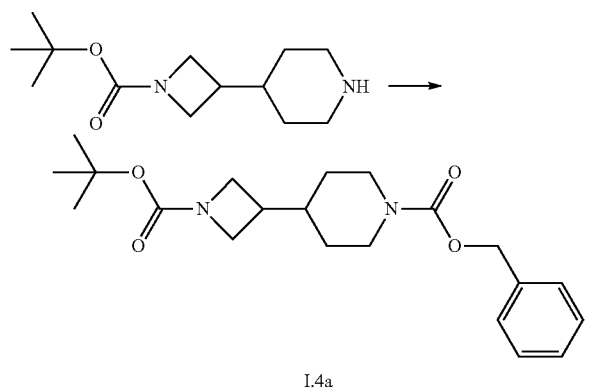 | 2M methyl-amine in THF | 0.11 (HPLC-5) | 141 | Step 1: 50 min Step 2: 4.6 eq HCl |

I.4: 1-(3-Piperidin-4-yl-azetidin-1-yl)-ethanone

Cbz Protection:

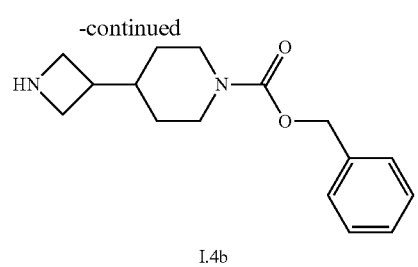

I.4a

3-Piperidine-4-yl-azetidine-1-carboxylic acid tert-butyl ester (500 mg; 2.08 mmol) was dissolved in DCM (10 mg), treated with TEA (348 μL; 2.50 mmol) and cooled to 0° C. To the reaction mixture was added benzyl chloroformate (322 μL; 2.29 mmol) dropwise and afterwards, the reaction mixture was warmed to RT. The reaction mixture was stirred at RT overnight, diluted with DCM and extracted with water twice. The organic phase was dried and concentrated in vacuo. The crude material was purified by silica gel chromatography to provide intermediate I.4a.

Yield: 220 mg (28%), ESI-MS: m/z=375 [M+H]$^+$, $R_t$ (HPLC): 0.81 min (HPLC-2)

BOC Deprotection:

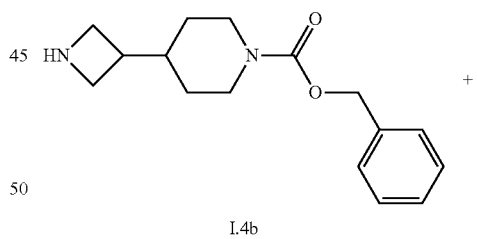

I.4a

-continued

I.4b

To a solution of intermediate I.4a (220 mg; 0.59 mmol) in DCM (3 mL), TFA (453 μL; 5.87 mmol) was added. The Reaction mixture was stirred at RT overnight, the solvent was evaporated under reduced pressure and the residue was washed once with water and once with aq. solution of NaHCO$_3$. The organic phase was dried and concentrated in vacuo to give the crude intermediate I.4b.

Yield: 170 mg (100%), ESI-MS: m/z=275 [M+H]$^+$, $R_t$ (HPLC): 0.43 min (HPLC-2)

Acetylation:

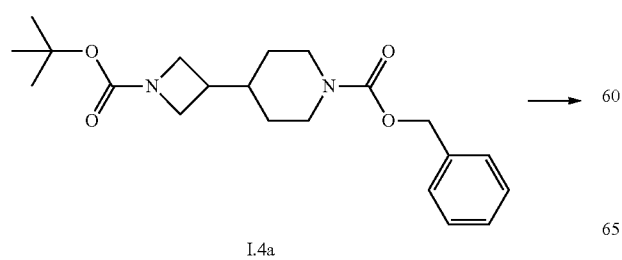

I.4c

Intermediate I.4b (170 mg; 0.62 mmol) was dissolved in DCM (3.00 mL) and treated with TEA (258 μL; 1.86 mmol).

The solution was cooled to 0° C. and acetyl chloride (53 µL; 0.74 mmol) was added dropwise. The reaction mixture was stirred at 0° C. for 10 min, warmed to RT and stirred at RT overnight. The reaction mixture was washed with water twice. The organic phase was dried and concentrated in vacuo to provide the crude intermediate I.4c.

Yield: 190 mg (97%), ESI-MS: m/z=317 [M+H]⁺, R$_t$ (HPLC): 0.60 min (HPLC-2)

Cbz Deprotection:

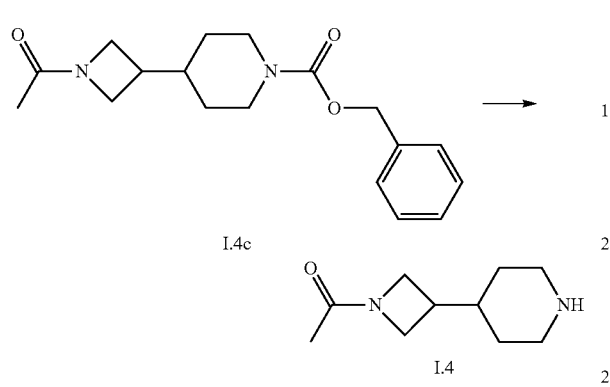

A mixture of intermediate I.4c (190 mg; 0.60 mmol) and 10% Pd/C (50 mg) in MeOH (5 mL) was treated with hydrogen (50 psi) at RT overnight. The reaction mixture was filtered and concentrated in vacuo to provide the crude intermediate I.4.

Yield: 90 mg (82%), ESI-MS: m/z=183 [M+H]+

Intermediate I.5: (R)-Pyrrolidine-3-carboxylic acid methylamide hydrochloride

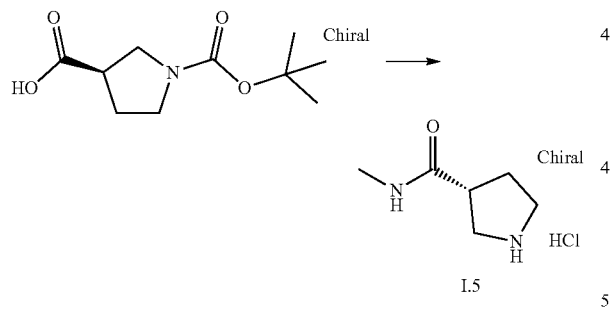

Step 1—Amide-coupling: (R)-Pyrrolidine-1,3-dicarboxylic acid 1-tert-butyl ester (800 mg, 3.61 mmol) was dissolved in THF (5.00 mL) and TEA (4.05 mL; 28.84 mmol) and a solution of methylamine in THF (2 M; 3.61 mL; 7.21 mmol) was added. To the reaction mixture was added a solution of 1-propanephosphonic acid cyclic anhydride (50% in THF; 4.21 mL; 7.21 mmol) at RT. The reaction mixture was stirred at RT for 1 h and diluted with 4 N aq. sodium hydroxide (20 mL). The aq. phase was extracted with MTBE (2×20 mL) and the pooled organic phases were washed with brine, dried, filtered and concentrated in vacuo.

Step 2—BOC deprotection: The crude material of step 1 was diluted with EtOAc (20 mL) and treated with 4 N HCl in 1,4-dioxane (2 mL; 8.00 mmol) at RT. The reaction mixture was stirred at RT overnight. The reaction mixture was concentrated in vacuo to provide intermediate I.5.

Yield: 755 mg (99%), ESI-MS: m/z=129 [M+H]⁺, R$_t$ (HPLC): 0.12 min (HPLC-5)

I.6: N,N-Dimethyl-2-piperidin-4-yl-acetamide trifluoroacetate

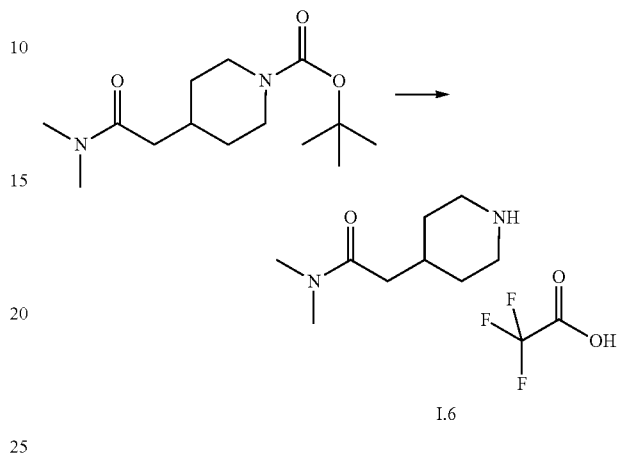

4-Dimethylcarbamoylmethyl-piperidine1-carboxylic acid tert-butyl ester (2.20 g; 8.14 mmol) and DCM (300 mL) were cooled to 0° C. and TFA (25 mL) was added. The reaction mixture was stirred at 0° C. for 3 h, evaporated under reduced pressure and the residue was suspended with diisopropyl ether. The remaining solid was filtered to give intermediate I.6.

Yield: 2.29 g (99%)

I.7: Morpholin-4-yl-(S)-pyrrolidin-3-yl-methanone

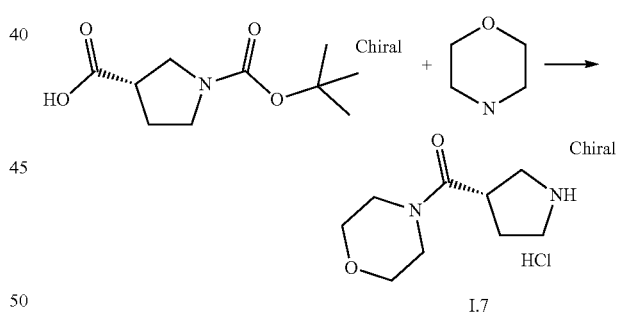

Step 1—Amide-coupling: (S)-Pyrrolidine-1,3-dicarboxylic acid 1-tert-buytl ester (500 mg, 2.32 mmol) was dissolved in THF (4.50 mL) and TEA (2.61 mL; 18.58 mmol) and a solution of morpholine (220 mg; 2.56 mmol) in THF (0.5 mL) was added. To the reaction mixture was added a solution of 1-propanephosphonic acid cyclic anhydride (50% in THF; 2.71 mL; 4.65 mmol) at RT. The reaction mixture was stirred at RT for 3 h and diluted with 4 N aq. sodium hydroxide (20 mL). The aq. phase was extracted with MTBE (2×20 mL) and the pooled organic phases were washed with brine, dried with Na$_2$SO$_4$, filtered and concentrated in vacuo.

Step 2—BOC deprotection: The crude material of step 1 was diluted with MeOH (20 mL) and treated with 4 N HCl in 1,4-dioxane (5 mL; 20.00 mmol) at RT. The reaction mixture was stirred at RT overnight. The reaction mixture was concentrated in vacuo and co-evaporated with toluene (50 mL) to provide intermediate I.7.

Yield: 527 mg (82%), ESI-MS: m/z=185 [M+H]$^+$, R$_t$ (HPLC): 0.12 min (HPLC-5)

Intermediate I.8: racemic cis-3-Aza-bicyclo[3.1.0]hex-1-yl-morpholin-4-yl-methanone hydrochloride Amide-Coupling:

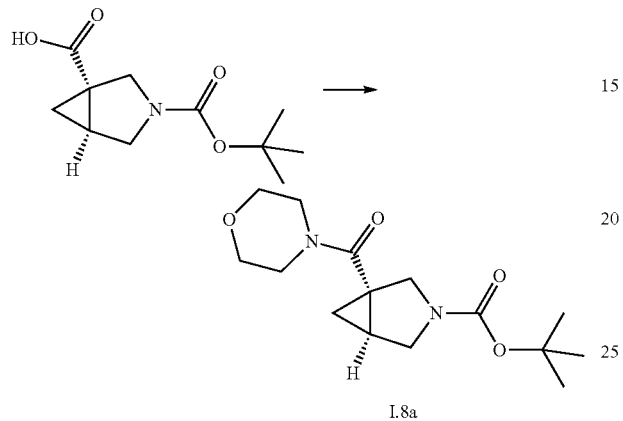

I.8a

Racemic cis-3-aza-bicyclo[3.1.0]hexane-1,3-dicarboxylic acid-3-tert-butyl ester (1.00 g; 4.40 mmol) and HATU (1.90 g; 4.84 mmol) were suspended in DMF und DIPEA (1.89 mL; 11.00 mmol) was added. The reaction mixture was stirred at RT for 30 min. To the reaction mixture was added morpholine (0.77 mL; 8.80 mmol) and the solution was stirred at RT overnight. The reaction mixture was diluted with water (20 mL) and extracted with DCM (3×20 mL). The pooled organic phases were washed with aq. 1 N NaOH (20 mL), dried and concentrated in vacuo. The crude material was purified by RP-HPLC (C18, 50° C., ACN+0.1% TFA in water) to obtain intermediate I.8a.

Yield: 1.17 g (90%), ESI-MS: m/z=241 [M+H]$^+$, R$_t$ (HPLC): 0.90 min (HPLC-5)

BOC Deprotection:

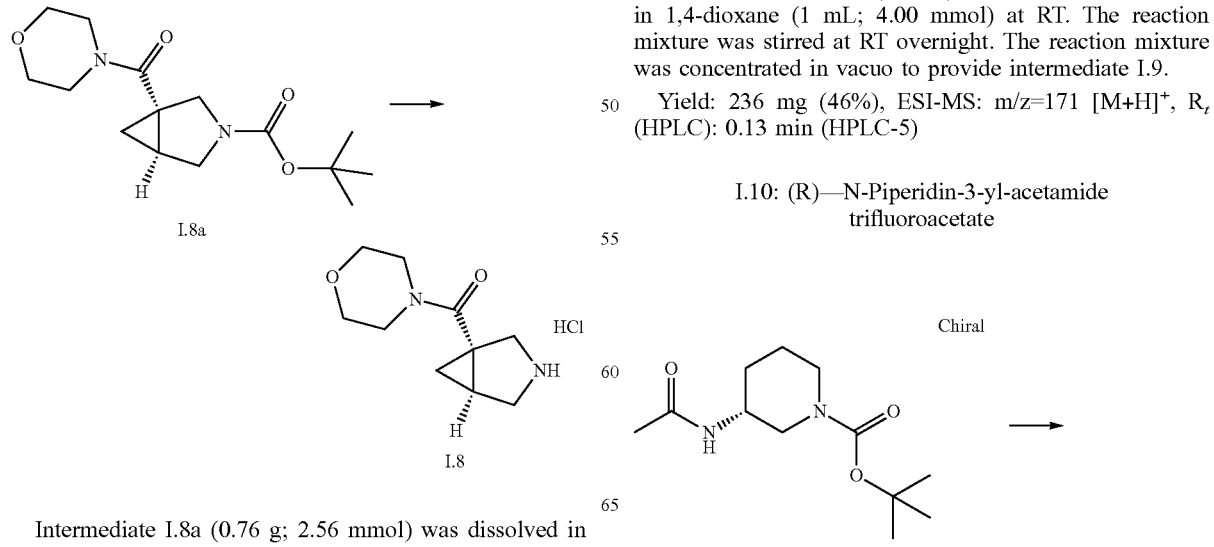

Intermediate I.8a (0.76 g; 2.56 mmol) was dissolved in MeOH (2.00 mL) and hydrogen chloride (4 N in 1,4-dioxane; 5.00 mL; 20.00 mmol) was added. The reaction mixture was stirred at RT overnight. The reaction mixture was diluted with MTBE, the precipitate was filtered and washed with MTBE. The solvent was allowed to evaporate in order to obtain intermediate I.8 as a dry solid.

Yield: 0.53 g (89%), ESI-MS: m/z=197 [M+H]$^+$, R$_t$ (HPLC): 0.20 min (HPLC-1)

I.9: Morpholin-4-yl-(S)-pyrrolidin-3-yl-methanone

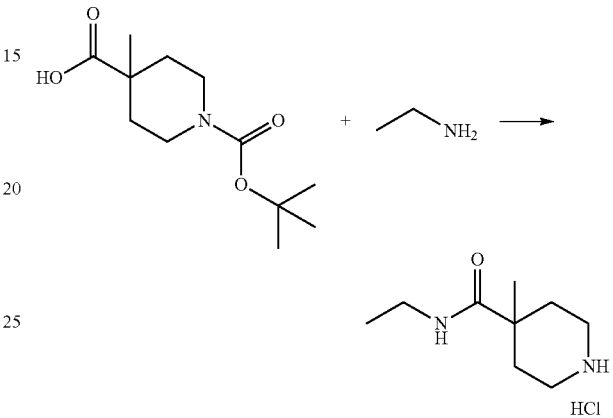

I.9

Step 1—Amide-coupling: 4-Methyl-piperidine-1,4-dicarboxylic acid mono-tert-butyl ester (500 mg, 1.99 mmol) was dissolved in THF (5 mL) and TEA (2.24 mL; 15.95 mmol) and a solution of ethylamine in THF (2 M; 1.99 mL; 3.99 mmol) was added. To the reaction mixture was added a solution of 1-propanephosphonic acid cyclic anhydride (50% in THF; 2.33 mL; 3.99 mmol) at RT. The reaction mixture was stirred at RT for 1 h and diluted with 4 N aq. sodium hydroxide (20 mL). The aq. phase was extracted with MTBE (2×20 mL) and the pooled organic phases were washed with brine (20 mL), dried, filtered and concentrated in vacuo.

Step 2—BOC deprotection: The crude material of step 1 was diluted with EtOAc (20 mL) and treated with 4 N HCl in 1,4-dioxane (1 mL; 4.00 mmol) at RT. The reaction mixture was stirred at RT overnight. The reaction mixture was concentrated in vacuo to provide intermediate I.9.

Yield: 236 mg (46%), ESI-MS: m/z=171 [M+H]$^+$, R$_t$ (HPLC): 0.13 min (HPLC-5)

I.10: (R)—N-Piperidin-3-yl-acetamide trifluoroacetate

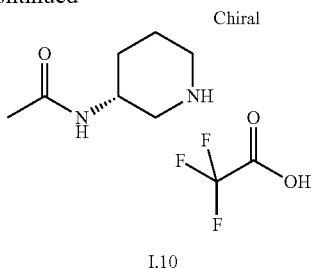

I.10

(R)-3-Acetylamino-piperidine-1-carboxylic acid tert-butyl ester (3.20 g; 13.21 mmol), TFA (10.18 mL; 132.10 mmol) and DCM (300 mL) were stirred at RT, evaporated under reduced pressure, and finally co-evaporated with EtOH to give intermediate I.10.

Yield: 2.29 g (99%), ESI-MS: m/z=143 [M+H]$^+$

I.11: (4-Azetidin-3-yl-piperidin-1-yl)-cyclopropyl-methanone

Acylation:

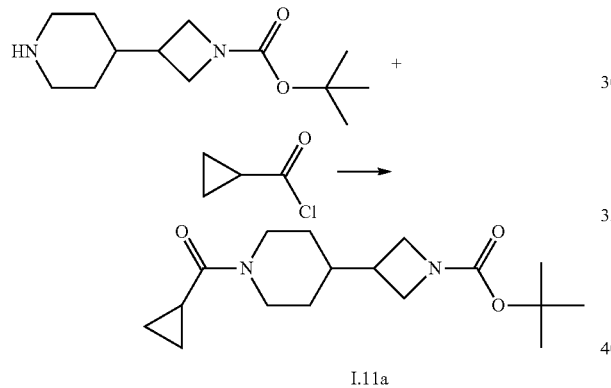

I.11a

3-Piperidin-4-yl-azetidine-1-carboxylic acid tert-butyl ester (530 mg; 2.21 mmol) was dissolved in DCM (20 mL) and TEA (0.71 mL; 5.07 mmol) was added. The solution was cooled with an ice bath and cyclopropanecarbonyl chloride (300 mg; 2.87 mmol) dissolved in DCM (1 mL) was added. The reaction mixture was stirred at 0° C. for 1 h and stirred at 15° C. for 3 d. The reaction mixture was diluted with DCM and washed with sat. aq. NaHCO$_3$-solution once, two times with aq. 0.5 N HCl-solution and once with brine. The organic phase was dried over Na$_2$SO$_4$ and concentrated in vacuo to give intermediate I.11a.

Yield: 690 mg (91%), ESI-MS: m/z=309 [M+H]$^+$, R$_t$ (HPLC): 0.64 min (HPLC-2)

BOC Deprotection:

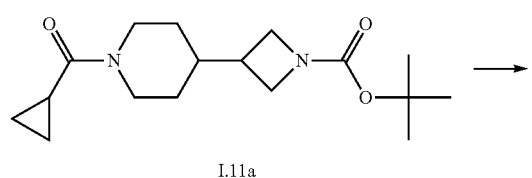

I.11a

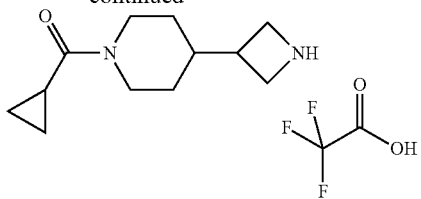

I.11

Intermediate I.11a (690 mg; 3.01 mmol), TFA (0.62 mL; 8.05 mmol) and DCM (20 mL) were stirred at RT overnight and evaporated to give intermediate I.11.

Yield: 500 mg (77%), ESI-MS: m/z=209 [M+H]$^+$, R$_t$ (HPLC): 0.26 min (HPLC-2)

I.12: trans-3-Aza-bicyclo[3.1.0]hexane-6-carboxylic acid methylamide

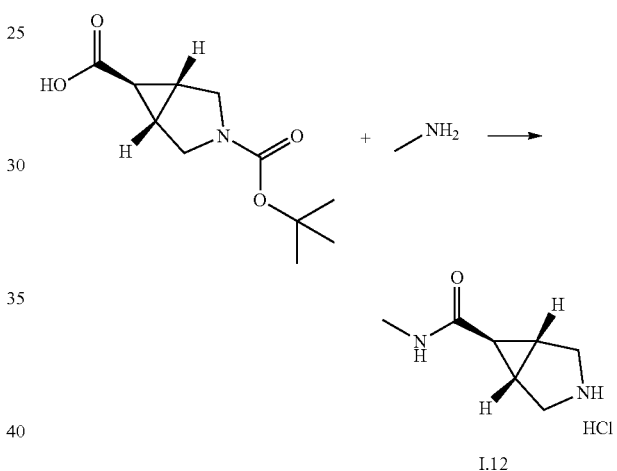

I.12

Step 1—Amide-coupling: trans-3-Aza-bicyclo[3.1.0]hexane-3,6-dicarboxylic acid 3-tert-butyl ester (1.00 g, 4.40 mmol) was dissolved in THF (5 mL) and TEA (4.94 mL; 35.20 mmol) and a solution of methylamine in THF (2 M; 4.40 mL; 8.80 mmol) was added. To the reaction mixture was added a solution of 1-propanephosphonic acid cyclic anhydride (50% in THF; 5.14 mL; 8.80 mmol) at RT. The reaction mixture was stirred at RT for 45 min and diluted with 4 N aq. sodium hydroxide (25 mL). The aq. phase was extracted with MTBE (2×25 mL) and the pooled organic phases were dried with Na$_2$SO$_4$, filtered and concentrated in vacuo.

Step 2—BOC deprotection: The crude material of step 1 was diluted with EtOAc (20 mL) and MeOH (20 mL) and treated with 4 N HCl in 1,4-dioxane (5 mL; 20.00 mmol) at RT. The reaction mixture was stirred at RT overnight. The reaction mixture was concentrated in vacuo to provide intermediate I.12.

Yield: 882 mg (91%), ESI-MS: m/z=141 [M+H]$^+$, R$_t$ (HPLC): 0.12 min (HPLC-5)

I.13: trans-3-Aza-bicyclo[3.1.0]hexane-1-carboxylic acid methylamide hydrochloride Amide Coupling:

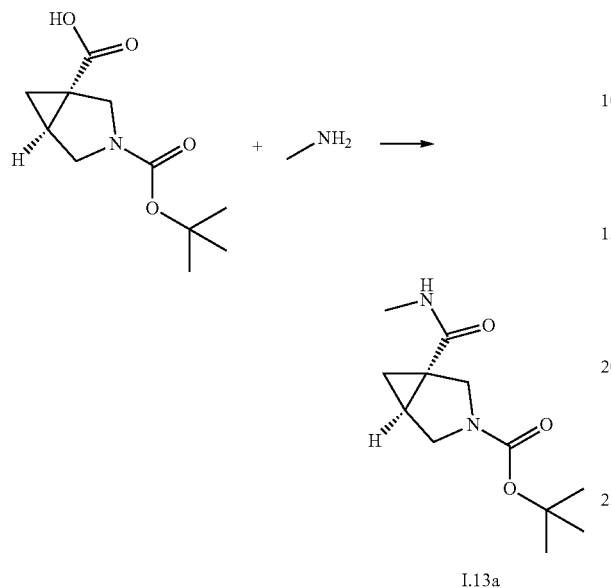

I.13a trans-3-Aza-bicyclo[3.1.0]hexane-1,3-dicarboxylic acid 3-tert-butyl ester (1.00 g, 4.40 mmol), HATU (1.90 g; 4.84 mmol) and DIPEA (1.89 mL; 11.00 mmol) were dissolved in DMF (8 mL) and stirred at RT for 30 min. Methylamine in THF (2 M; 4.40 mL; 8.80 mmol) was added to the reaction mixture and it was stirred at RT overnight. The reaction mixture was diluted with water and the aq. phase was extracted with DCM (3×20 mL). The pooled organic phases were washed with 1 N NaOH, dried and evaporated in vacuo. The residue was purified by RP-HPLC (ACN/water+TFA) and co-evaporated with iPrOH to provide intermediate I.13a.

Yield: 949 mg (90%), ESI-MS: m/z=185 [M+H]$^+$, R$_t$ (HPLC): 0.87 min (HPLC-5)

BOC Deprotection:

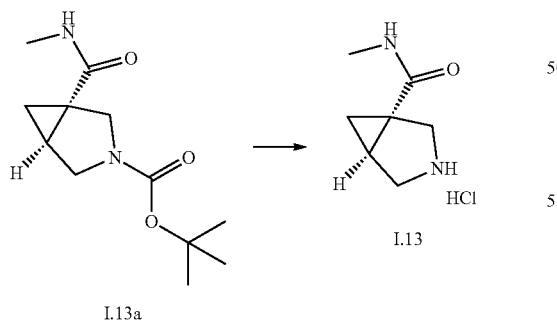

Intermediate I.13a (650 mg; 3.89 mmol) was dissolved in MeOH (2 mL) and hydrogen chloride (4 N in 1,4-dioxane; 5.00 mL; 20.00 mmol) was added. The reaction mixture was stirred at RT for 1 h 40 min. The reaction was reduced in vacuo and co-evaporated with MeOH (2×) to obtain intermediate I.13.

Yield: 650 mg (95%), ESI-MS: m/z=191 [M+H]$^+$, R$_t$ (HPLC): 0.09 min (HPLC-9)

I.14: N-Ethyl-2-piperidin-4-yl-acetamide hydrochloride

Amide Coupling:

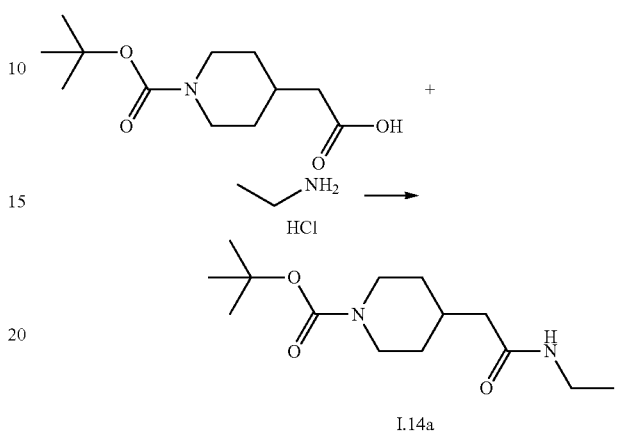

I.14a

4-Carboxymethyl-piperidine-1-carboxylic acid tert-butyl ester (3.00 g; 12.33 mmol), TBTU (3.96 g; 12.33 mmol) and TEA (5.19 mL; 36.99 mmol) were dissolved in DMF (10 mL). The solution was stirred at RT for 10 min. Ethylamine hydrochloride (1.01 g; 12.33 mmol) was added to the reaction mixture and it was stirred at RT overnight. To the reaction mixture was added TBTU and after 5 min stirring at RT ethylamine hydrochloride (0.5 g; 6.15 mmol) was added. After 4 h stirring at RT the reaction mixture was extracted with EtOAc. The organic phases were concentrated in vacuo. The crude material was dissolved in DCM, filtered over a basic Alox-cartridge and the filtrate was washed with aq. 0.1 N HCl and evaporated under reduced pressure to give intermediate XVII.1.

Yield: 3.3 g (99%), ESI-MS: m/z=271 [M+H]$^+$, R$_t$ (HPLC): 0.75 min (HPLC-3)

BOC Deprotection:

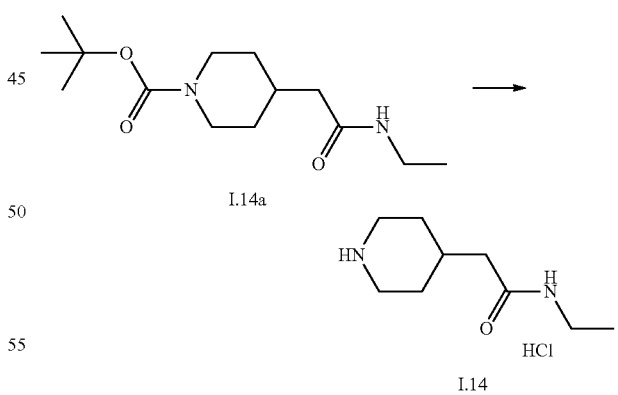

Intermediate I.14a (3.30 g; 12.21 mmol) was dissolved in 1,4-dioxane (30 mL) and a hydrogen chloride (4 N in 1,4-dioxane; 6.10 mL; 24.41 mmol) was added. The reaction mixture was stirred at RT overnight. To the reaction mixture was again added hydrogen chloride (4 N in 1,4-dioxane; 6.10 mL; 24.41 mmol) and the reaction mixture was stirred at RT overnight. The reaction mixture was diluted with diethyl ether and the precipitate was filtered to obtain intermediate I.14.

Yield: 2.52 g (100%), ESI-MS: m/z=171 [M+H]+, $R_t$ (HPLC): 0.78 min (HPLC-5)

Intermediate I.15: (R)-Pyrrolidine-3-carboxylic acid amide trifluoroacetate

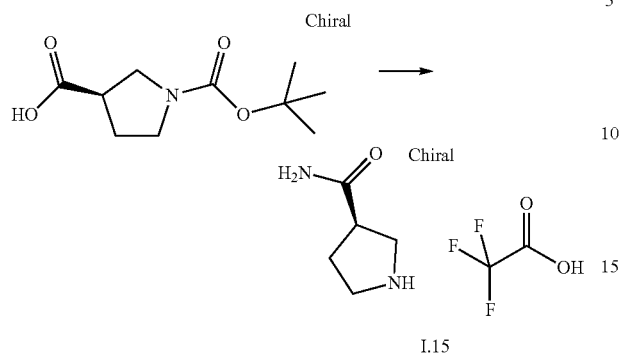

I.15

Step 1—Amide-coupling: (R)-Pyrrolidine-1,3-dicarboxylic acid 1-tert-butyl ester (800 mg; 3.61 mmol) was diluted with DCM (8 mL) and N-methylmorpholine (0.45 mL; 3.97 mmol) was added. The reaction mixture was cooled to 0° C. and IBCF (0.5 mL; 3.79 mmoL) was added. The reaction mixture was stirred at 0° C. for 5 min, warmed to RT and stirred for 1 h at RT. After addition of aq. NH4OH (32%; 0.67 mL; 5.41 mmol) the reaction mixture was stirred at RT for 80 min. The reaction mixture was diluted with water and extracted with DCM (2×20 ml). The pooled organic phases were washed with sat. aq. NaHCO3-solution, dried and evaporated under reduced pressure.

Step 2—BOC deprotection: The crude material of step 1 was dissolved in DCM (5 mL), TFA (0.83 mL; 10.81 mmol) was added and the reaction mixture was stirred at RT for 1 h. To the reaction mixture was added TFA (0.83 mL; 10.81 mmol) and it was stirred at RT overnight. The reaction mixture was concentrated in vacuo to provide intermediate I.15.

Yield: 1.19 g (100%), ESI-MS: m/z=115 [M+H]+, $R_t$ (HPLC): 0.11 min (HPLC-5)

Intermediate I.16: 4-Methyl-piperidin-4-ol

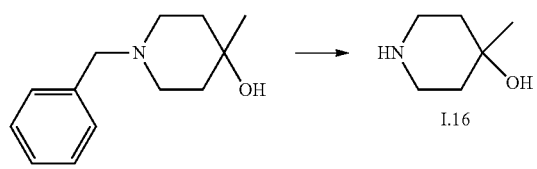

Under a hydrogen atmosphere (60 psi) 1-benzyl-4-methyl-piperidin-4-ol (10.0 g; 48.71 mmol) and Pd/C (10%; 0.5 g) in MeOH (150 mL) were stirred at RT for 19.5 h. After removal of the catalyst by filtration, the filtrate was evaporated under reduced pressure to provide intermediate I.16.

Yield: 16.94 g (quantitative)

Intermediate II.1: 1-[1-(6-Chloro-pyridine-3-sulfonyl)-piperidin-4-yl]-3-methyl-imidazolidin-2-one

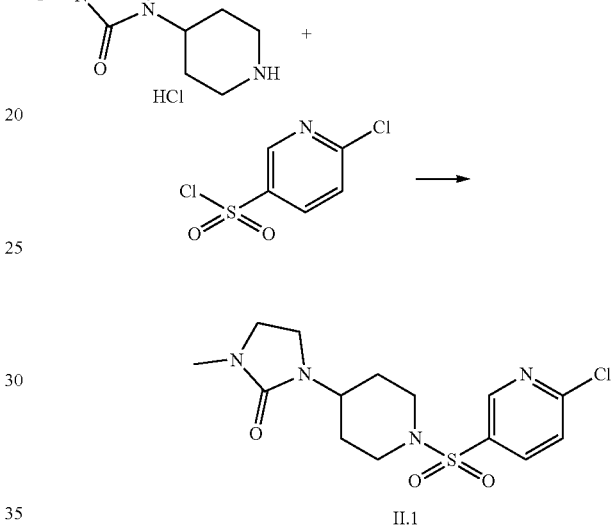

To a ice-cooled solution of 1-methyl-3-piperidin-4-yl-imidazolidin-2-one hydrochloride (42.8 mg; 0.19 mmol) in TEA (82 μL; 0.58 mmol) and NMP (1 mL) was added 6-chloropyridine-3-sulfonyl chloride (100 mg; 0.45 mmol) dissolved in NMP (1 mL). The reaction mixture was stirred at RT for 1 h and intermediate 11.1 was used as such for the next step.

The following intermediates were prepared in analogy to the above described procedure using 6-chloropyridine-3-sulfonyl chloride and the corresponding starting material. For changes from this procedure, see "synthesis comment".

| intermediate | structure | starting material | $R_t$ [min] (HPLC method) | MS | synthesis comment |
|---|---|---|---|---|---|
| II.2 | 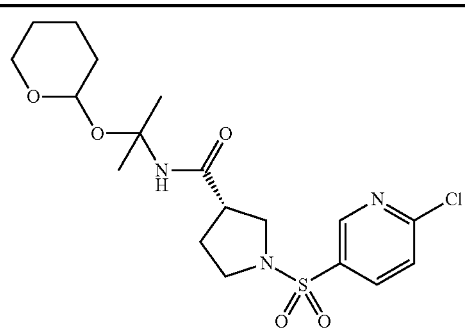 | I.1 | 0.84 (HPLC-5) | 362 | 1,4 eq Amin; DCM; 30 min |

-continued

| intermediate | structure | starting material | R$_t$ [min] (HPLC method) | MS | synthesis comment |
|---|---|---|---|---|---|
| II.3 | 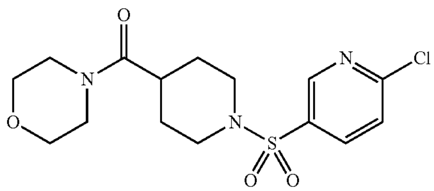 [SMILES: O=C(C1CCN(S(=O)(=O)c2ccc(Cl)nc2)CC1)N1CCOCC1] | | 0.87 (HPLC-5) | 374 | 6 eq TEA 0° C. to RT; overnight; workup: neutral and acidic extraction |
| II.4 | Chiral | I.2 | 0.87 (HPLC-5) | 318 | THF/DMSO 0° C. to RT |
| II.5 | 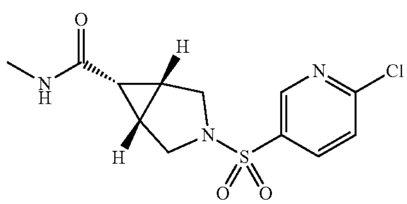 [SMILES: CNC(=O)[C@@H]1[C@@H]2CN(S(=O)(=O)c3ccc(Cl)nc3)C[C@@H]21] | I.3 | 0.76 (HPLC-5) | 316 | 6 eq TEA; 0° C. to RT; overnight; workup: neutral and acidic extraction |
| II.6 | Chiral | Chiral | — | — | NMP; 2 h |
| II.7 | 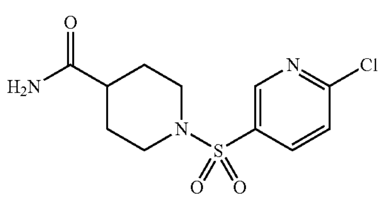 [SMILES: NC(=O)C1CCN(S(=O)(=O)c2ccc(Cl)nc2)CC1] | | 0.79 (HPLC-5) | 304 | |
| II.8 | Chiral | Chiral | — | — | 2.5 eq TEA; NMP 1 h |
| II.9 | 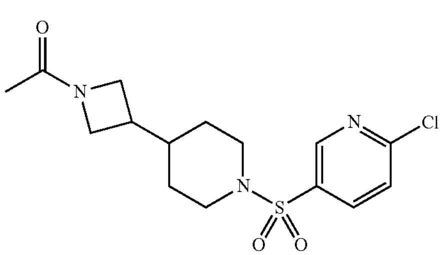 [SMILES: CC(=O)N1CC(C2CCN(S(=O)(=O)c3ccc(Cl)nc3)CC2)C1] | I.4 | — | — | 1.5 eq TEA; 0° C. to RT; overnight; workup: washed with water and concentrated in vacuo |

-continued

| intermediate | structure | starting material | R_t [min] (HPLC method) | MS | synthesis comment |
|---|---|---|---|---|---|
| II.10 | (azetidine-carbonyl-piperidine-sulfonyl-6-chloropyridine) | (azetidine-carbonyl-piperidine NH) + TFA | — | — | NMP; 2 h |
| II.11 | (N-methyl pyrrolidine-3-carboxamide sulfonyl-6-chloropyridine), Chiral | (N-methyl pyrrolidine-3-carboxamide NH·HCl), Chiral | 0.81 (HPLC-5) | 306 | THF; 0° C. to RT; 40 min |
| II.12 | (acetamido-pyrrolidine sulfonyl-6-chloropyridine) | (3-acetamido-pyrrolidine NH) | — | — | NMP; 1.5 eq TEA; 1 h |
| II.13 | Chiral (pyrrolidine-2-carboxamide sulfonyl-6-chloropyridine) | Chiral (prolinamide·HCl) | 0.77 (HPLC-5) | 292 | NMP; 0° C. to RT; overnight |
| II.14 | Chiral (N-methyl pyrrolidine-3-carboxamide sulfonyl-6-chloropyridine) | I.5 | 0.81 (HPLC-5) | 304 | 4 eq TEA; 40 min |
| II.15 | (N-ethyl piperidine-4-carboxamide sulfonyl-6-chloropyridine) | (N-ethyl piperidine-4-carboxamide NH·HCl) | 0.88 (HPLC-5) | 332 | 6 eq TEA; 0° C. to RT; overnight; workup: neutral and acidic extraction; crude material triturated with diisopropyl ether |
| II.16 | (3-hydroxy-3-methylazetidine sulfonyl-6-chloropyridine) | (3-hydroxy-3-methylazetidine NH·HCl) | — | — | NMP; 2 h |

-continued

| intermediate | structure | starting material | R_t [min] (HPLC method) | MS | synthesis comment |
|---|---|---|---|---|---|
| II.17 | [structure] | [structure] HCl | 0.88 (HPLC-5) | 332 | 6 eq TEA; 0° C. to RT; Overnight; workup: neutral and acidic extraction; crude material triturated with diisopropyl ether |
| II.18 | [structure] Chiral | [structure] Chiral | 0.76 (HPLC-5) | 290 | 1.5 eq TEA; 0° C. to RT 40 min |
| II.19 | [structure] | I.6 | — | — | NMP; 0° C. to RT; 1 h |
| II.20 | [structure] | [structure] HCl | 0.74 (HPLC-5) | 276 | THF/DMSO; 0° C. to RT; 10 min |
| II.21 | [structure] Chiral | I.7 | 0.87 (HPLC-5) | 360 | THF/DMSO; 0° C. to RT; 40 min |
| II.22 | [structure] | I.8 | 0.48 (HPLC-1) | 371 | 1 h; workup: aq. extraction; purification by prep. HPLC |

-continued

| intermediate | structure | starting material | R_t [min] (HPLC method) | MS | synthesis comment |
|---|---|---|---|---|---|
| II.23 | 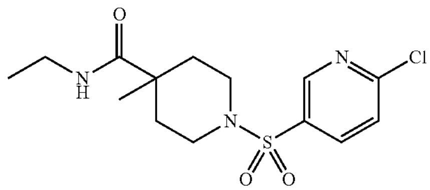 [SMILES: CCNC(=O)C1(C)CCN(S(=O)(=O)c2ccc(Cl)nc2)CC1] | I.9 | 0.93 (HPLC-5) | 346 | 4 eq TEA; THF/DMSO |
| II.24 | Chiral | I.10 | — | — | NMP; 2 h |
| II.25 | 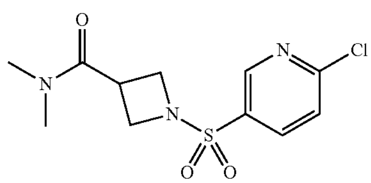 [SMILES: CN(C)C(=O)C1CN(S(=O)(=O)c2ccc(Cl)nc2)C1] | | 0.84 (HPLC-5) | 304 | THF/DMSO; 0° C. to RT; 40 min |
| II.26 | 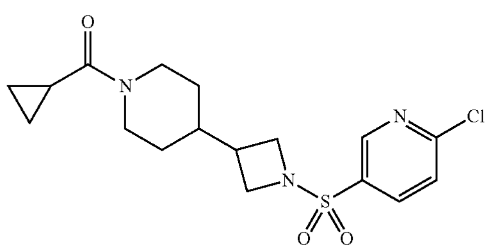 [SMILES: O=C(C1CC1)N1CCC(C2CN(S(=O)(=O)c3ccc(Cl)nc3)C2)CC1] | I.11 | — | — | NMP; 2 h |
| II.27 | 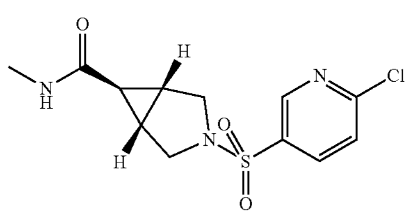 [SMILES: CNC(=O)[C@H]1[C@@H]2CN(S(=O)(=O)c3ccc(Cl)nc3)C[C@@H]21] | I.12 | 0.83 (HPLC-5) | 316 | 6 eq TEA; 0° C. to RT; overnight; workup: extraction with water/1 N aq. HCl; crude material triturated with diisopropyl ether |
| II.28 | 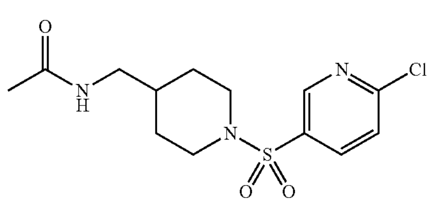 [SMILES: CC(=O)NCC1CCN(S(=O)(=O)c2ccc(Cl)nc2)CC1] | | — | — | NMP; 2 h |

| intermediate | structure | starting material | R$_t$ [min] (HPLC method) | MS | synthesis comment |
|---|---|---|---|---|---|
| II.29 | 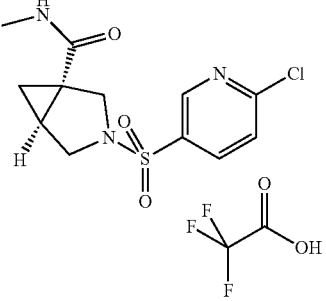 | I.13 | 0.47 (HPLC-1) | 315 | 1 h; workup: extraction with water; crude material triturated with diisopropyl ether |
| II.30 | 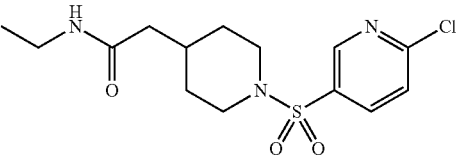 [SMILES: CCNC(=O)CC1CCN(S(=O)(=O)c2ccc(Cl)nc2)CC1] | I.14 | — | — | NMP; 2 h |
| II.31 | 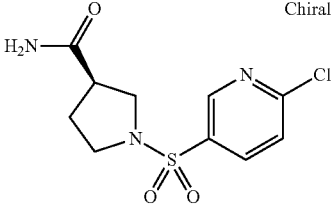 [SMILES: NC(=O)[C@@H]1CCN(S(=O)(=O)c2ccc(Cl)nc2)C1 ; "Chiral"] | I.15 | 0.77 (HPLC-5) | 290 | 5 eq TEA; 0° C. to RT; 20 min; workup: precipitation with water and DCM; filtration of the product and dried under reduced pressure |
| II.32 | 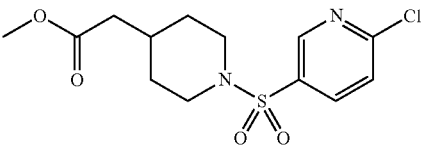 [SMILES: COC(=O)CC1CCN(S(=O)(=O)c2ccc(Cl)nc2)CC1] | 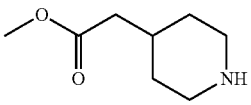 | 0.60 (HPLC-1) | 332 | 2 eq TEA; 1 h; |
| II.33 | 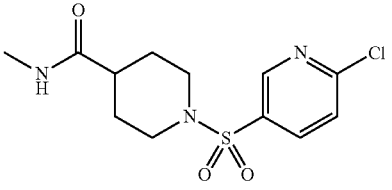 [SMILES: CNC(=O)C1CCN(S(=O)(=O)c2ccc(Cl)nc2)CC1] | 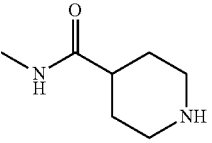 | 0.82 (HPLC-5) | 318 | 0° C. to RT; overnight; workup: neutral and acidic extraction; crude material triturated with diisopropyl ether |
| II.34 | 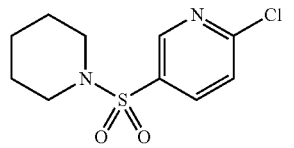 [SMILES: O=S(=O)(c1ccc(Cl)nc1)N1CCCCC1] | 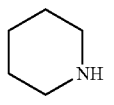 | 0.58 (HPLC-1) | 261 | 2 eq TEA; 1 h; workup: extraction with water; crude material triturated with diisopropyl ether |
| II.35 | 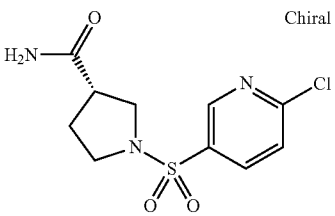 [SMILES: NC(=O)[C@H]1CCN(S(=O)(=O)c2ccc(Cl)nc2)C1 ; "Chiral"] | 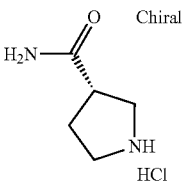 | 0.43 (HPLC-2) | 290 | 5° C. to RT; overnight; workup: dilution with water and DCM; filtration of the precipitate |

-continued

| intermediate | structure | starting material | R$_t$ [min] (HPLC method) | MS | synthesis comment |
|---|---|---|---|---|---|
| II.36 | 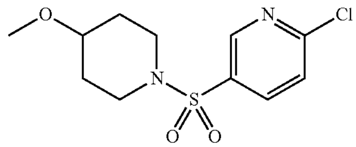 [SMILES: COC1CCN(S(=O)(=O)c2ccc(Cl)nc2)CC1] | | 0.53 (HPLC-1) | 291 | 2 eq TEA; 1 h; workup: aq. extraction |
| II.37 | 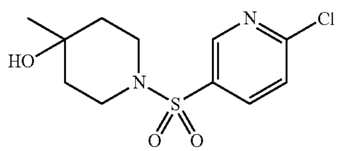 [SMILES: CC1(O)CCN(S(=O)(=O)c2ccc(Cl)nc2)CC1] | I.16 | 0.53 (HPLC-2) | 291 | overnight; workup: extraction with water; 1 N aq. HCl; crude material triturated with diisopropyl ether |
| II.38 | 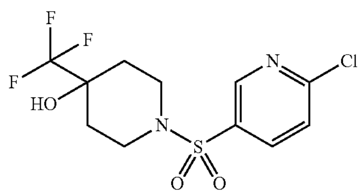 [SMILES: O=S(=O)(c1ccc(Cl)nc1)N1CCC(O)(C(F)(F)F)CC1] | | 0.63 (HPLC-2) | 345 | 5° C. to RT; overnight; workup: extraction with water; 1 N aq. HCl; crude material triturated with diisopropyl ether |

Intermediate II.39: 2-Chloro-5-(3-methoxy-azetidine-1-sulfonyl)-pyridine

Intermediate II.40: 2-Chloro-5-[(S)-3-(tetrahydropyran-2-yloxy)-pyrrolidine-1-sulfonyl]-pyridine

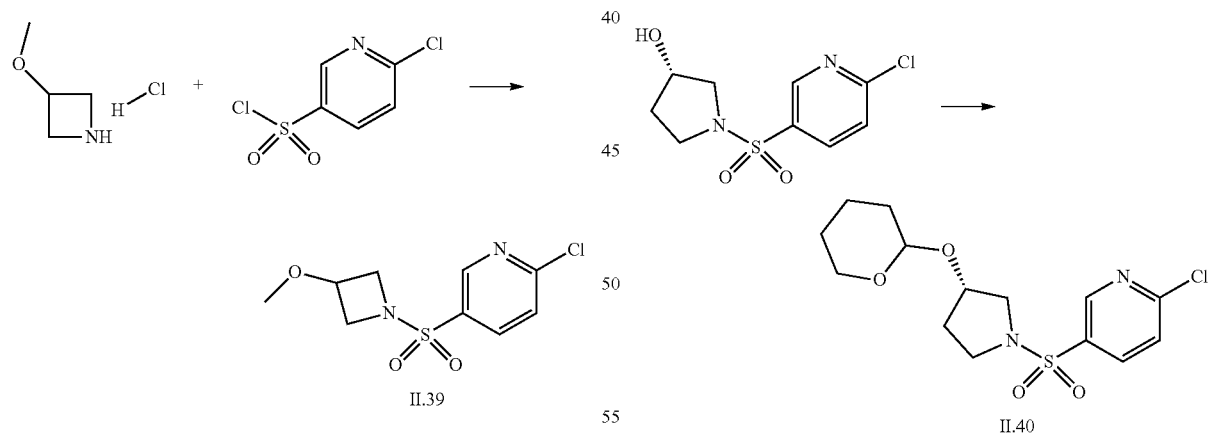

A solution of 6-chloro-pyridine-3-sulfonyl chloride (200 mg; 0.94 mmol) in DCM (5.00 mL) was treated with TEA (0.26 mL; 1.88 mmol) and 3-methoxy-azetidine hydrochloride (117 mg; 0.94 mmol) was added to the reaction mixture. The mixture was stirred for 1 h, diluted with 30 mL DCM and washed twice with water. The organic phase was dried over sodium sulfate, concentrated in vacuo and triturated with diisopropyl ether to give intermediate 11.39.

Yield: 190 mg (77%), ESI-MS: m/z=263 [M+H]$^+$, R$_t$ (HPLC): 0.44 min (HPLC-1)

(S)-1-(6-Chloro-pyridine-3-sulfonyl)-pyrrolidin-3-ol (95 mg; 0.36 mmol) was dissolved in THF (1 mL) and p-toluenesulfonic acid monohydrate (3.7 mg; 0.02 mmol) and 3,4-dihydropyrane (70 µL; 1.06 mmol) were added at RT. The reaction mixture was stirred at RT for 50 min and then purified by RP-HPLC (ACN/water+TFA) to provide intermediate 11.40.

Yield: 153 mg (quantitative), ESI-MS: m/z=263 [M+H]$^+$, R$_t$ (HPLC): 1.05 min (HPLC-3)

Intermediate III.1: 1-(6-Fluoro-pyridine-3-sulfonyl)-piperidine-4-carboxylic acid methyl ester Intermediate IV.1: tert-Butyl-N-[2-(fluoromethyl-idene)-3-hydroxypropyl]-, carbamate (E/Z-mixture)

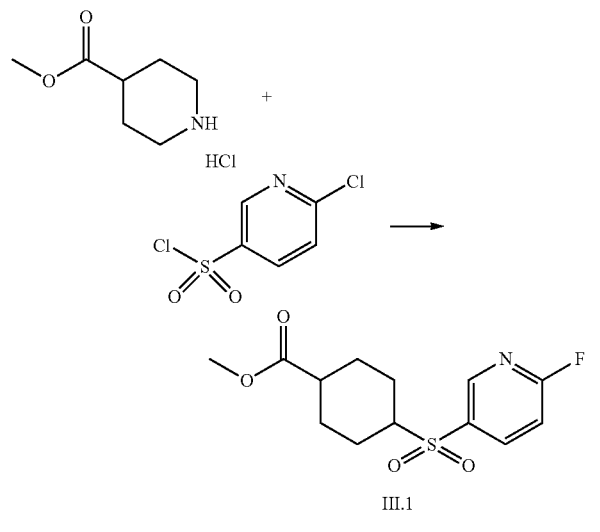

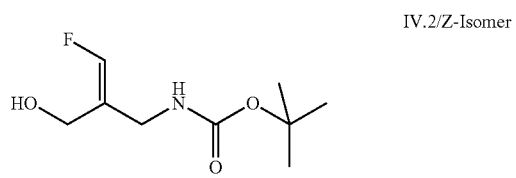

The E/Z-mixture of the alcohol was prepared according to the procedure described in WO 2013/163675, pp. 50-53.

Intermediate IV.2: 1 ((Z)-3-Fluoro-2-hydroxymethyl-allyl)-carbamic acid tert-butyl ester Piperidine-4-carboxylic acid methyl ester (1.15 g; 6.39 mmol) was suspended in DCM (40 mL) and a solution of TEA (3.56 mL; 25.56 mmol) and 6-fluoropyridine-3-sulfonyl chloride (1.25 g; 6.39 mmol) in DCM (10 mL) was added. The reaction mixture was stirred at RT for 45 min. The reaction mixture was diluted with DCM (50 mL) and extracted with water (2×40 mL). The organic phase was dried with $Na_2SO_4$ and the solvent was evaporated. The crude material was suspended in MTBE and the solid was filtered to give intermediate 111.1.

Yield: 1.40 g (73%), ESI-MS: m/z=302 [M+H]$^+$, $R_t$ (HPLC): 0.52 min (HPLC-1)

The following intermediates were prepared in analogy to the above described procedure using 6-fluoropyridine-3-sulfonyl chloride and the corresponding starting material. For changes from this procedure, see "synthesis comment".

Intermediate IV.1 (4.00 g; 19.49 mmol) was purified three times by column chromatography on silica gel to give the single Z-isomer IV.2 (0.98 g; 4.78 mmol; 25%).

| intermediate | structure | starting material | $R_t$ [min] (HPLC method) | MS | synthesis comment |
|---|---|---|---|---|---|
| III.2 | 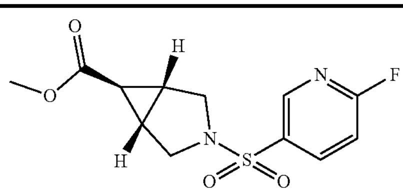 | | 0.53 (HPLC-1) | 301 | 2 eq TEA; 1.5 h |
| III.3 | 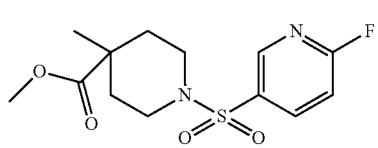 [SMILES: COC(=O)C1(C)CCN(S(=O)(=O)c2ccc(F)nc2)CC1] | | 0.53 (HPLC-1) | 301 | 2° eq TEA; 3.5 h |
| III.4 | 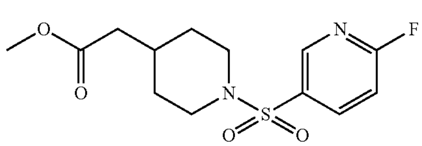 [SMILES: COC(=O)CC1CCN(S(=O)(=O)c2ccc(F)nc2)CC1] | | 0.67 (HPLC-1) | 317 | 2 eq TEA; 3.5 h |

Example 1: 1-{1-[6-((Z)-2-Aminomethyl-3-fluoro-allyloxy)-pyridine-3-sulfonyl]-piperidine-4-yl}-3-methyl-imidazolidin-2-one trifluoroacetate Substitution:

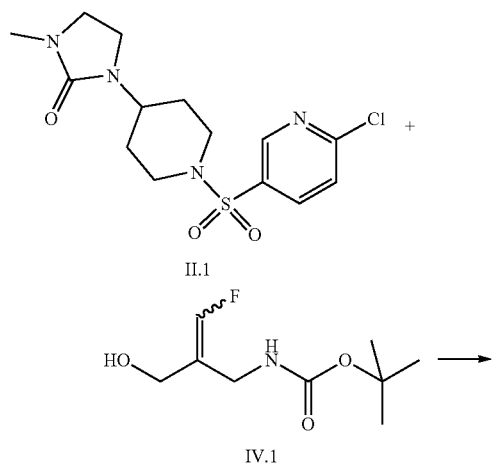

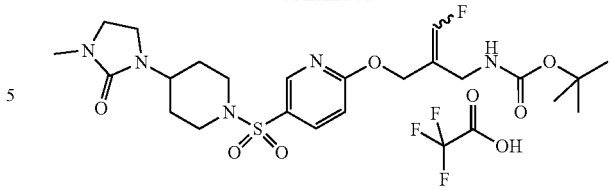

BOC-protected example 1

Intermediate II.1 (solution in NMP and TEA; 0.19 mmol) was cooled in an ice bath and a solution of intermediate IV.1 (40 mg; 0.19 mmol) in THF (0.5 mL; S), and sodium tert-butoxide (2 M in THF; 390 µL; 0.78 mmol; B) were added. The reaction mixture was agitated at RT (T) for 2 h (t), diluted with water, acidified with TFA and purified by RP-HPLC (ACN/water+TFA) to obtain the BOC-protected example 1.

Yield: 36 mg (70%), ESI-MS: m/z=528 [M+H]$^+$, R$_t$ (HPLC): 1.05 min (HPLC-5)

BOC Deprotection:

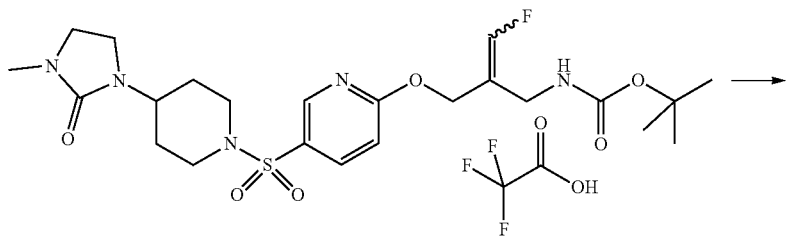

BOC-protected example 1

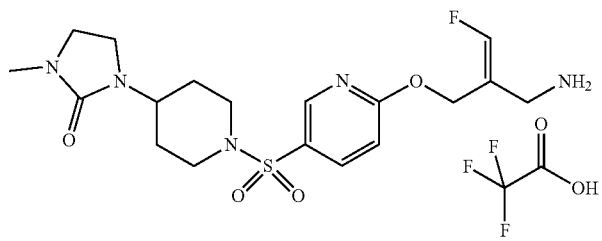

example 1

The BOC-protected example 1 (36 mg; 0.07 mmol) was dissolved in DCM (0.5 mL; S) and TFA (1.0 mL; 12.31 mmol; A) was added. The reaction mixture was stirred at RT (T) for 2 h (t), then evaporated under reduced pressure and purified by RP-HPLC (ACN/water+TFA) to give example 1.

Yield: 7.5 mg (7%), ESI-MS: m/z=428 [M+H]$^+$, R$_t$ (HPLC): 0.75 min (HPLC-5)

The following examples (example number given in column Ex.) were prepared in analogy to the above described procedure using the corresponding starting materials. Details for the two steps are given in the column synthesis comment, the retention-time and mass (ESI-MS, m/z=[M+H]$^+$) determined by HPLC-MS are given in the columns RT and MS.

| Ex. | structure |
|---|---|
| 2 | 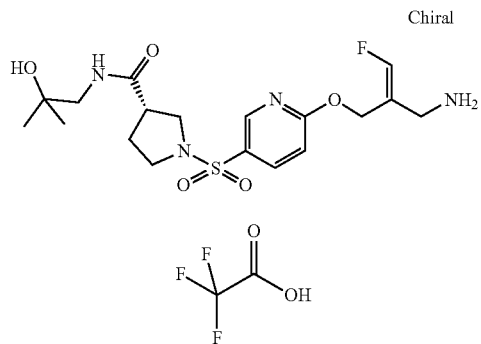 Chiral 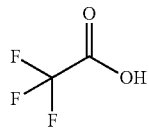 |
| 3 | 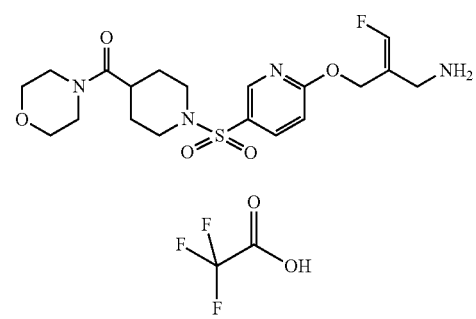 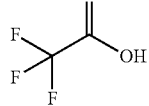 |
| 4 | 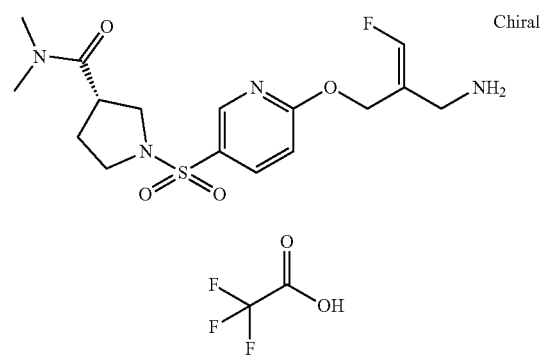 Chiral 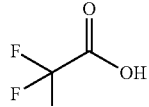 |
| 5 | 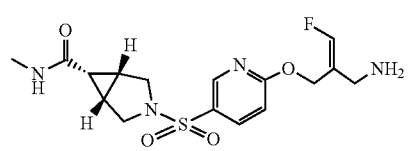 [SMILES: CNC(=O)[C@@H]1[C@@H]2CN(S(=O)(=O)c3ccc(OC/C(=C\F)CN)nc3)C[C@@H]21] 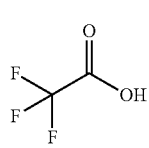 |
| 6 |  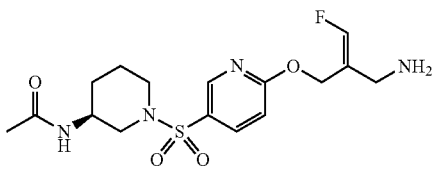 [SMILES: CC(=O)N[C@H]1CCCN(S(=O)(=O)c2ccc(OC/C(=C\F)CN)nc2)C1] |
| 7 | 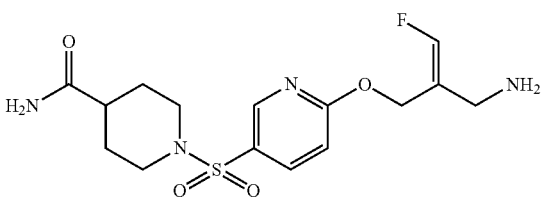 [SMILES: NC/C(=C/F)COc1ccc(S(=O)(=O)N2CCC(C(N)=O)CC2)cn1] 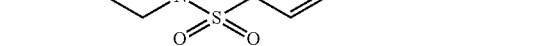 |
| 8 | 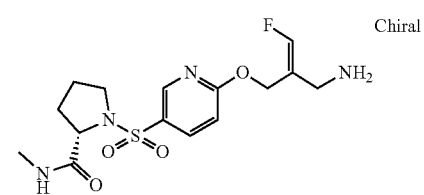 [SMILES: CNC(=O)[C@@H]1CCCN1S(=O)(=O)c1ccc(OC/C(=C\F)CN)nc1] Chiral |
| 9 | 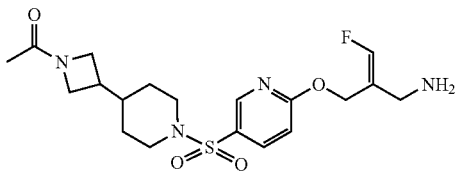 [SMILES: CC(=O)N1CC(C2CCN(S(=O)(=O)c3ccc(OC/C(=C\F)CN)nc3)CC2)C1] 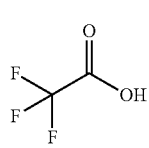 |

| Ex. | structure |
|---|---|
| 10 | 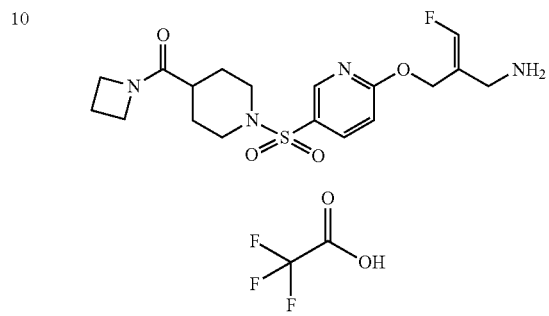 |
| 11 | 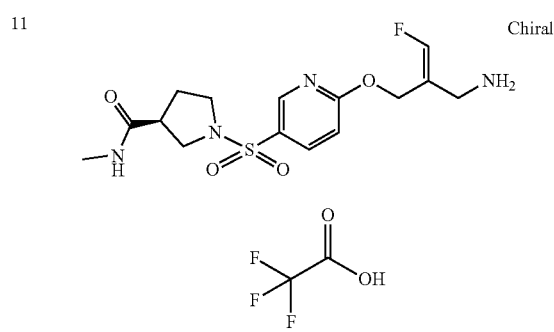 Chiral |
| 12 | 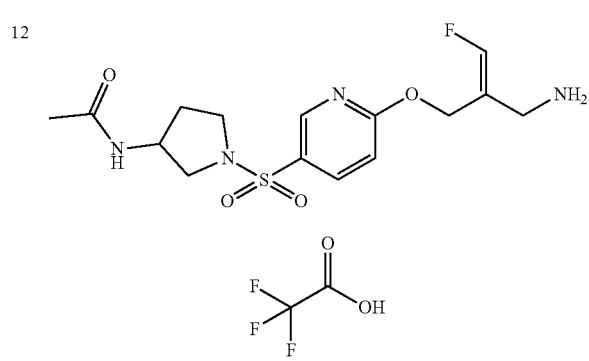 |
| 13 | 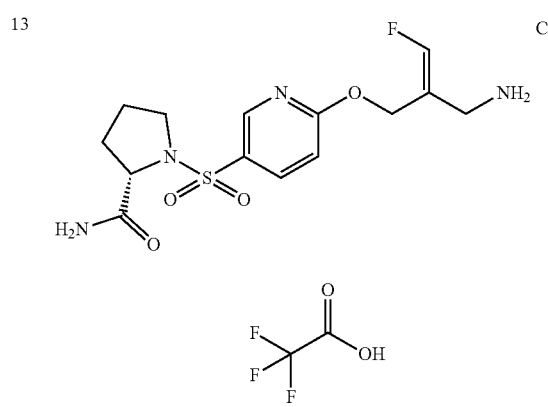 Chiral |
| 14 | 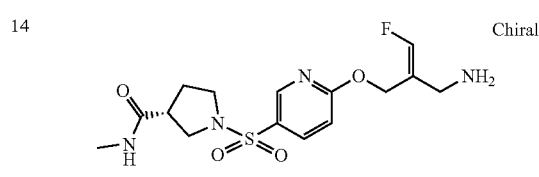 Chiral |
| Ex. | structure |
|---|---|
| 15 | 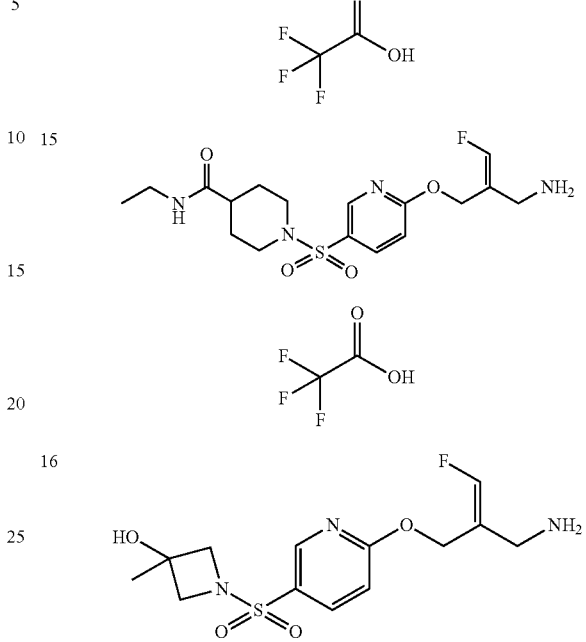 |
| 16 | 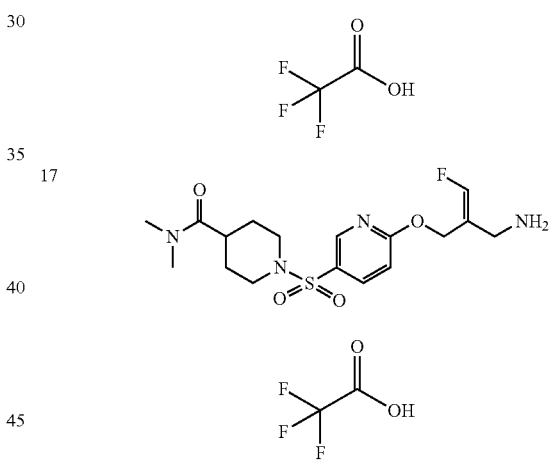 |
| 17 | 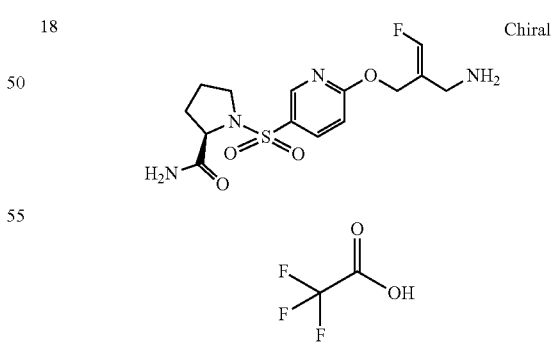 |
| 18 | 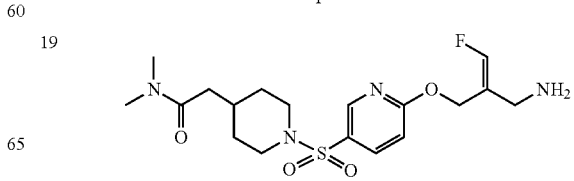 Chiral |
| 19 | |

| Ex. | structure |
|---|---|
| 20 | 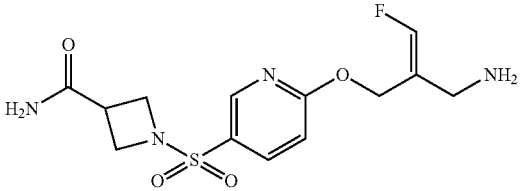 [SMILES: NC/C(=C/F)COc1ccc(S(=O)(=O)N2CC(C(N)=O)C2)cn1] |
| 21 | 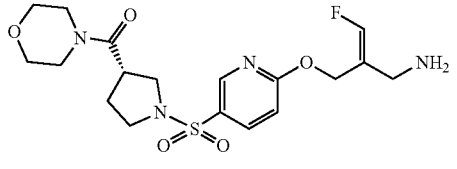 |
| 22 | 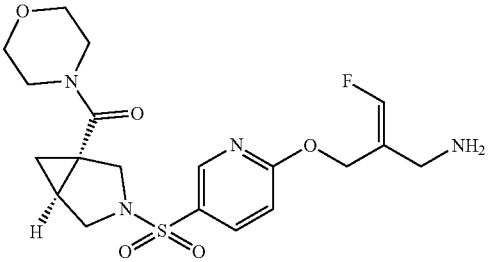 [SMILES: NC/C(=C/F)COc1ccc(S(=O)(=O)N2C[C@H]3C[C@@]3(C(=O)N3CCOCC3)C2)cn1] |
| 23 | 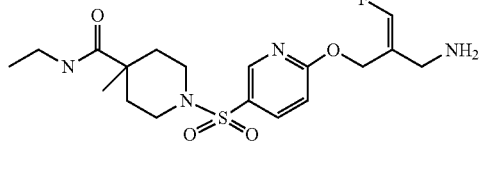 |
| 24 | 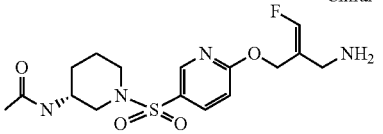 |
| 25 | 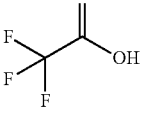 |
| 26 | 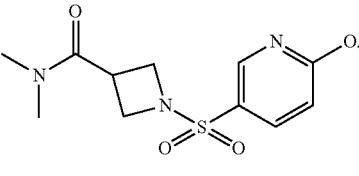 |
| 27 | 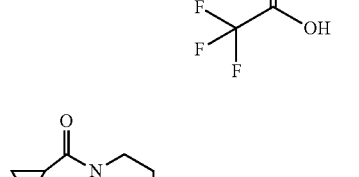 |
| 28 | 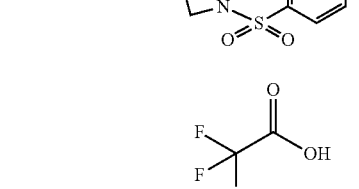 |

| Ex. | structure |
|---|---|
| 29 | 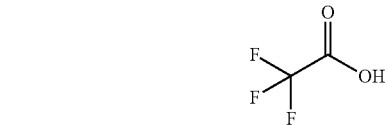 |
| | 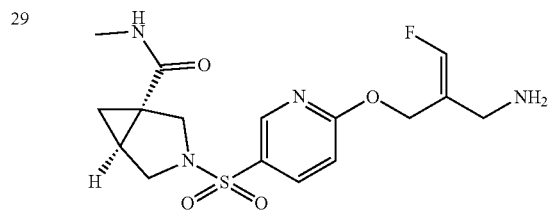 |
| 30 | 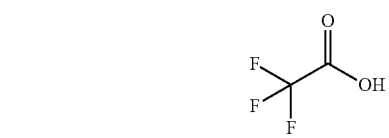 |
| | 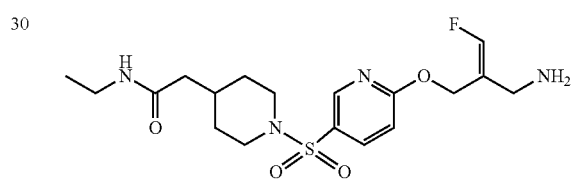 |
| 31 Chiral | 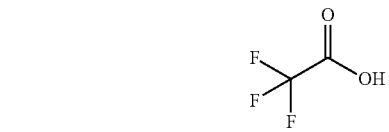 |
| | 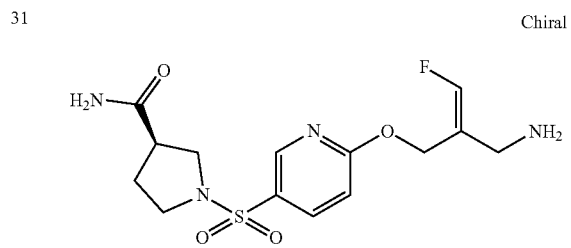 |

| Ex. | structure |
|---|---|
| 32 | (methyl piperidine acetate sulfonyl pyridyl-O-CH2-C(=CHF)-CH2NH2); TFA |
| 33 | (methoxy-azetidine-piperidine sulfonyl pyridyl-O-CH2-C(=CHF)-CH2NH2); TFA |
| 34 | (methyl piperidine-4-carboxylate sulfonyl pyridyl-O-CH2-C(=CHF)-CH2NH2); TFA |

| | | Substitution | | | BOC deprotection | | |
|---|---|---|---|---|---|---|---|
| Ex. | starting materials | R_t [min] (HPLC method) | MS | synthesis comment | R_t [min] (HPLC method) | MS | synthesis comment |
| 2 | II.2; IV.1 | 1.01 (HPLC-5) | 531 | S: THF/DCM B: 4.00 eq T: RT t: 40 min | 0.71 (HPLC-5) | 431 | S: DCM A: 12 eq TFA T: RT t: 1 h |
| 3 | II.3; IV.1 | 1.07 (HPLC-5) | 443 | S: THF/DMSO B: 1.05 eq T: 0° C. to RT t: 50 min | 0.74 (HPLC-5) | 443 | S: DCM A: 25 eq TFA T: RT |
| 4 | II.4; IV.1 | 1.04 (HPLC-5) | 487 | S: THF/DMSO B: 4.10 eq T: 0° C. to RT t: 100 min | 0.72 (HPLC-5) | 387 | S: DCM A: 9 eq TFA (A) T: RT t: 75 min |

|  |  | Substitution |  |  | BOC deprotection |  |  |
| --- | --- | --- | --- | --- | --- | --- | --- |
| Ex. | starting materials | R$_t$ [min] (HPLC method) | MS | synthesis comment | R$_t$ [min] (HPLC method) | MS | synthesis comment |
| 5 | II.5; IV.1 | 1.00 (HPLC-5) | 485 | S: THF/DMSO B: 1.05 eq T: 0° C. to RT t: 50 min | 0.66 (HPLC-5) | 385 | S: DCM A: 20 eq TFA T: RT t: 75 min |
| 6 | II.6; IV.1 | 0.74 (HPLC-7) | 487 | S: THF/NMP B: 4.10 eq T: 0° C. to RT t: 18 h | 0.39 (HPLC-6) | 387 | S: DCM A: 51 eq TFA T: RT t: 1 h |
| 7 | II.7; IV.1 | 0.97 (HPLC-5) | 373 | S: THF/DMSO B: 1.05 eq T: 0° C. to RT t: 65 min | 0.69 (HPLC-5) | 373 | S: DCM A: 18 eq TFA T: RT t: 1 h |
| 8 | II.8; IV.1 | 0.99 (HPLC-5) | 473 | S: THF/NMP B: 3.00 eq T: 0° C. to RT t: overnight | 0.67 (HPLC-5) | 373 | S: DCM A: 44 eq TFA T: RT t: 2 h |
| 9 | II.9; IV.1 | — | — | S: DCM/THF V.1: 2 eq B: 6 eq T: 0° C. to RT t: 2 d; used crude for BOC deprotection | 0.40 (HPLC-2) | 427 | S: DCM A: 5 eq TFA T: RT t: overnight |
| 10 | II.10; IV.1 | 0.77 (HPLC-7) | 512 | S: THF/NMP B: 4.10 eq T: 0° C. to RT t: overnight | 0.42 (HPLC-6) | 412 | S: DCM A: 51 eq TFA T: RT t: 1 h |
| 11 | II.11; IV.1 | 1.01 (HPLC-5) | 473 | S: THF/DMSO B: 4.10 eq T: 0° C. to RT t: 100 min | 0.69 (HPLC-5) | 373 | S: DCM A: 11 eq TFA T: RT |
| 12 | II.12; IV.1 | 0.98 (HPLC-5) | 473 | S: THF/NMP B: 3.00 eq T: 0° C. to RT t: 18 h | 0.67 (HPLC-5) | 373 | S: DCM A: 63 eq TFA T: RT t: 2 h |
| 13 | II.13; IV.1 | 0.97 (HPLC-5) | 459 | S: THF/NMP B: 4.10 eq T: 0° C. to RT t: 50 min | 0.65 (HPLC-5) | 359 | S: DCM A: 4 eq TFA T: RT t: 2 h |
| 14 | II.14; IV.1 | 1.00 (HPLC-5) | 473 | S: THF/DCM B: 4.00 eq T: RT t: 18 h | 0.68 (HPLC-5) | 373 | S: DCM A: 30 eq TFA T: RT t: 2 h |
| 15 | II.15; IV.1 | 1.07 (HPLC-5) | 401 | S: THF/DMSO B: 1.50 eq T: 0° C. to RT t: 50 min | 0.74 (HPLC-5) | 401 | S: DCM A: 30 eq TFA T: RT t: 2 h |
| 16 | II.16; IV.1 | 0.74 (HPLC-7) | 432 | S: THF/NMP B: 4.10 eq T: 0° C. to RT t: 18 h | 0.36 (HPLC-6) | 332 | S: DCM A: 51 eq TFA T: RT t: 1 h |
| 17 | II.17; IV.1 | 1.08 (HPLC-5) | 401 | S: THF/DMSO B: 1.05 eq T: 0° C. to RT t: 1 h | 0.74 (HPLC-5) | 401 | S: DCM A: 25 eq TFA T: RT t: 1 h |
| 18 | II.18; IV.1 | 0.98 (HPLC-5) | 359 | S: THF B: 2.05 eq T: 0° C. to RT t: 1 h | 0.65 (HPLC-5) | 359 | S: DCM A: 5 eq TFA T: RT t: 1 h |
| 19 | II.19; IV.1 | 1.05 (HPLC-5) | 515 | S: THF/NMP B: 4.00 eq T: 0° C. to RT t: 2 h | 0.76 (HPLC-5) | 415 | S: DCM A: 5 eq TFA T: RT t: 2 h |
| 20 | II.20; IV.1 | 0.97 (HPLC-5) | 445 | S: THF/DMSO B: 2.05 eq T: 0° C. to RT t: 3 h | 0.65 (HPLC-5) | 345 | S: DCM A: 60 eq TFA T: RT |
| 21 | II.21; IV.1 | 1.04 (HPLC-5) | 529 | S: THF/DMSO B: 4.10 eq T: 0° C. to RT t: 1.5 h | 0.72 (HPLC-5) | 429 | S: DCM A: 7 eq TFA T: RT t: 2 h |

| | | Substitution | | | BOC deprotection | | |
|---|---|---|---|---|---|---|---|
| Ex. | starting materials | $R_t$ [min] (HPLC method) | MS | synthesis comment | $R_t$ [min] (HPLC method) | MS | synthesis comment |
| 22 | II.22; IV.1 | 0.63 (HPLC-1) | 541 | S: THF<br>B: 4.00 eq<br>T: 0° C. to RT<br>t: 1.5 h | 0.44 (HPLC-1) | 441 | S: DCM<br>A: 13 eq TFA<br>T: RT<br>t: 2 h |
| 23 | II.23; IV.1 | 1.07 (HPLC-5) | 515 | S: THF/DMSO<br>B: 4.00 eq<br>T: RT<br>t: 1.5 h | 0.76 (HPLC-5) | 415 | S: DCM<br>A: 5 eq TFA<br>T: RT<br>t: 2 h |
| 24 | II.24; IV.1 | 0.74 (HPLC-7) | 487 | S: THF/NMP<br>B: 4.10 eq<br>T: 0° C. to RT<br>t: 18 h | 0.39 (HPLC-6) | 387 | S: DCM<br>A: 51 eq TFA<br>T: RT<br>t: 1 h |
| 25 | II.25; IV.1 | 1.03 (HPLC-5) | 473 | S: THF/DMSO<br>B: 4.10 eq<br>T: 0° C. to RT<br>t: 75 min | 0.70 (HPLC-5) | 373 | S: DCM<br>A: 9 eq TFA<br>T: RT<br>t: 1 h |
| 26 | II.26; IV.1 | 0.84 (HPLC-7) | 553 | S: THF/NMP<br>B: 4.10 eq<br>T: 0° C. to RT<br>t: 18 h | 0.51 (HPLC-6) | 453 | S: DCM<br>A: 51 eq TFA<br>T: RT<br>t: 1 h |
| 27 | II.27; IV.1 | 1.05 (HPLC-5) | 385 | S: THF/DMSO<br>B: 1.05 eq<br>T: 0° C. to RT<br>t: 50 min | 0.71 (HPLC-5) | 385 | S: DCM<br>A: 8 eq TFA<br>T: RT<br>t: 1 h |
| 28 | II.28; IV.1 | 0.73 (HPLC-7) | 501 | S: THF/NMP<br>B: 4.10 eq<br>T: 0° C. to RT<br>t: 18 h | 0.40 (HPLC-6) | 401 | S: DCM<br>A: 51 eq TFA<br>T: RT<br>t: 1 h |
| 29 | II.29; IV.1 | 0.61 (HPLC-1) | 485 | S: THF<br>B: 4.00 eq<br>T: RT<br>t: 30 min | 0.38 (HPLC-1) | 385 | S: DCM<br>A: 51 eq TFA<br>T: RT<br>t: 1 h |
| 30 | II.30; IV.1 | 0.78 (HPLC-7) | 515 | S: THF/NMP<br>B: 4.10 eq<br>T: 0° C. to RT<br>t: overnight | 0.44 (HPLC-6) | 415 | S: DCM<br>A: 51 eq TFA<br>T: RT<br>t: 1 h |
| 31 | II.31; IV.1 | 0.96 (HPLC-5) | 459 | S: THF/DMSO<br>B: 1.05 eq<br>T: RT<br>t: overnight | 0.65 (HPLC-5) | 359 | S: DCM<br>A: 18 eq TFA<br>T: RT<br>t: 2 h |
| 32 | II.32; IV.1 | 0.71 (HPLC-1) | 502 | S: Tol<br>B: 2.50 eq (solid)<br>T: RT<br>t: 3.5 h | 0.45 (HPLC-1) | 402 | S: 1,4-dioxane<br>A: 60 eq HCl<br>T: RT<br>t: 1 h |
| 33 | II.39; IV.2 | 1.05 (HPLC-5) | 432 | S: THF/NMP<br>B: 4.0 eq. (solid)<br>T: RT<br>t: 10 min | 0.70 (HPLC-5) | 332 | S: DCM<br>A: 25 eq TFA<br>T: 0° C. then RT<br>t: overnight |
| 34 | III.1; IV.1 | 0.69 (HPLC-1) | 488 | S: Tol<br>B: 1.00 eq (solid)<br>T: RT<br>t: 1 h | 0.45 (HPLC-1) | 388 | S: DCM<br>A: 4 eq TFA<br>T: RT<br>t: 3d |

Example 35: trans-3-[6-((Z)-2-Aminomethyl-3-fluoro-allyloxy)-pyridine-3-sulfonyl]-3-aza-bicyclo[3.1.0]hexane-6-carboxylic acid methyl ester trifluoroacetate Substitution:

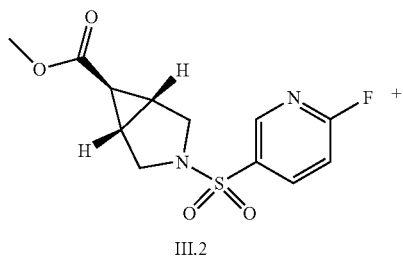

III.2

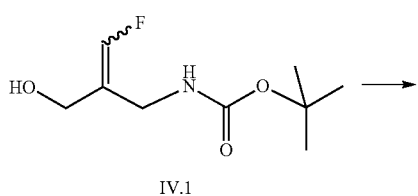

IV.1

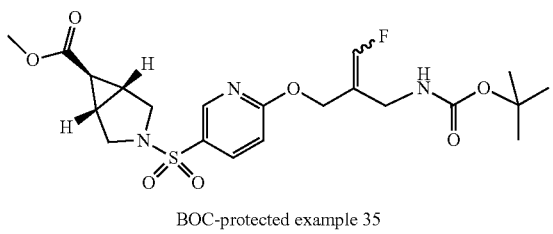

BOC-protected example 35

To a solution of intermediate V.1 (1.16 g; 5.66 mmol) in toluene (30 mL; S) sodium tert-butoxide (0.54 g; 5.66 mmol; B; solid) and intermediate III.2 (1.70 g; 5.66 mmol) were added. The reaction mixture was stirred at RT (T) 70 min (t). The reaction mixture was diluted with toluene und extracted with water two times. The pooled organic phases were dried with Na₂SO₄ and evaporated under reduced pressure. The residue was purified by silica gel chromatography to provide the BOG-protected example 35.

Yield: 2.53 g (92%), ESI-MS: m/z=486 [M+H]⁺, R$_t$ (HPLC): 0.69 min (HPLC-1)

Bog Deprotection:

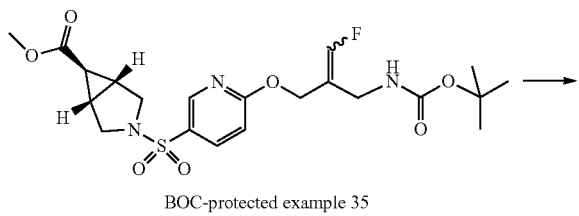

BOC-protected example 35

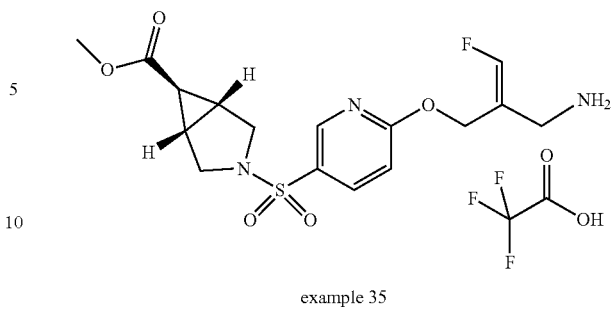

example 35

The BOG-protected example 35 (50 mg; 0.10 mmol) was dissolved in DCM (5 mL; 5) and TFA (20 µL; 0.21 mmol; A) was added. The reaction mixture was stirred at RT (T) overnight (t) and concentrated under reduced pressure. The residue was dissolved in MeOH (2 mL) and purified by RP-HPLC (ACN/water+TFA) to give example 35.

Yield: 7 mg (14%), ESI-MS: m/z=385 [M+H]⁺, R$_t$ (HPLC): 0.44 min (HPLC-1)

The following example was prepared in analogy to the above described procedure using the corresponding starting materials. Details for the two steps are given in the column synthesis comment, the retention-time and mass (ESI-MS, m/z=[M+H]⁺) determined by HPLC-MS are given in the columns RT and MS.

| Ex. | structure |
|---|---|
| 36 | 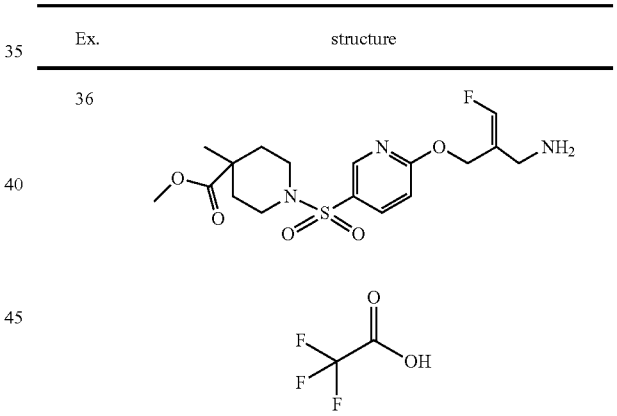 |

| | | Substitution | | | BOC deprotection | | |
|---|---|---|---|---|---|---|---|
| Ex. | starting materials | R$_t$ [min] (HPLC method) | MS | synthesis comment | R$_t$ [min] (HPLC method) | MS | synthesis comment |
| 36 | III.3; IV.1 | 0.72 (HPLC-1) | 502 | S: Tol B: 1.00 eq T: RT t: 1 h | 0.50 (HPLC-1) | 402 | S: DCM A: 4 eq TFA T: RT t: 2 h |

Example 37: 1-[6-((Z)-Aminomethyl-3-fluoro-allyloxy)-pyridine-3-sulfonyl]-piperidine-4-carboxylic acid methylamine trifluoroacetate Substitution:

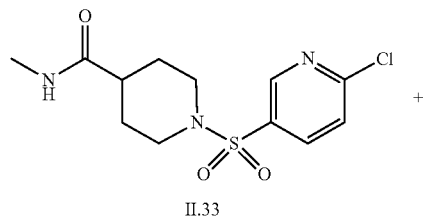

II.33

+

To a mixture of alcohol IV.1 (70 mg; 0.34 mmol) in THF (2.5 mL; S) was added sodium hydride (55%; 30 mg; 0.68 mmol; B) at RT (T) and the resulting mixture was stirred for 10 min. Then intermediate 11.33 (108 mg; 0.34 mmol) was added and the reaction mixture was stirred at RT (T) overnight (t). The reaction mixture was purified by RP-HPLC (ACN/water+TFA) to obtain the BOC-protected example 37.

Yield: 95 mg (57%), ESI-MS: m/z=487 [M+H]$^+$, R$_t$ (HPLC): 0.64 min (HPLC-2)

BOC Deprotection:

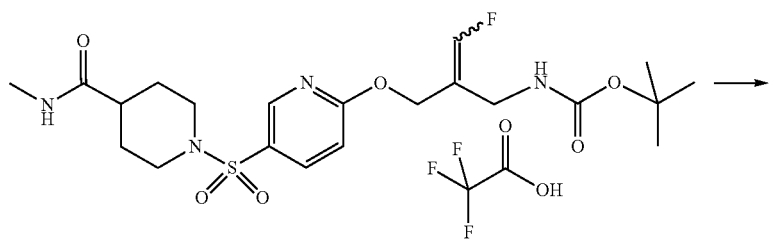

BOC-protected example 37

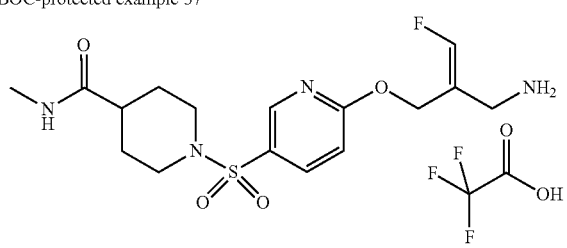

example 37

-continued

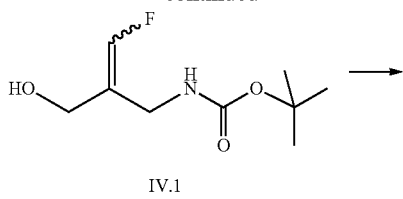

IV.1

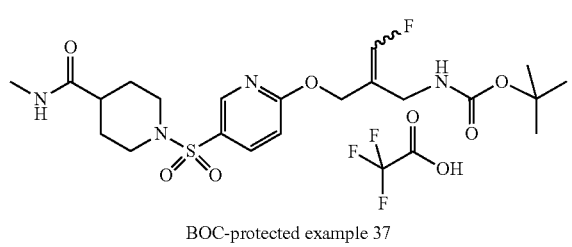

BOC-protected example 37

The BOC-protected example 37 (95 mg; 0.19 mmol) was dissolved in DCM (4 mL; S) and TFA (1.5 mL; 19.47 mmol; A) was added. The reaction mixture was stirred at RT (T) for 3 h 20 min (t) and purified by RP-HPLC (ACN/water+TFA) to give example 37.

Yield: 36 mg (21%), ESI-MS: m/z=387 [M+H]$^+$, R$_t$ (HPLC): 0.69 min (HPLC-5)

The following examples (example number given in column Ex.) were prepared in analogy to the above described procedure using the corresponding starting materials. Details for the two steps are given in the column synthesis comment, the retention-time and mass (ESI-MS, m/z=[M+H]$^+$) determined by HPLC-MS are given in the columns RT and MS.

| Ex. | structure |
|---|---|
| 38 | 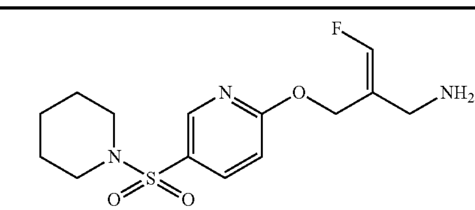 |

| Ex. | structure | | Ex. | Substitution starting materials | Substitution R_t [min] (HPLC method) | Substitution MS | Substitution synthesis comment | BOC deprotection R_t [min] (HPLC method) | BOC deprotection MS | BOC deprotection synthesis comment |
|---|---|---|---|---|---|---|---|---|---|---|
| 39 | 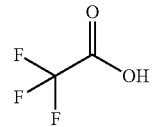 | | 38 | II.34; IV.1 | — | — | S: THF B: 2.00 eq T: RT t: 2 h; BOC-protected intermediate not isolated | 0.42 (HPLC-1) | 330 | S: DCM A: 41 eq TFA T: RT t: 2 h |
| | | | 39 | II.35; IV.1 | 0.61 (HPLC-2) | 459 | S: THF B: 2.00 eq T: RT t: overnight | 0.65 (HPLC-5) | 359 | S: DCM A: 28 eq TFA T: RT t: 1 h |
| 40 | 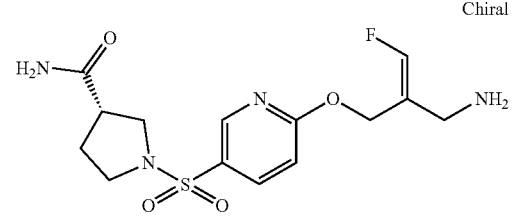 [SMILES: NC/C(=C/F)COc1ccc(S(=O)(=O)N2CC[C@H](C(N)=O)C2)cn1] | | 40 | II.36; IV.1 | — | — | S: THF B: 2.00 eq T: RT t: 2 h; BOC-protected intermediate not isolated | 0.39 (HPLC-1) | 360 | S: DCM A: 46 eq TFA T: RT t: 2 h |
| | | | 41 | II.37; IV.1 | 0.68 (HPLC-2) | 460 | S: THF B: 2.00 eq T: RT t: overnight | 0.72 (HPLC-5) | 360 | S: DCM A: 19 eq TFA T: RT t: 2 h |
| 41 | 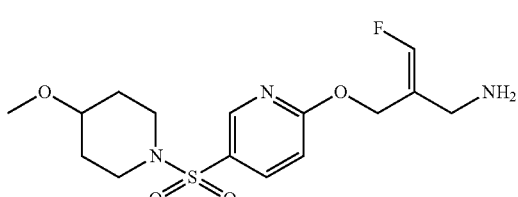 | | 42 | II.38; IV.1 | 0.75 (HPLC-2) | 514 | S: THF B: 2.00 eq T: RT t: overnight | 0.80 (HPLC-5) | 414 | S: DCM A: 24 eq TFA T: RT t: 2 h |
| 42 | 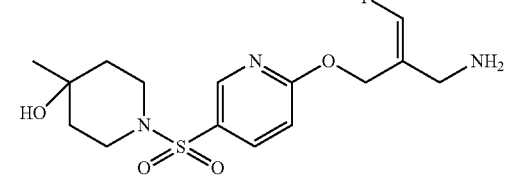 | | | | | | | | | |

Example 43: 4 (S)-1-[6-(Z)-2-Aminomethyl-3-fluoro-allyloxy]-pyridine-3-sulfonyl]-pyrrolidin-3-ol trifluoroacetate Substitution:

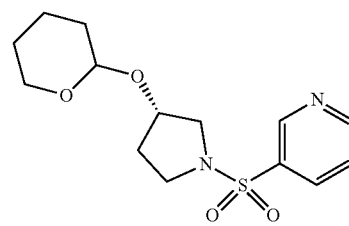

II.40

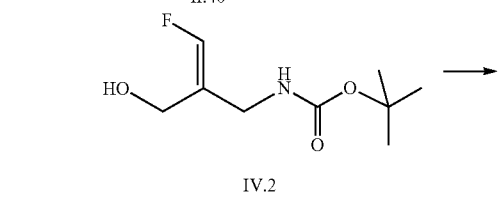

IV.2

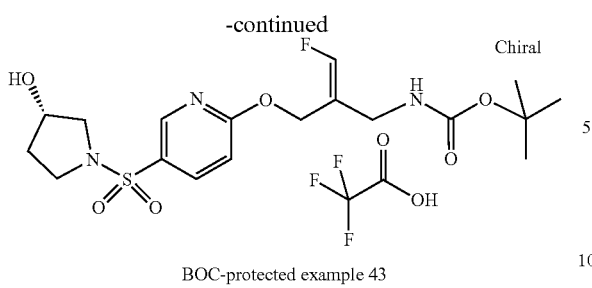

BOC-protected example 43

A solution of alcohol IV.2 (39 mg; 0.19 mmol) in absolute THF (1.0 mL; S) was cooled to 0° C. and sodium tert-butoxide (2 M in THF; 100 µL; 0.20 mmol) was added. After 5 min stirring at 0° C., intermediate 11.40 (66 mg; 0.19 mmol) was added to the reaction mixture. The reaction mixture was warmed to RT, stirred at RT for 33 min and purified by RP-HPLC (ACN/water+TFA) to obtain the BOC-protected example 43.

Yield: 59 mg (72%), ESI-MS: m/z=432 [M+H]$^+$, R$_t$ (HPLC): 1.15 min (HPLC-5)

BOC Deprotection:

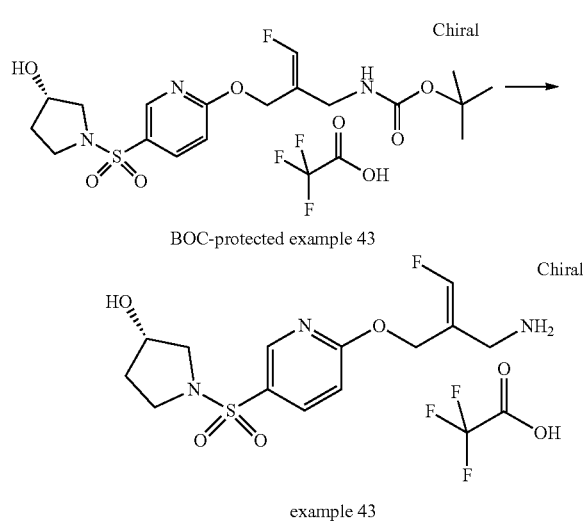

The BOC-protected example 43 (58 mg; 0.13 mmol) was diluted with DCM (2 mL) and TFA (104 µL; 1.34 mmol) was added. The reaction mixture was stirred at RT (T) for 1 h 50 min (t) and purified by RP-HPLC (ACN/water+TFA) to give example 43.

Yield: 33 mg (55%), ESI-MS: m/z=332 [M+H]$^+$, R$_t$ (HPLC): 0.29 min (HPLC-5)

Intermediate V.1: {1-[6-(2-Aminomethyl-3-fluoro-allyloxy)-pyridine-3-sulfonyl]-piperidin-4-yl}-acetic acid methyl ester (E/Z-mixture)

The alcohol IV.1 (0.95 g; 4.62 mmol) was dissolved in toluene (30 mL) and sodium tert-butoxide (0.44 g; 4.62 mmol) and intermediate 111.4 (1.46 g; 4.62 mmol) were added. The reaction mixture was stirred at RT for 2 h, diluted with toluene (30 ml) and extracted with water two times. The organic phase was dried with Na$_2$SO$_4$ and evaporated under reduced pressure. The residue was purified by silica gel chromatography (cyclohexane/EtOAC) to provide intermediate V.1.

Yield: 1.85 g (80%), ESI-MS: m/z=502 [M+H]$^+$, R$_t$ (HPLC): 0.72 mi (HPLC-1)

The following intermediates were prepared in analogy to the above described procedure using the alcohol IVA and the corresponding starting material. For changes from this procedure, see "synthesis comment".

| intermediate | structure | starting material | R$_t$ [min] (HPLC method) | MS | synthesis comment |
|---|---|---|---|---|---|
| V.2 | 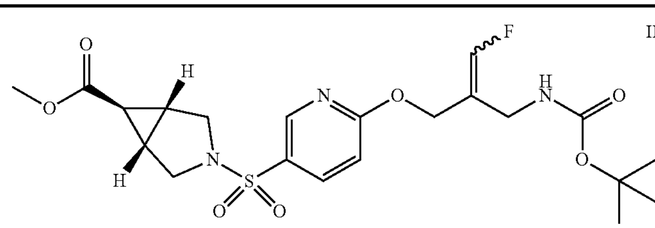 | III.2 | 0.69 (HPLC-1) | 486 | 1 h |

| intermediate | structure | starting material | R$_t$ [min] (HPLC method) | MS | synthesis comment |
|---|---|---|---|---|---|
| V.3 | 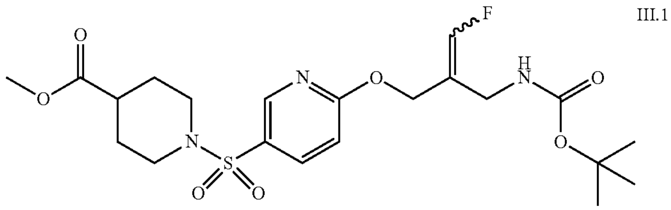 | III.1 | 0.71 (HPLC-1) | 488 | workup: recrystallization with PE/EtOAC (3:1) |
| V.4 | 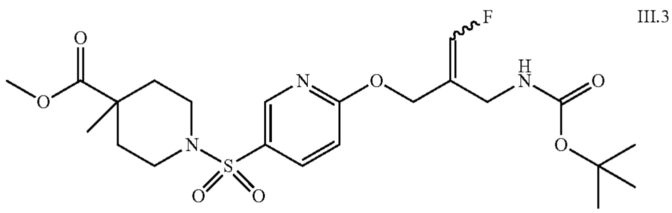 | III.3 | 0.72 (HPLC-1) | 502 | 70 min |

Intermediate VI.1: {1-[6-(2-Aminomethyl-3-fluoro-allyloxy)-pyridine-3-sulfonyl]-piperidin-4-yl}-acetic acid (E/Z-mixture)

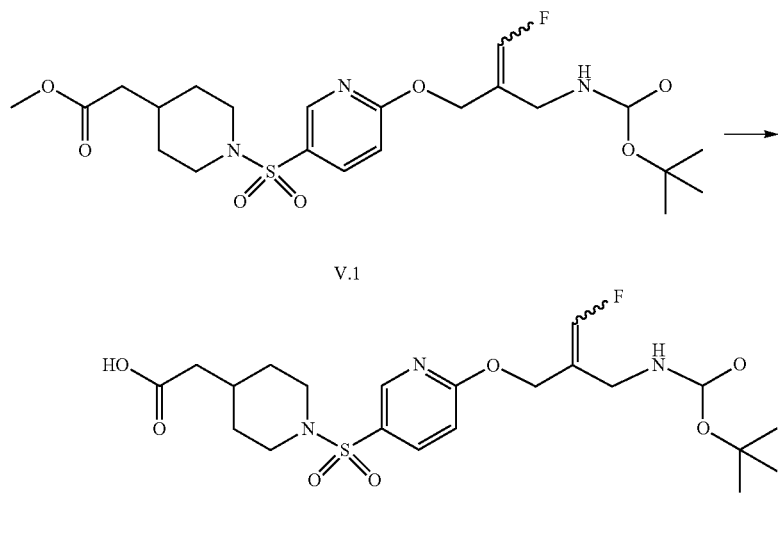

Intermediate V.1 (1.85 g; 3.69 mmol) was dissolved in MeOH (70 mL) and aq. NaOH (1 N; 22.13 mL; 22.13 mmol) was added. The reaction mixture was stirred at RT for 10 min, then acidified with citric acid (10%) and MeOH was evaporated under reduced pressure. The residue was cooled to 5° C., the precipitate was filtered, washed with water (10 mL) and dried at 40° C. to give intermediate VI.1.

Yield: 1.31 g (73%), ESI-MS: m/z=488 [M+H]$^+$, R$_t$ (HPLC): 0.62 min (HPLC-1)

The following intermediates were prepared in analogy to the above described procedure using the corresponding starting material. For changes from this procedure, see "synthesis comment".

| intermediate | structure | starting material | R_t [min] (HPLC method) | MS | synthesis comment |
|---|---|---|---|---|---|
| VI.2 | 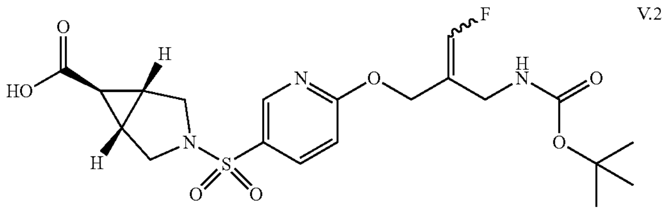 | V.2 | 0.62 (HPLC-1) | 472 | 4 eq NaOH; overnight |
| VI.3 | 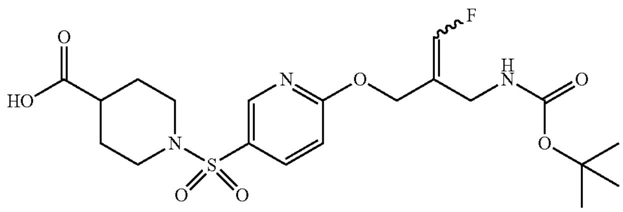 [SMILES: CC(C)(C)OC(=O)NCC(=CF)COc1ccc(S(=O)(=O)N2CCC(C(=O)O)CC2)cn1] | V.3 | 0.62 (HPLC-1) | 474 | 4 eq NaOH; 3 h |
| VI.4 | 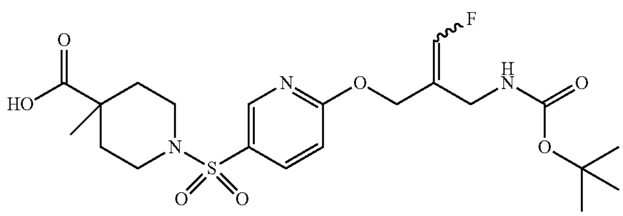 [SMILES: CC(C)(C)OC(=O)NCC(=CF)COc1ccc(S(=O)(=O)N2CCC(C)(C(=O)O)CC2)cn1] | V.4 | 0.63 (HPLC-1) | 487 | 7.2 eq NaOH; 2 d |
Example 44 {1-[6-((Z)-2-Aminomethyl-3-fluoro-allyloxy)-piperidine-3-sulfonyl]piperidin-4-yl}-acetic acid trifluoroacetate
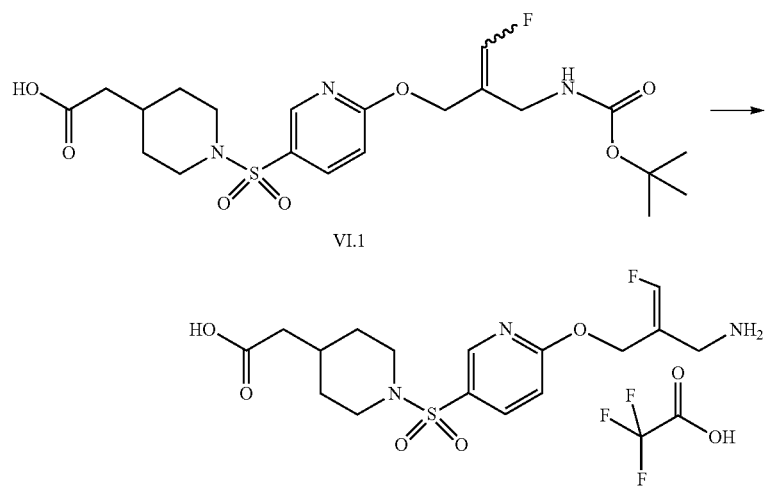
VI.1
example 44

Intermediate VI.1 (50 mg; 0.10 mmol) was dissolved in hydrogen chloride (4 N in 1,4-dioxane; 1.5 mL; 6.00 mmol) and stirred at RT for 70 min. The reaction mixture was evaporated in vacuo. The residue was dissolved in MeOH (3 mL) and purified by RP-HPLC (ACN/water+TFA) to provide example 44.

Yield: 12 mg (23%), ESI-MS: m/z=388 [M+H]$^+$, R$_t$ (HPLC): 0.41 min (HPLC-1)

Example 45 trans-3-[6-((Z)-2-Aminomethyl-3-fluoro-allyloxy)-pyridine-3-sulfonyl]-3-aza-bicyclo[3.1.0]hexane-6-carboxylic acid trifluoroacetate

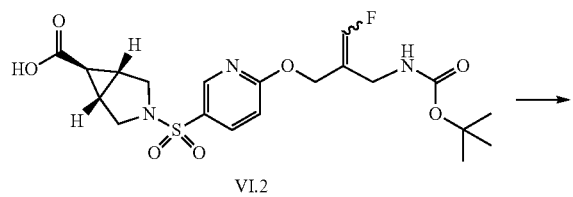

VI.2

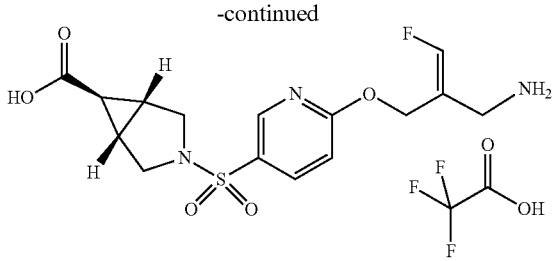

example 45

To a solution of intermediate VI.2 (50 mg; 0.11 mmol) in DCM (10 mL) was added TFA (50 mg; 0.42 mmol). The reaction mixture was stirred at RT for 50 min, evaporated in vacuo and the residue purified by RP-HPLC (ACN/water+TFA) to provide example 45.

Yield: 11 mg (21%), ESI-MS: m/z=372 [M+H]$^+$, R$_t$ (HPLC): 0.41 min (HPLC-1)

The following examples were prepared in analogy to the above described procedure using the corresponding starting material. For changes from this procedure, see "synthesis comment".

| example | structure | starting material | R$_t$ [min] (HPLC method) | MS | synthesis comment |
|---|---|---|---|---|---|
| 46 | ![structure] | VI.3 | 0.43 (HPLC-1) | 374 | 2 h |
| 47 | ![structure] | VI.4 | 0.74 (HPLC-4) | 388 | 15.5 h |

Intermediate VII.1: (3-Fluoro-2-{5-[4-methyl-4-(tetrahydro-pyran-4-ylcarbamoyl)-piperidine-1-sulfonyl]-pyridine-2-yloxymethyl}-allyl)-carbamic acid tert-butyl ester (E/Z-mixture) trifluoroacetate

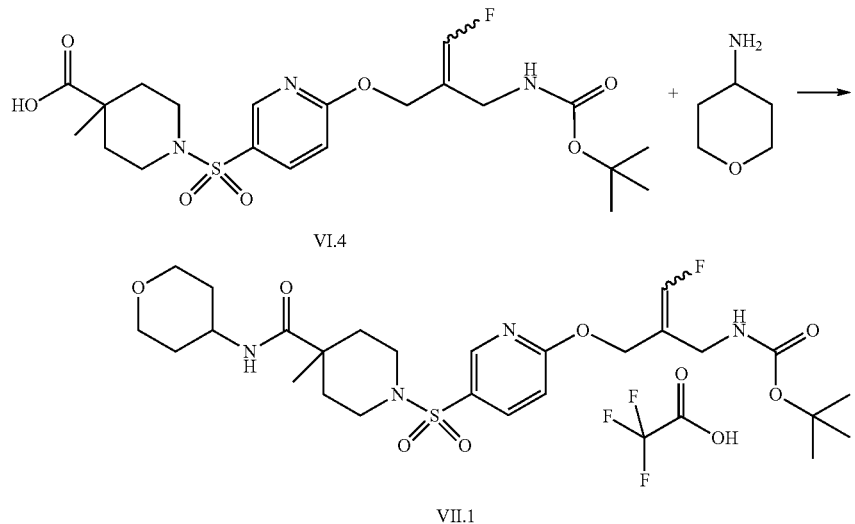

Intermediate VI.4 (40 mg; 0.08 mmol) was dissolved in DMF (2.00 mL) and TEA (46 µL; 0.33 mmol) and TCFH (23 mg; 0.08 mmol) were added. The reaction mixture was stirred at RT for 10 min and 4-aminotetrahydropyran (20 mg; 0.20 mmol) was added. The reaction mixture was stirred at RT overnight, then acidified with TFA (aq.; 50%) and purified by RP-HPLC (ACN/water+TFA) to provide intermediate VII.1.

Yield: 22 mg (47%), ESI-MS: m/z=471 [M+H]$^+$, $R_t$ (HPLC): 1.05 min (HPLC-5)

The following intermediates were prepared in analogy to the above described procedure using the intermediate VI.4 and the corresponding starting material. For changes from this procedure, see "synthesis comment".

| intermediate | structure | starting material | $R_t$ [min] (HPLC method) | MS | synthesis comment |
|---|---|---|---|---|---|
| VII.2 | 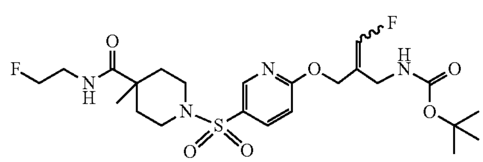 [SMILES: CC(C)(C)OC(=O)NCC(=CF)COc1ccc(S(=O)(=O)N2CCC(C)(C(=O)NCCF)CC2)cn1] | F-CH2CH2-NH2 · HCl | 1.00 (HPLC-3) | 433 | 2 eq Amin; 6 eq TEA; 3 h; purification: RP-HPLC (ACN/water + NH$_4$OH) |
| VII.3 | 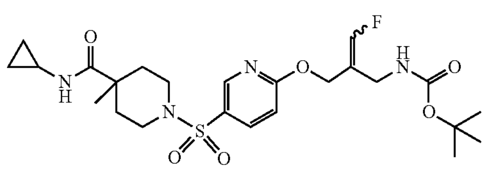 [SMILES: CC(C)(C)OC(=O)NCC(=CF)COc1ccc(S(=O)(=O)N2CCC(C)(C(=O)NC3CC3)CC2)cn1] | cyclopropyl-NH2 | 1.02 (HPLC-3) | 427 | 2 eq Amin; purification: RP-HPLC (ACN/water + NH$_4$OH) |

Intermediate VII.4: {2-[5-(4-Carbamoyl-4-methyl-piperidine-1-sulfonyl)-pyridin-2-yloxymethyl]-3-fluoro-allyl}-carbamic acid tert-butyl ester (E/Z-mixture)

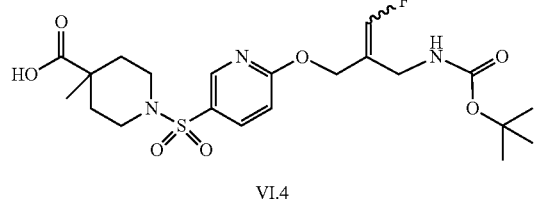

VI.4

+

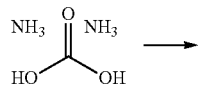

-continued

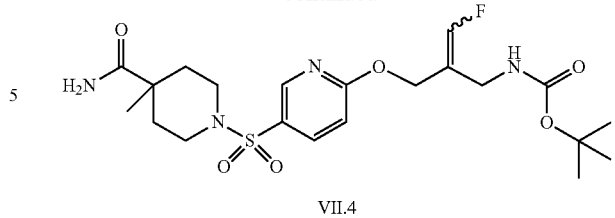

VII.4

To a solution of intermediate VI.4 (30 mg; 0.06 mmol) in DMF (2 mL) was added TEA (69 µL; 0.49 mmol) and HATU (23 mg; 0.06 mmol) and the reaction mixture was stirred at RT for 10 min. Ammonium carbonate (30 mg; 0.31 mmol) was added to the reaction mixture and it was stirred at RT overnight. The reaction mixture was purified by RP-HPLC (ACN/water+NH$_4$OH) to provide intermediate VII.4.

Yield: 16 mg (55%), ESI-MS: m/z=387 [M+H]$^+$, R$_t$ (HPLC): 0.96 min (HPLC-3)

The following intermediates were prepared in analogy to the above described procedure using the intermediate VI.1 and the corresponding starting materials. For changes from this procedure, see "synthesis comment".

| intermediate | structure | starting material | R$_t$ [min] (HPLC method) | MS | synthesis comment |
|---|---|---|---|---|---|
| VII.5 | | 0.5M NH3 in 1,4-dioxane | 0.58 (HPLC-1) | 487 | 1.1 eq HATU; 2.0 eq TEA; 100 min; workup: aq. extraction with EtOAc; acidic RP-HPLC |
| VII-6 | 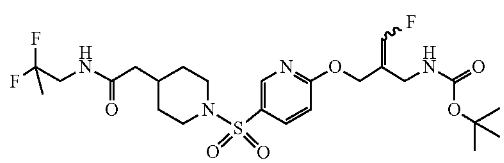 [SMILES: CC(F)(F)CNC(=O)CC1CCN(S(=O)(=O)c2ccc(OCC(=CF)CNC(=O)OC(C)(C)C)nc2)CC1] | | 0.83 (HPLC-7) | 565 | 1.5 eq Amin; 4.25 eq TEA |
| VII-7 | 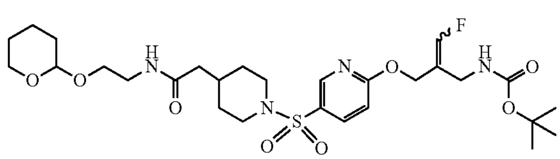 [SMILES: CC(C)(C)OC(=O)NCC(=CF)COc1ccc(S(=O)(=O)N2CCC(CC(=O)NCCOC3CCCCO3)CC2)cn1] | | 0.84 (HPLC-7) | 615 | 1.5 eq Amin; 4.25 eq TEA |
| VII-8 | 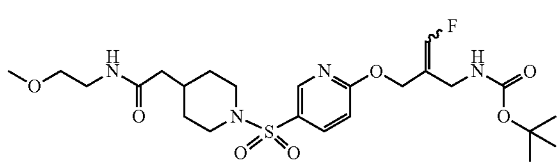 [SMILES: COCCNC(=O)CC1CCN(S(=O)(=O)c2ccc(OCC(=CF)CNC(=O)OC(C)(C)C)nc2)CC1] | | 0.76 (HPLC-7) | 545 | 1.5 eq Amin; 4.25 eq TEA |
| VII-9 | 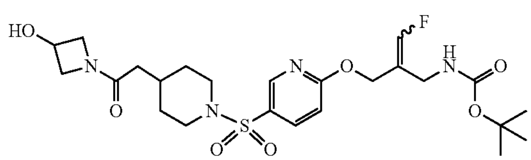 [SMILES: CC(C)(C)OC(=O)NCC(=CF)COc1ccc(S(=O)(=O)N2CCC(CC(=O)N3CC(O)C3)CC2)cn1] | | 0.70 (HPLC-7) | 543 | 1.5 eq Amine; 4.25 eq TEA |

Example 48: 1-[6-((Z)-2-Aminomethyl-3-fluoro-allyloxy)-pyridine-3-sulfonyl]-4-methyl-piperidine-4-carboxylic acid (tetrahydropyran-4-yl)-amide trifluoroacetate

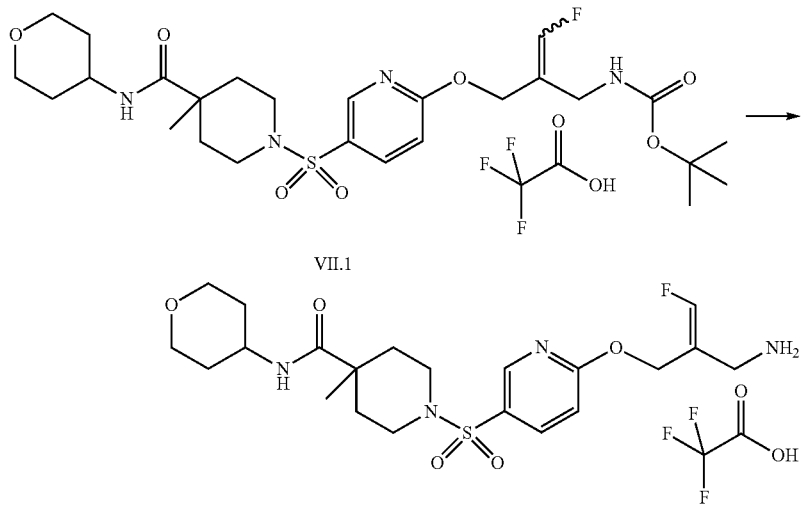

example 48

A solution of intermediate VII.1 (22 mg; 0.04 mmol) and TFA (1.00 mL; 12.96 mmol) in DCM (1 mL) was stirred at RT for 2 h, then evaporated to dryness under reduced pressure, acidified with TFA (50%) and purified by RP-HPLC (ACN/water+TFA) to provide example 48.

Yield: 8 mg (36%), ESI-MS: m/z=471 [M+H]+, Rc (HPLC): 0.75 min (HPLC-5)

The following examples were prepared in analogy to the above described procedure using the corresponding starting material. For changes from this procedure, see "synthesis comment".

| example | structure | starting material | R$_t$ [min] (HPLC method) | MS | synthesis comment |
|---|---|---|---|---|---|
| 49 | 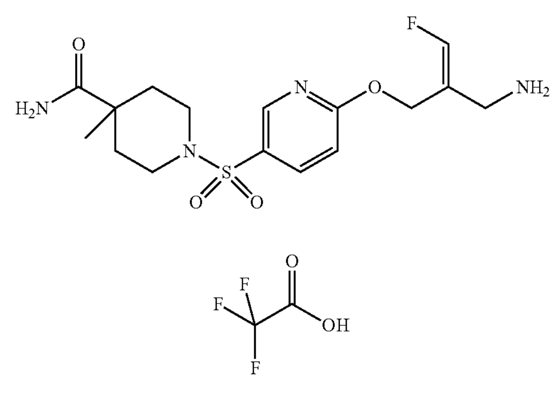 | VII.4 | 0.70 (HPLC-5) | 387 | exc. TFA |
| 50 | 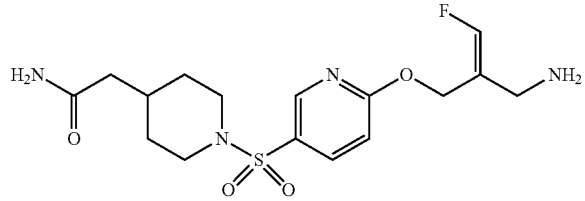 [SMILES: NC/C(=C/F)COc1ccc(S(=O)(=O)N2CCC(CC(N)=O)CC2)cn1] | VII.5 | 0.41 (HPLC-1) | 386 | exc. TFA; 105 min |

| example | structure | starting material | $R_t$ [min] (HPLC method) | MS | synthesis comment |
|---|---|---|---|---|---|
| 51 | 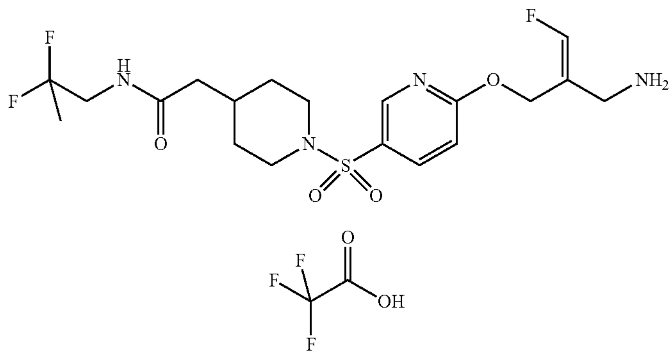 | VII.6 | 0.49 (HPLC-8) | 465 | exc. TFA; 1 h |
| 52 | 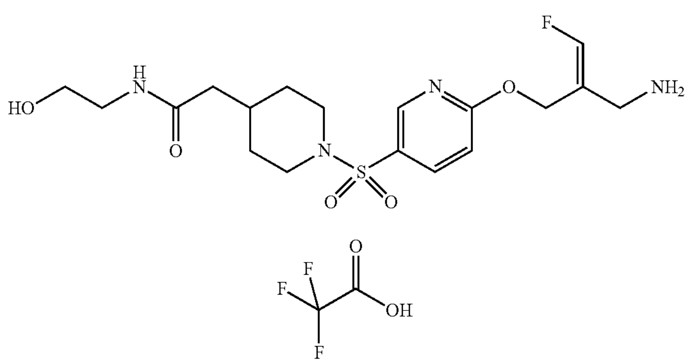 | VII.7 | 0.38 (HPLC-8) | 431 | exc. TFA; 1 h |
| 53 | 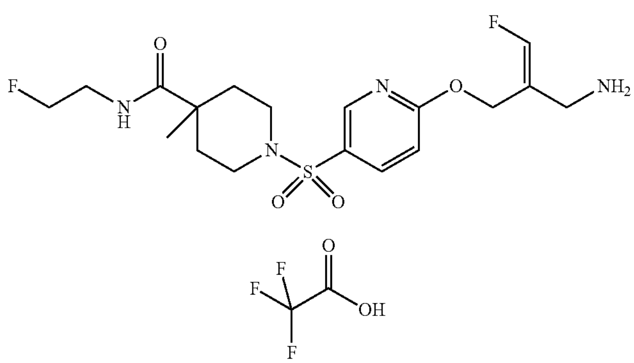 | VII.2 | 0.75 (HPLC-5) | 433 | exc. TFA |
| 54 | 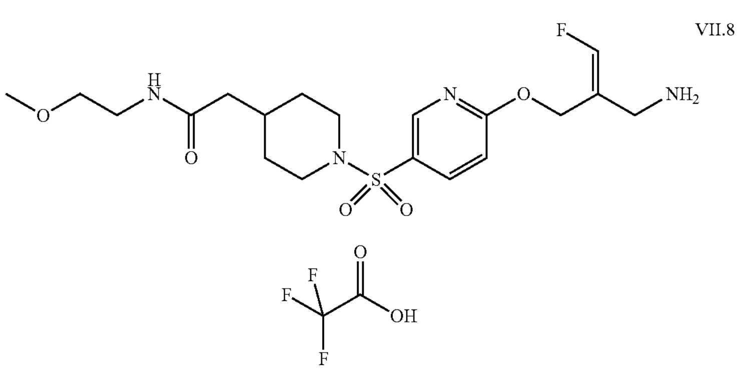 | VII.8 | 0.43 (HPLC-8) | 445 | exc. TFA; 1 h |

| example | structure | starting material | R_t [min] (HPLC method) | MS | synthesis comment |
|---|---|---|---|---|---|
| 55 | 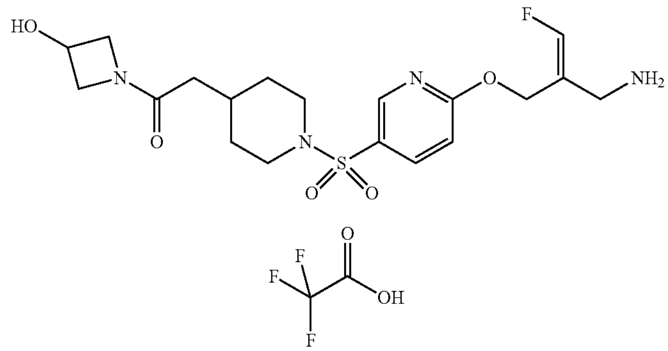 | VII.9 | 0.40 (HPLC-8) | 443 | exc. TFA; 1 h |
| 56 | 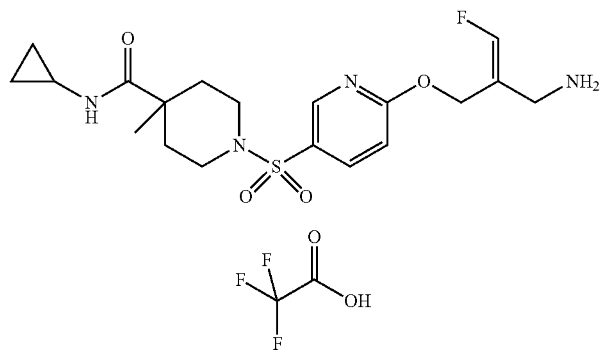 | VII.3 | 0.76 (HPLC-5) | 427 | exc. TFA; |

The invention claimed is:

1. A compound of formula (I)

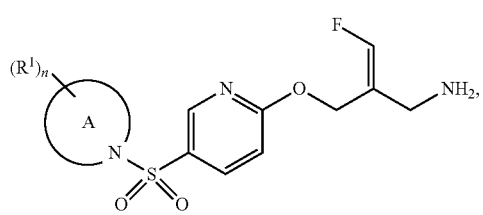

wherein
ring A is selected from the group consisting of:

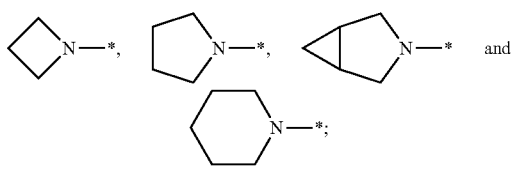

$R^1$ is selected from the group consisting of H, F, Cl, Br, CN, —OH, $C_{1-4}$-alkyl, —O—($C_{1-4}$-alkyl), —$(CH_2)_m$—COOH, —$(CH_2)_m$—C(=O)—O—($C_{1-4}$-alkyl), —$(CH_2)_m$—C(=O)-heterocyclyl, —$(CH_2)_m$—C(=O)—$NH_2$, —$(CH_2)_m$—C(=O)—NH—($C_{1-4}$-alkyl), —$(CH_2)_m$—C(=O)—N($C_{1-4}$-alkyl)$_2$, —C(=O)—NH—$C_{3-6}$-cycloalkyl, —C(=O)—NH-heterocyclyl, $(CH_2)_m$—NH—C(=O)—($C_{1-3}$-alkyl), —N($C_{1-3}$-alkyl)-C(=O)—($C_{1-4}$-alkyl), —N($C_{1-3}$-alkyl)-C(=O)—$NH_2$, —NH—C(=O)—NH—($C_{1-4}$-alkyl), heterocyclyl and phenyl,
wherein each alkyl group or sub-group is optionally substituted with 1 or more F atoms or with one OH or —O—($C_{1-3}$-alkyl) group; and
wherein each heterocyclyl is selected from the group consisting of azetidinyl, imidazolidinyl, piperidinyl, tetrahydropyranyl, morpholinyl, and each heterocyclyl is optionally substituted with one or two groups independently selected from the group consisting of OH, oxo, $C_{1-3}$-alkyl, —C(=O)—$CH_3$ and —C(=O)-cyclopropyl group;
wherein multiple $R^1$ may be identical or different, if n is 2; and
n is an integer selected from 1 and 2; and
m is an integer selected from 0, 1 and 2; and
wherein in any definition mentioned hereinbefore, if not specified otherwise, any alkyl group or sub-group may be straight-chained or branched and is optionally substituted with 1 or more F atoms,
or a salt thereof.

2. The compound of formula (I) according to claim 1, wherein
$R^1$ is selected from the group consisting of:
H, F, —OH, $C_{1-2}$-alkyl, —O—($C_{1-2}$-alkyl), —$(CH_2)_m$—COOH, —$(CH_2)_m$—C(=O)—O—($C_{1-2}$-alkyl), —$(CH_2)_m$—C(=O)-heterocyclyl, —$(CH_2)_m$—C(=O)—$NH_2$, —$(CH_2)_m$—C(=O)—NH—($C_{1-4}$-alkyl), —$(CH_2)_m$—C(=O)—N($C_{1-2}$-alkyl)$_2$, —C(=O)—NH-cyclo-propyl, —C(=O)—NH-heterocyclyl, —(CH$_2$)$_m$—NH—C(=O)—(C$_{1-2}$-alkyl) and -heterocyclyl, wherein each alkyl group or sub-group is optionally substituted with 1 or more F atoms or with one OH or —O—(C$_{1-2}$-alkyl) group; and wherein each heterocyclyl is selected from the group consisting of azetidinyl, imidazolidinyl, piperidinyl, tetrahydropyranyl, morpholinyl, and each heterocyclyl is optionally substituted with one or two groups independently selected from the group consisting of OH, oxo, C$_{1-2}$-alkyl, —C(=O)—CH$_3$ and —C(=O)-cyclopropyl;

wherein m is 0 or 1; and wherein multiple R$^1$ may be identical or different, if n is 2;

or a salt thereof.

3. The compound of formula (I) according to claim 2, wherein

R$^1$ is selected from the group consisting of:

H, —OH, —CH$_3$, CF$_3$, —O—CH$_3$, —(CH$_2$)$_m$—COOH, —(CH$_2$)$_m$—C(=O)—O—(CH$_3$), (CH$_2$)$_m$—C(=O)-heterocyclyl, —(CH$_2$)$_m$—C(=O)—NH$_2$, —C(=O)—NH—(C$_{1-4}$-alkyl), —C(=O)—N(CH$_3$)$_2$, —C(=O)—NH-cyclopropyl, —C(=O)—NH-tetrahydropyranyl, —(CH$_2$)$_m$—NH—C(=O)—(C$_{1-2}$-alkyl) and 3-methyl-2-oxo-imidazolidin-1-yl, wherein each alkyl group or sub-group is optionally substituted with 1 to 3 F atoms or with one OH or —O—CH$_3$ group;

wherein each heterocyclyl is selected from the group consisting of azetidinyl and morpholinyl, and each heterocyclyl is optionally substituted with one OH group;

wherein m is 0 or 1; and wherein if n is 2, multiple R$^1$ may be identical or different, and the second R$^1$ group is selected from the group consisting of CH$_3$ and CF$_3$;

or a salt thereof.

4. The compound of formula (I) according to claim 1, wherein ring A is

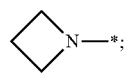

R$^1$ is selected from the group consisting of H, F, —OH, C$_{1-4}$-alkyl, —O—(C$_{1-3}$-alkyl), —C(=O)—NH$_2$, —C(=O)—NH—(C$_{1-4}$-alkyl), —C(=O)—N(C$_{1-4}$-alkyl)$_2$ and heterocyclyl, wherein each alkyl group or sub-group is optionally substituted with 1 or more F atoms or with one OH or —O—(C$_{1-3}$-alkyl) group;

wherein each heterocyclyl is selected from the group consisting of azetidinyl, and piperidinyl, and each heterocyclyl is optionally substituted with one C$_{1-3}$-alkyl, —C(=O)—CH$_3$ or —C(=O)-cyclopropyl group; and wherein, if n is 2, multiple R$^1$ may be identical or different, and the second R$^1$ group is CH$_3$; and n is an integer selected from 1 and 2;

or a salt thereof.

5. The compound of formula (I) according to claim 1, wherein ring A is

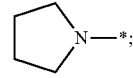

R$^1$ is selected from the group consisting of H, F, —OH, —O—(C$_{1-2}$-alkyl), —C(=O)-heterocyclyl, —(CH$_2$)$_m$—C(=O)—NH$_2$, —(CH$_2$)$_m$—C(=O)—NH—(C$_{1-4}$-alkyl), —(CH$_2$)$_m$—C(=O)—N(C$_{1-4}$-alkyl)$_2$, —(CH$_2$)$_m$—NH—C(=O)—(C$_{1-3}$-alkyl) and —N(C$_{1-3}$-alkyl)-C(=O)—(C$_{1-4}$-alkyl), wherein each alkyl group or sub-group is optionally substituted with 1 or more F atoms or with one OH or —O—(C$_{1-3}$-alkyl) group; and wherein each heterocyclyl is selected from the group consisting of azetidinyl, imidazolidinyl, piperidinyl, tetrahydropyranyl and morpholinyl, and each heterocyclyl is optionally substituted with one CH$_3$ group;

n is 1; and m is an integer selected from 0 and 1;

or a salt thereof.

6. The compound of formula (I) according to claim 1, wherein ring A is

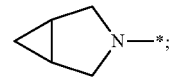

R$^1$ is selected from the group consisting of H, —(CH$_2$)$_m$—COOH, —(CH$_2$)$_m$—C(=O)—O—(C$_{1-3}$-alkyl), —C(=O)-heterocyclyl, —(CH$_2$)$_m$—C(=O)—NH$_2$, —(CH$_2$)$_m$—C(=O)—NH—(C$_{1-3}$-alkyl) and —(CH$_2$)$_m$—C(=O)—N(C$_{1-3}$-alkyl)$_2$, wherein each alkyl group or sub-group is optionally substituted with 1 or more F atoms or with one OH or —O—CH$_3$ group; and wherein each heterocyclyl is selected from the group consisting of azetidinyl, piperidinyl, tetrahydropyranyl and morpholinyl, and each heterocyclyl is optionally substituted with one CH$_3$ group;

n is 1; and m is an integer selected from 0 and 1;

or a salt thereof.

7. The compound of formula (I) according to claim 1, wherein ring A is

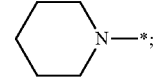

R$^1$ is selected from the group consisting of H, —OH, C$_{1-2}$-alkyl, —O—(C$_{1-2}$-alkyl), —(CH$_2$)$_m$—COOH, —(CH$_2$)$_m$—C(=O)—O—(C$_{1-2}$-alkyl), —(CH$_2$)$_m$—C(=O)-heterocyclyl, —(CH$_2$)$_m$—C(=O)—NH$_2$, —(CH$_2$)$_m$—C(=O)—NH—(C$_{1-4}$-alkyl), —(CH$_2$)$_m$—C(=O)—N(C$_{1-2}$-alkyl)$_2$, —C(=O)—NH-cyclopropyl, —C(=O)—NH-heterocyclyl, —(CH$_2$)$_m$—NH—C(=O)—(C$_{1-2}$-alkyl), and heterocyclyl, wherein each alkyl group or sub-group is optionally substituted with 1 or more F atoms or with one OH or —O—CH$_3$ group;

wherein each heterocyclyl is selected from the group consisting of azetidinyl, imidazolidinyl, tetrahydropyranyl and morpholinyl, and each heterocyclyl is optionally substituted with one or two groups independently selected from the group consisting of OH, oxo, C$_{1-2}$-alkyl and —C(=O)—CH$_3$; and wherein multiple R$^1$ may be identical or different, if n is 2;

n is an integer selected from 1 and 2; and m is an integer selected from 0 and 1;

or a salt thereof.

8. The compound of formula (I) according to claim 7, wherein

R$^1$ is selected from the group consisting of:
H, —OH, CH$_3$, —O—CH$_3$, —(CH$_2$)$_m$—COOH, —(CH$_2$)$_m$—C(=O)—O—CH$_3$, —(CH$_2$)$_m$—C(=O)-heterocyclyl, —(CH$_2$)$_m$—C(=O)—NH$_2$, —(CH$_2$)$_m$—C(=O)—NH—(C$_{1-3}$-alkyl), —(CH$_2$)$_m$—C(=O)—N(CH$_3$)$_2$, —C(=O)—NH-cyclopropyl, —C(=O)—NH-heterocyclyl, —(CH$_2$)$_m$—NH—C(=O)—CH$_3$ and -heterocyclyl, wherein each alkyl group or sub-group is optionally substituted with 1 to 3 F atoms or with one OH or —O—CH$_3$ group;

wherein each heterocyclyl is selected from the group consisting of azetidinyl, imidazolidinyl and tetrahydropyranyl, and each heterocyclyl is optionally substituted with one or two groups independently selected from the group consisting of OH, oxo, CH$_3$ and —C(=O)—CH$_3$, wherein m is 0 or 1; and wherein, if n is 2, multiple R$^1$ may be identical or different and the second R$^1$ group is selected from the group consisting of CH$_3$ and CF$_3$;

or a salt thereof.

9. The compound of formula (I) according to claim 1 selected from the group consisting of:

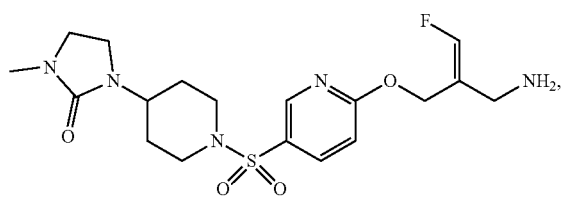

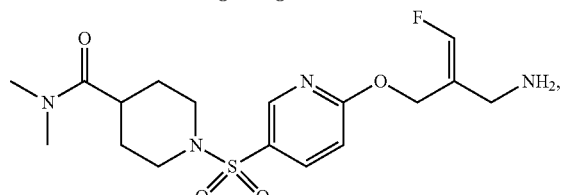

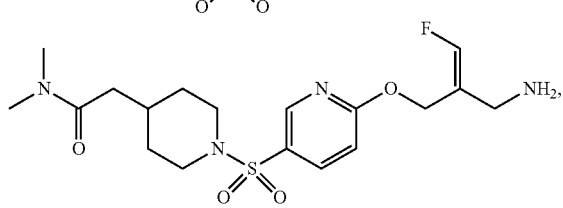

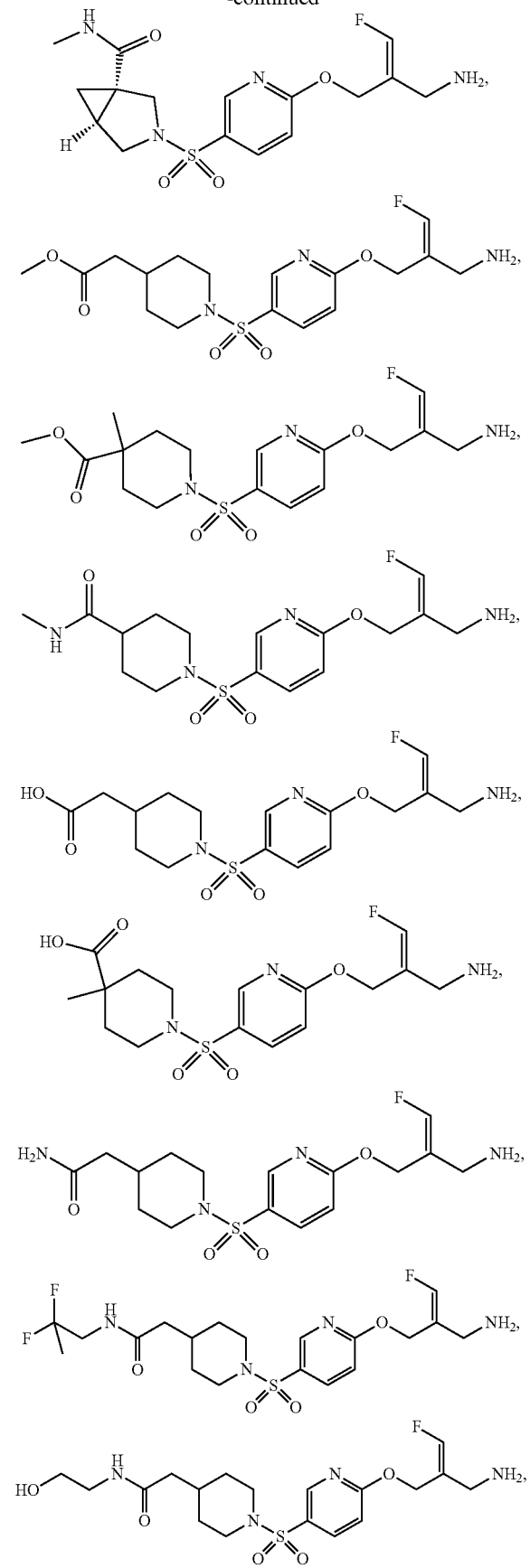

-continued

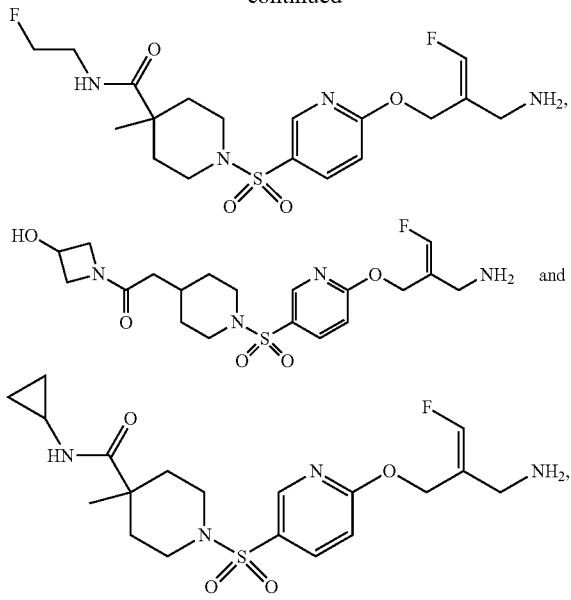

or a salt thereof.

10. A pharmaceutically acceptable salt of a compound according to claim 1.

11. A method for treating melanoma, lymphoma, NASH (non-alcoholic steatohepatitis), pulmonary fibrosis, retinopathy, nephropathy or stroke, comprising administering a pharmaceutically effective amount of a compound according to claim 1, or a pharmaceutically acceptable salt thereof, to a patient in need thereof.

12. A pharmaceutical composition comprising a compound according to claim 1, or a pharmaceutically acceptable salt thereof, optionally together with one or more inert carriers and/or diluents.

13. A method for treating a disease or condition which is mediated by inhibiting the activity of AOC3, comprising administering a pharmaceutically effective amount of a compound according to claim 1, or a pharmaceutically acceptable salt thereof, to a patient in need thereof.

14. A pharmaceutical composition comprising one or more compounds according to claim 1, or a pharmaceutically acceptable salt thereof, and one or more additional therapeutic agents, optionally together with one or more inert carriers and/or diluents.

15. The method according to claim 13, wherein the disease or condition is selected from the group consisting of inflammatory diseases, eczema, pain, inflammatory bowel disease, multiple sclerosis, scleroderma, pulmonary diseases, nephropathy, diabetic proteinuria, kidney fibrosis, diabetic retinopathy, diabetic oedema, cancer, hepatocellular carcinoma, unspecified Colitis, rheumatoid Crohn's disease Colitis, biliary tract diseases, primary biliary cholangitis, primary sclerosing cholangitis, non-alcoholic steatohepatitis (NASH), non-alcoholic fatty liver disease (NAFLD), alcoholic liver disease, liver fibrosis, liver cirrhosis, ulcerative reperfusion injury, cerebral ischaemia, and transplant rejection.

16. The method according to claim 13, wherein the disease or condition is selected from the group consisting of vascular inflammatory diseases, arthritis, acute joint inflammation, chronic joint inflammation, atopic eczema, psoriasis ulcerative and rheumatoid psoriasis, musculoskeletal or nociceptive pain, non-infectious inflammatory bowel disease, respiratory distress syndrome, asthma, pulmonary fibrosis, idiopathic pulmonary fibrosis (IPF), chronic obstructive pulmonary disease (COPD), idiopathic inflammatory disease, macular diabetic oedema, melanoma, and lymphoma.

* * * * *